(12) United States Patent
Sakanaka et al.

(10) Patent No.: US 6,329,338 B1
(45) Date of Patent: Dec. 11, 2001

(54) DERIVATIVES OF CYCLODEPSIPEPTIDE PF1022 SUBSTANCE

(75) Inventors: Osamu Sakanaka; Yumiko Okada; Makoto Ohyama; Maki Matsumoto; Masaaki Takahashi; Yasushi Murai; Katsuharu Iinuma, all of Odawara (JP); Achim Harder, Leverkusen (DE); Norbert Mencke, Leverkusen (DE); Gerhard Bonse, Leverkusen (DE); Peter Jeschke, Leverkusen (DE)

(73) Assignees: Meiji Seika Kaisha, Ltd., Tokyo (JP); Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/043,558
(22) PCT Filed: Sep. 20, 1996
(86) PCT No.: PCT/JP96/02730
  § 371 Date: May 20, 1998
  § 102(e) Date: May 20, 1998
(87) PCT Pub. No.: WO97/11064
  PCT Pub. Date: Mar. 27, 1997

(30) Foreign Application Priority Data

Sep. 22, 1995  (JP) ................................... 7-224051

(51) Int. Cl.$^7$ ...................... A61K 38/12; A61K 31/395; C07D 273/00
(52) U.S. Cl. ............... 514/9; 514/11; 514/183; 530/317; 540/454
(58) Field of Search .............. 540/454; 514/9, 514/11, 183; 530/317

(56) References Cited

U.S. PATENT DOCUMENTS 5,514,773 * 5/1996 Nishiyama et al. ............... 530/317
5,717,063 * 2/1998 Scherkenbeck et al. ............. 530/323
5,747,448 * 5/1998 Ohyama et al. ........................ 514/11
5,777,075 * 7/1998 Scherkenbeck et al. ............. 530/330

FOREIGN PATENT DOCUMENTS 626 375 A1   11/1994  (EP).
6-184126  *  7/1994  (JP).
7-233068  *  9/1995  (JP).
WO 93/19053  *  9/1993  (WO).
WO 94/19334  *  9/1994  (WO).

* cited by examiner

Primary Examiner—Brenda Coleman
(74) Attorney, Agent, or Firm—Larson & Taylor PLC

(57) ABSTRACT

Novel derivatives of PF1022 substance, which are cyclodepsipeptides represented by the general formula (I) shown below or their salts are useful as anthelmintic agent for prevention or treatment of parasitic infections.

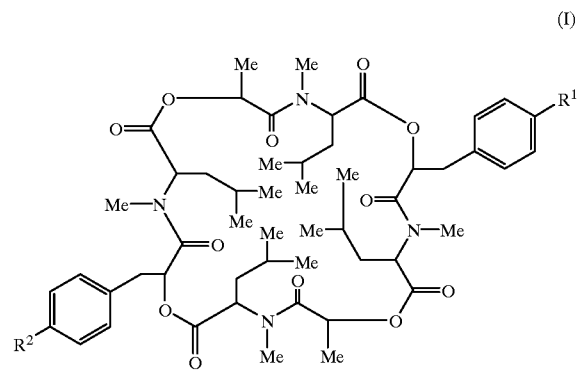

(I)

12 Claims, No Drawings

DERIVATIVES OF CYCLODEPSIPEPTIDE PF1022 SUBSTANCE

TECHNICAL FIELD

This invention relates to novel derivatives of PF1022 substance which have a skeletal structure of cyclodepsipeptide same as that of PF1022 substance, that is, a cyclodepsipeptide known as a fermentation product of a microorganism and having an antelmintic activity, and which exhibit a higher anthelmintic activity. This invention also relates to a vermicidal or anthelmintic composition containing said novel PF1022 derivative. The novel PF1022 derivatives according to this invention exhibit an excellent anthelmintic activity capable of expelling a variety of helminths or parasites living in animals and thus are very useful as an anthelmintic agent.

BACKGROUND ART

PF1022 substance is a known cyclodepsipeptide which was discovered as a result of studies on anthelmintic substances against fowl roundworms [refer to Japanese patent application Kokai No. Hei 3-35796, European patent application publication No. 0382173A2 and J. Antibiotics, 45, 692, (1992)]. The PF1022substance is a fermentation product which is produced by the cultivation of a filamentous fungus, PF1022 strain (deposited under FERM BP-2671 with National Institute of Bioscience and Human-Technology Agency in Tsukuba-City in terms of the Budapest Treaty) belonging to Agonomycetales. PF1022 substance is a compound classified into a class of cyclodepsipeptide compounds represented by the following formula (A)

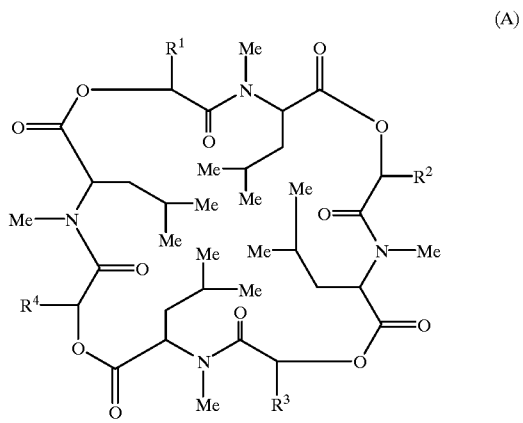

wherein Me stands for methyl group.

The cyclodepsipeptide represented by the above formula (A) includes the following eight particular substances.

PF1022 substance: $R^1=R^3=Me$, $R^2=R^4=CH_2C_6H_5$
PF1022 B substance: $R^1=R^2=R^3=R^4=CH_2C_6H_5$
PF1022 C substance: $R^1=Me$, $R^2=R^3=R^4=CH_2C_6H_5$
PF1022 D substance: $R^1=R^3=R^4=Me$, $R^2=CH_2C_6H_5$
PF1022 E substance: $R^1=R^3=Me$, $R^2=CH_2C_6H_4OH\text{-}p$, $R^4=CH_2C_6H_5$
PF1022 F substance: $R^1=R^2=R^3=R^4=Me$
PF1022 G substance: $R^1=R^2=R^3=Me$, $R^4=CH_2C_6H_4OH\text{-}p$
PF1022 H substance: $R^1=R^3=Me$, $R^2=R^4=CH_2C_6H_4OH\text{-}p$ The PF1022 substance is a cyclodepsipeptide which is formed of L—N-methylleucine [$(CH_3)_2CHCH_2CH$(NHCH$_3$)COOH] (abbreviated as H—L-MeLeu-OH), D-lactic acid [$CH_3CH(OH)$—COOH] (abbreviated as H—D-Lac-OH) and D-phenyl-lactic acid [$C_6H_5CH_2CH(OH)COOH$] (abbreviated H—D-PhLac-OH) via ester-bonds and amido-bonds and which may also be represented by the following formula (B):

Formula B: Cyclo(L-MeLeu-D-Lac-L-MeLeu-D-PhLac-L-MeLeu-D-Lac-L-MeLeu-D-PhLac)

The cultivation of the filamentous fungus PF1022 strain results not only in the production of PF1022 substance as the main product, but also in the production of PF1022 B substance, PF1022 C substance, PF1022 D substance, PF1022 E substance, PF1022 F substance, PF1022 G substance and PF1022 H substance which have the structures represented in the above formula (A), respectively [see Japanese patent application first publications Kokai Nos. Hei 3-35796, 5-170749 and 6-184126 and Japanese patent application No. Hei 8-208201 (filed on Aug. 7, 1996, not yet laid open)].

The PF1022 substance and PF1022 B to H substances all possess anthelmintic activities and have specific structural characteristics such that they have a common cyclodepsipeptide structure as a basic skeleton, that they have, as side chains, four N-methyl groups, four isobutyl groups, 0–4 methyl groups, 0–4 benzyl groups and 0–2 p-hydroxybenzyl groups and also that they have eight asymmetric carbon atoms in their molecules. Further, it can be presumed that the presence of a 24-membered ring formed of the four ester-linkages and four amido-linkages as shown in the formula (A) above plays an important role in the expression of biological activities.

So-called helminthic infections can cause serious damages to human and animal health and also to agricultural and stock-breeding industries, so that there always exists in the art, as an important theme, a demand for finding and providing such novel and useful substances which exhibit anthelmintic activities.

As explained above, PF1022 substance was found originally as a fermentation product, and later was prepared by chemical syntheses [see Japanese patent application first publication Kokai No. Hei 5–320148, and Biosci. Biotech. Biochem., 58, 1193 (1994)].

It is already known that PF1022 substance and PF1022 B to H substances themselves possess very high anthelmintic activities, but some researcher groups are still working in an attempt to produce and find out novel related substance(s) having a higher anthelmintic activity, with utilizing those PF1022 substances as the starting materials.

We, the present inventors, also have proceeded investigations from the initial stage when PF1022 substance was found, in order to produce and find out novel derivatives with starting from PF1022 substance and PF1022 B to H substances, and we have already found several novel derivatives (see internationally published specification No. WO94/19334 of PCT application No. PCT/JP/00252 and European patent application publication No. 0685469 A1 and Japanese patent application No. Hei 7-244051). One of the other researcher groups also has disclosed some novel derivatives as produced by total synthetic processes (see PCT international publications WO093/19033 and No. WO95/07272).

DISCLOSURE OF INVENTION

As described above, we have carried out our researches and development in an attempt to provide novel derivative (s) having a higher anthelmintic activity than that of PF1022 substance, by means of a method of chemical syntheses using the PF1022 substance as the starting compound. As a result, we have now been able to produce and find out several novel PF1022 derivatives which posesess an anthelmintic activity equal to or higher than that of any known PF1022 related compounds shown in the above-mentioned literatures and specifications.

Further, we have proceeded our investigations with taking notice of the D-phenyllactic acid moiety as one of the constituents of forming PF1022 substance, and now we have successfully synthesized novel cyclodepsipeptides which may be represented collectively by the undermentioned general formula (I), general formula (II) and general formula (III), through total synthetic processes or through chemical synthetic processes with starting from PF1022 substance, PF1022 E substance and PF1022 H substance. We have found that these novel PF1022 derivatives exhibit strong anthelmintic activities on the basis of animal tests.

According to a first aspect of this invention, therefore, there is provided a novel cyclodepsipeptide derivative of PF1022 substance, which is represented by the following general formula (I)

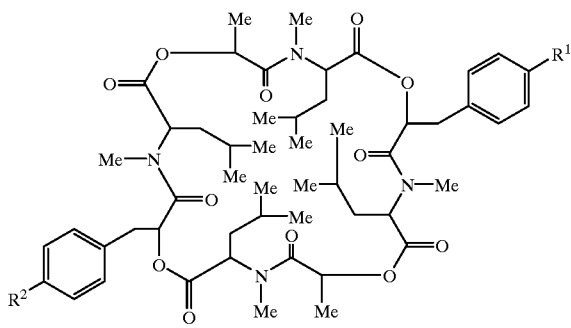

(I)

wherein (i) $R^1$ stands for a hydrogen atom and $R^2$ stand for a cyano-$(C_1-C_6)$alkoxy group, a thiocarbamoyl-$(C_1-C_6)$ alkoxy group, an amino-$(C_1-C_6)$alkoxy group, an amino-$(C_1-C_6)$alkoxy group having a protecting group, an N-mono-$(C_1-C_6)$alkylamino-$(C_1-C_6)$alkoxy group, an N,N-di-$(C_1-C_6)$alkylamino-$(C_1-C_6)$ alkoxy group, an N,N-di-$((C_1-C_6)$alkoxy-$(C_1-C_6)$alkyl)amino-$(C_1-C_6)$alkoxy group, or a cyclic amino-$(C_1-C_6)$alkoxy group of which the cyclic amino group is a 5- or 6-membered ring containing one or more nitrogen atoms and further optionally containing oxygen or sulfur atom(s) as the cyclic amino group-constituting atoms, or a $(C_1-C_6)$alkoxy group having as a substituent, a saturated or unsaturated 5- or 6-membered heterocyclic ring containing three or less hetero atoms (which is or are nitrogen atom, oxygen atom or sulfur atom) as the heterocyclic ring-constituting atoms and further optionally having as a substituent a phenyl group which may optionally be substituted by a $(C_1-C_6)$alkyl group, a $(C_3-C_6)$cycloalkyl group or a halogen atom (chlorine, bromine or fluorine), or a $(C_2-C_6)$alkanoyl group optionally having a substituent (which is a halogen atom or hydroxyl group), or an N-mono-$(C_1-C_6)$alkylcarbamoyl group, or an N,N-di-$(C_1-C_6)$ alkylcarbamoyl group, or a cyclic amino-carbonyl group of which the cyclic amino group is a 5- or 6-membered ring containing one or more nitrogen atoms and further optionally containing oxygen or sulfur atom(s) as the cyclic amino group-constituting atoms, or an N-mono-$(C_1-C_6)$ alkylamino-alkoxycarbonyl group, or an N,N-di-$(C_1-C_6)$ alkylamino-$(C_1-C_6)$alkoxycarbonyl group, or a cyclic amino-$(C_1-C_6)$ alkoxycarbonyl group of which the cyclic amino group is a 5- or 6-membered ring containing one or more nitrogen atoms and further optionally containing oxygen or sulfur atom(s) as the cyclic amino group-constituting atoms, or a formyloxy-$(C_1-C_6)$alkylcarbonyl group, or a carboxyl group, t-butyl group, 2-aminothiazolyl group, or t-butoxy group; or alternatively (ii) $R^1$ and $R^2$ are identical to each other and each stand for a cyano-$(C_1-C_6)$alkoxy group, a thiocarbamoyl-$(C_1-C_6)$alkoxy group, an amino-$(C_1-C_6)$alkoxy group, an amino-$(C_1-C_6)$ alkoxy group having a protecting group, an N-mono-$(C_1-C_6)$alkylamino-$(C_1-C_6)$alkoxy group, an N,N-di $(C_1-C_6)$alkylamino-$(C_1-C_6)$alkoxy group, an N,N-di-$((C_1-C_6)$ alkoxy-$(C_1-C_6)$ alkyl)amino-$(C_1-C_6)$alkoxy group, or a cyclic amino-$(C_1-C_6)$alkoxy group of which the cyclic amino group is a 5- or 6-membered ring containing one or more nitrogen atoms and further optionally containing oxygen or sulfur atom(s) as the cyclic amino group-constituting atoms, or a $(C_1-C_6)$ alkoxy group having as a substituent a saturated or unsaturated 5- or 6-membered heterocyclic ring containing three or less hetero atoms (which is or are nitrogen atom, oxygen atom or sulfur atom) as the heterocyclic ring-constituting atoms and further optionally having as a substituent a phenyl group which may optionally be substituted by a $(C_1-C_6)$alkyl group, a $(C_3-C_6)$cycloalkyl group or a halogen atom (chlorine, bromine or fluorine), or a $(C_2-C_6)$ alkanoyl group optionally having a substituent (which is a halogen atom or hydroxyl group), or an N-mono-$(C_1-C_6)$ alkylcarbamoyl group, or an N,N-di-$(C_1-C_6)$ alkylcarbamoyl group, or a cyclic amino-carbonyl group of which the cyclic amino group is a 5- or 6-membered ring containing one or more nitrogen atoms and further optionally containing oxygen or sulfur atom(s) as the cyclic amino group-constituting atoms, or an N-mono-$(C_1-C_6)$alkylamino-$(C_1-C_6)$ alkoxycarbonyl group, or an N,N-di-$(C_1-C_6)$ alkylamino-$(C_1-C_6)$alkoxycarbonyl group, or a cyclic amino-$(C_1-C_6)$ alkoxycarbonyl group of which the cyclic amino group is a 5- or 6-membered ring containing one or more nitrogen atoms and further optionally containing oxygen or sulfur atom(s) as the cyclic amino group-constituting atoms, or a formyloxy-$(C_1-C_6)$alkylcarbonyl group, or a carboxyl group, t-butyl group, 2-aminothiazolyl group or t-butoxy group, and Me stands for methyl group.

In general formula(I) above, where $R^1$ or $R^2$ stands for such a cyclic amino-$(C_1-C_6)$alkoxy group, cyclic amino-carbonyl group or cyclic amino-$(C_1-C_6)$alkoxycarbonyl group of which the cyclic amino group is a 5- or 6-membered ring containing one or more nitrogen atoms and further optionally containing oxygen or sulfur atom(s) as the cyclic amimo group-constituting atoms, some preferred examples of the cyclic amino group contained in the aforesaid groups are morpholino group, pyrrolidino group and piperidino group. Further, in general formula(I) above, where $R^1$ or $R^2$ stands for a $(C_1-C_6)$alkoxy group having a saturated or unsaturated 5- or 6-membered heterocyclic ring as a substituent, some preferred examples of said heterocyclic ring are pyrrolidine, imidazole, thiazole, furan, tetrahydrofuran, a 5-$(C_1-C_6)$ alkyl-1,2,4-oxadiazole, a 5-(halo-substituted or unsubstituted) phenyl-1,2,4-oxadiazole, a 5-$(C_1-C_6)$ cycloalkyl-1,2,4-oxadiazole, a halo-substituted or unsubstituted pyridine, and an N-alkyl-substituted or unsubstituted tetrahydropyrimidine.

According to a second aspect of this invention, there is provided a cyclodepsipeptide derivative of PF1022 substance, which is represented by the following general formula (II)

(II)

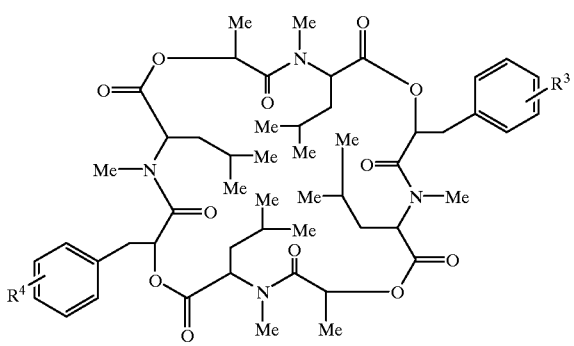

wherein (i) $R^3$ stands for a hydrogen atom and $R^4$ stands for a morpholino group bonded to any of the ortho-, meta- and para-position of the phenyl group shown in the above formula; or alternatively (ii) $R^3$ stands for a morpholino group bonded to any of the ortho-, meta- and para-positions of the phenyl group shown in the above formula and $R^4$ stands for a morpholino group bonded to the ortho- or meta-position of the phenyl group and Me stands for methyl group.

Further, according to a third aspect of this invention, there is provided a cyclodepsipeptide derivative of PF1022 substance, which is represented by the following general formula (III)

(III)

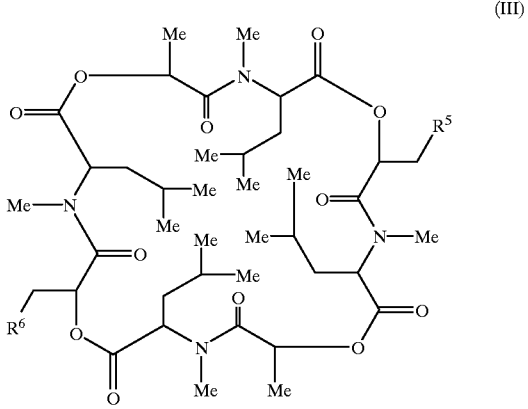

wherein (i) $R^6$ stands for a phenyl group and $R^5$ stands for a carboxyl group, a protected carboxyl group, a ($C_1$–$C_6$) alkoxycarbonyl group, an unsaturated 5- or 6-membered heterocyclic ring containing one or more nitrogen, oxygen or sulfur atoms as the hetero atom of said ring, or a bicyclic fused heterocyclic ring as formed by fusion of said unsaturated 5- or 6-membered heterocyclic ring with a benzene ring, or alternatively (ii) $R^5$ and $R^6$ are identical to each other and each stand for a carboxyl group, a protected carboxyl group, a ($C_1$–$C_6$)alkoxycarbonyl group, or an unsaturated 5- or 6-membered heterocyclic ring containing one or more nitrogen, oxygen or sulfur atoms as the hetero atom of said ring, or a bicyclic fused heterocyclic ring as formed by fusion of said unsaturated 5- or 6-membered heterocyclic ring with a benzene ring, and Me stands for methyl group.

In general formula (III) above, where $R^1$ or $R^2$ stands for an unsaturated 5- or 6-membered heterocyclic ring or a bicyclic fused heterocyclic ring as formed by fusion of said unsatutated heterocyclic ring with a benzene ring, some preferred examples of the heterocyclic ring or fused ring are benzothiazolyl group, benzimidazolyl group and 2-aminothiazolyl group.

Best Mode for Carrying Out the Invention

A preferred embodiment of the novel derivative of PF1022 substance of the general formula (I) according to the first aspect of this invention can be a cyclodepsipeptide of general formula (I) wherein $R^1$ is a hydrogen atom and $R^2$ is a cyanomethoxy group, thiocarbamolymethoxy group, 2-aminoethoxy group, 2-(N-t-butyloxycarbonylamino) ethoxy group, a 2-(N-mono-($C_1$–$C_6$)alkylamino)ethoxy or 3-(N-mono-($C_1$–$C_6$)alkylamino)propoxy group, a 2-(N,N-di-($C_1$–$C_6$)alkylamino)ethoxy or 3-(N,N-di-($C_1$–$C_6$) alkylamino)propoxy group, a 2-(N,N-di-($C_1$–$C_6$)alkoxy-($C_1$–$C_6$)alkyl)amino)ethoxy group, 2-morpholinoethoxy group, 2-pyrrolidinoethoxy group, 2-piperidinoethoxy group, or a methoxy group substituted by a heterocyclic ring which is pyrrolidine, imidazole, thiazole, furan, tetrahydrofuran, a 5-(linear or branched $C_1$–$C_6$)alkyl-1,2,4-oxadiazole, a 5-(optionally halo-substituted)phenyl-1,2,4-oxadiazole, a 5-($C_3$–$C_6$) cycloalkyl-1,2,4-oxadiazole, a pyridine optionally substituted by a halogen atom, or an N—(($C_1$–$C_6$) alkyltetrahydropyrimidine, or $R^2$ is an acetyl group optionally substituted by a substituent (a halogen atom or hydroxyl group), or a carbamoyl group, N-methylcarbamoyl group, N,N-dimethylcarbamoyl group, morpholinocarbonyl group, an N-mono-($C_1$–$C_6$) alkylaminoethoxycarbonyl group, an N,N-di-($C_1$–$C_6$) alkylaminoethoxycarbonyl group, morpholinoethoxycarbonyl group, formyloxymethylcarbonyl group, carboxyl group, t-butyl group, 2-aminothiazolyl group or t-butoxy group; or alternatively (ii) $R^1$ and $R^2$ are identical to each other and each are a cyanomethoxy group, thiocarbamoyl-methoxy group, 2-aminoethoxy group, 2-(N-t-butyloxycarbonylamino)ethoxy group, a 2-(N-mono-($C_1$–$C_6$)alkylamino)ethoxy or 3-(N-mono-($C_1$–$C_6$) alkylamino)propoxy group, a 2-(N,N-di-($C_1$–$C_6$) alkylamino)ethoxy or 3-(N,N-di-($C_1$–$C_6$)alkylamino) propoxy group, a 2-(N,N-di-($C_1$–$C_6$)alkoxy-($C_1$–$C_6$) alkylamino)ethoxy group, 2-morpholinoethoxy group, 2-pyrrolidinoethoxy group, 2-piperidinoethoxy group, or a methoxy group substituted by a heterocyclic ring which is pyrrolidine, imidazole, thiazole, furan, tetrahydrofuran, a 5-(linear or branched $C_1$–$C_6$)alkyl-1,2,4-oxadiazole, a 5-(optionally halo-substituted) phenyl-1,2,4-oxadiazole, a 5-($C_3$–$C_6$)cycloalkyl-1,2,4-oxadiazole, a pyridine optionally substituted by a halogen atom, or an N—($C_1$–$C_6$)alkyl-tetrahydropyrimidine, or $R^1$ and $R^2$ are each an acetyl group optionally substituted by a substituent (a halogen atom or hydroxyl group), or a carbamoyl group, N-methylcarbamoyl group, N,N-dimethylcarbamoyl group, morpholinocarbonyl group, an N-mono-($C_1$–$C_6$)alkylamino-ethoxycarbonyl group, an N,N-di-($C_1$–$C_6$)alkylamino-ethoxycarbonyl group, morpholinoethoxycarbonyl group, formyloxymethylcarbonyl group, carboxyl group, t-butyl group, 2-aminothiazolyl group or t-butoxy group.

The cyclodepsipeptide derivative of general formula (I) according to the first aspect of this invention includes, as its preferred embodiments, the compounds of the following classes (a) to (c).

(a) Cyclodepsipeptide of general formula (I) wherein (i) $R^1$ is a hydrogen atom, and $R^2$ is a cyano-($C_1$–$C_6$)alkoxy group, a thiocarbamoyl-($C_1$–$C_6$)alkoxy group, an amino-($C_1$–$C_6$)alkoxy group, an amino-($C_1$–$C_6$)alkoxy group having a protecting group, an N-mono-($C_1$–$C_6$)alkylamino-($C_1$–$C_6$)alkoxy group, an N,N-di-(($C_1$–$C_6$)alkylamino-($C_1$–$C_6$)alkoxy group, an N,N-di-(($C_1$–$C_6$)alkoxy-($C_1$–$C_6$)

alkyl)amino-$(C_1-C_6)$alkoxy group, or a cyclic amino-$(C_1-C_6)$alkoxy group of which the cyclic amino group is a 5- or 6-membered ring containing one or more nitrogen atoms and further optionally containing oxygen atom or sulfur atom as the cyclic amino group-constituting atoms, or $R^2$ is t-butoxy group; or alternatively (ii) $R^1$ and $R^2$ are identical to each other and each are a cyano-$(C_1-C_6)$alkoxy group, a thiocarbamoyl-$(C_1-C_6)$alkoxy group, an amino-$(C_1-C_6)$alkoxy group, an amino-$(C_1-C_6)$alkoxy group having a protecting group, an N-mono-$(C_1-C_6)$alkylamino-$(C_1-C_6)$alkoxy group, an N,N-di-$(C_1-C_6)$alkylamino-$(C_1-C_6)$alkoxy group, an N,N-di-$((C_1-C_6)$alkoxy-$(C_1-C_6)$alkyl)amino-$(C_1-C_6)$alkoxy group, or a cyclic amino-$(C_1-C_6)$alkoxy group of which the cyclic amino group is a 5- or 6-membered ring containing one or more nitrogen atoms and further optionally containing oxygen atom or sulfur atom as the cyclic amino group-constituting atoms, or $R^1$ and $R^2$ are each t-butoxy group.

In the cyclodepsipeptide just above-mentioned, it is preferable that (i) $R^1$ is a hydrogen atom and $R^2$ is a cyanomethoxy group, thiocarbamoylmethoxy group, a 2-aminoethoxy group, 2-(N-t-butyloxycarbonylamino) ethoxy group, a 2-(N-mono-$(C_1-C_6)$alkylamino)ethoxy or 3-(N-mono-$(C_1-C_6)$alkylamino)propoxy group, a 2-(N,N-di-$(C_1-C_6)$alkylamino)ethoxy or 3-(N,N-di-$(C_1-C_6)$alkylamino)propoxy group, a 2-(N,N-di-$((C_1-C_6)$alkoxy-$(C_1-C_6)$alkyl)amino)ethoxy group, 2-morpholinoethoxy group, 2-pyrrolidinoethoxy group or 2-piperidinoethoxy group or t-butoxy group; or alternatively that (ii) $R^1$ and $R^2$ are the same with each other and each are a cyanomethoxy group, 2-aminoethoxy group, 2-(N-t-butyloxycarbonylamino)ethoxy group, a 2-(N-mono-$(C_1-C_6)$-alkylamino)ethoxy or 3-(N-mono-$(C_1-C_6)$ alkylamino)propoxy group, a 2-(N,N-di-$(C_1-C_6)$ alkylamino)ethoxy or 3-(N,N-di-$(C_1-C_6)$alkylamino) propoxy group, a 2-(N,N-di-$((C_1-C_6)$alkoxy-$(C_1-C_6)$alkyl) amino)ethoxy group, 2-morpholinoethoxy group, 2-pyrrolidinoethoxy group or 2-piperidinoethoxy group, or t-butoxy group.

(b) Cyclodepsipeptide of general formula (I) wherein $R^1$ is a hydrogen atom, and $R^2$ is a $(C_1-C_6)$ alkoxy group having, as a substituent, such a saturated or unsaturated 5- or 6-membered heterocyclic ring which contains three or less hetero atoms (being nitrogen, oxygen or sulfur atoms) as the heterocyclic ring-constituting atoms and which may optionally have as a substituent a $(C_1-C_6)$alkyl group or a $(C_3-C_6)$ cycloalkyl group or a phenyl group optionally substituted by a halogen atom; or alternatively (ii) $R^1$ and $R^2$ are each independently a $(C_1-C_6)$alkoxy group having as a substituent such a saturated or unsaturated 5- or 6-membered heterocyclic ring which contains three or less hetero atoms (being nitrogen, oxygen or sulfur atoms) as the heterocyclic ring-constituting atoms and which may optionally have as a substituent a $(C_1-C_6)$alkyl group or a $(C_3-C_6)$cycloalkyl group or a phenyl group optionally substituted by a halogen atom.

In the cyclodepsipeptide just above-mentioned, the heterocyclic ring, which is referred to for the $(C_1-C_6)$alkoxy group having as a substituent a heterocyclic ring as represented by $R^1$ and/or $R^2$, may be a pyrrolidine, imidazole, thiazole, furan, tetrahydrofuran, a 5-$(C_1-C_6)$, linear or branched)alkyl-1,2,4-oxadiazole, a 5-(optionally halo-substituted)-phenyl-1,2,4-oxadiazole, a 5-$(C_3-C_6)$ cycloalkyl-1,2,4-oxadiazole, a pyridine optionally substituted by a halogen, or an N—$(C_1-C_6)$alkyl-tetrahydropyrimidene. Further, $R^2$, or both of $R^1$ and $R^2$ may be a methoxy group which is substituted by such specific heterocyclic ring as above-mentioned.

(c) Cyclodepsipeptide of general formula (I) wherein $R^1$ is a hydrogen atom, and $R^2$ is a $(C_2-C_6)$alkanoyl group optionally substituted by a halogen atom or hydroxy group as s substituent, or an N-mono-$(C_1-C_6)$alkylcarbamoyl group, an N,N-di-$(C_1-C_6)$alkylcarbamoyl group, a cyclic amino-carbonyl group of which the cyclic amino group is a 5- or 6-membered ring containing one or more nitrogen atoms and further optionally containing oxygen or sulfur atom(s) as the cyclic amino group-constituting atoms, an N-mono-$(C_1-C_6)$alkylamino-alkoxycarbonyl group, an N,N-di-$(C_1-C_6)$alkylamino-alkoxycarbonyl group, a cyclic amino-$(C_1-C_6)$alkoxycarbonyl group of which the cyclic amino group is a 5- or 6-membered ring containing one or more nitrogen atoms and further optionally containing oxygen or sulfur atom(s) as the cyclic amino group-constituting atoms, a formyloxy-$(C_1-C_6)$alkylcarbonyl group, carboxyl group, t-butyl group, or 2-aminothiazolyl group; or alternatively (ii) $R^1$ and $R^2$ are identical to each other and each are a $(C_2-C_6)$alkanoyl group optionally substituted by a halogen atom or hydroxyl group as a substituent, or an N-mono-$(C_1-C_6)$alkylcarbamoyl group, an N,N-di-$(C_1-C_6)$ alkylcarbamoyl group, a cyclic amino-carbonyl group of which the cyclic amino group is a 5- or 6-membered ring containing one or more nitrogen atoms and further optionally containing oxygen or sulfur atom(s) as the cyclic amino group-constituting atoms, an N-mono-$(C_1-C_6)$alkylamino-alkoxycarbonyl group, an N,N-di-$(C_1-C_6)$alkylamino-alkoxycarbonyl group, a cyclic amino-$(C_1-C_6)$-alkoxycarbonyl group of which the cyclic amino group is a 5- or 6-membered ring containing one or more nitrogen atoms and further optionally containing oxygen or sulfur atom(s) as the cyclic amino group-constituting atoms, a formyloxy-$(C_1-C_6)$alkylcarbonyl group, carboxyl group, t-butyl group, or 2-aminothiazolyl group.

In the cyclodepsipeptides referred to just above, it is preferable that (i) $R^1$ is a hydrogen atom and $R^2$ is a carboxyl group, an acetyl group optionally substituted by a halogen atom or hydroxyl group as a substituent, a carbamoyl group, N-methylcarbamoyl group, an N,N-dimethylcarbamoyl group, morpholinocarbonyl group, an N-mono-$(C_1-C_6)$ alkylamino-ethoxycarbonyl group, an N,N-di-$(C_1-C_6)$ alkylamino-ethoxycarbonyl group, morpholinoethoxycarbonyl group or formyloxymethoxycarbonyl group; or alternatively (ii) $R^1$ and $R^2$ are identical to each other and each are a carboxyl group, an acetyl group optionally substituted by a halogen atom or hydroxyl group as a substituent, a carbamoyl group, an N-methylcarbamoyl group, an N,N-dimethylcarbamoyl group, a morpholinocarbonyl group, an N-mono-$(C_1-C_6)$alkylamino-ethoxycarbonyl group, an N,N-di-$(C_1-C_6)$alkylamino-ethoxycarbonyl group, a morpholinoethoxycarbonyl group or formyloxymethoxycarbonyl group.

According to a preferred embodiment of the cyclodepsipeptide of general formula (II) in the second aspect of this invention, there are exemplified such a cyclodepsipeptide of general formula (II) wherein (i) $R^3$ is a hydrogen atom and $R^4$ is a morpholino group bonded to the para-position of the phenyl group shown in the formula, or alternatively (ii) $R^3$ is a morpholino group bonded to the ortho-or para-position of the phenyl group and $R^4$ is a morpholino group bonded to the ortho-position of the phenyl group.

According to a preferred embodiment of the cyclodepsipeptides of general formula (III) in the third aspect of this invention, there are exemplified such a cyclodepsipeptide of general formula (III) wherein (i) $R^6$ is a phenyl group and $R^5$ is a carboxyl group, methoxycarbonyl group, diphenyl-methoxycarbonyl group, benzothiazolyl group or benzimidazolyl group, or alternatively (ii) $R^5$ and $R^6$ are identical to each other and each are a carboxyl group, methoxycarbonyl group, diphenylmethoxycarbonyl group, benzothiazolyl group or benzimidazolyl group.

Concrete examples of the cyclodepslipeptide of general formula (I) according to the first aspect of this invention include such compounds which are produced by Examples 4–46, 49–64, 67–68 and 72 given hereinafter. As concrete examples of the cyclodepsipeptide of general formula (II) according to the second aspect of this invention, there are such compounds which are produced by Examples 65–66 shown hereinafter. Further, as concrete examples of the cyclodepsipeptide of general formula (III) according to the third aspect of this invention, there are such compounds which are produced by Examples 47–48, 69, 70 and 71 given hereinafter.

Amongst the cycdepsipeptides of general formula (I), general formula (II) and general formula (III) according to this invention, the particular compounds of the following Examples are especially preferred.

Example 4. Cyclo[MeLeu-Lac-MeLeu-(NCCH$_2$O)PhLac-MeLeu-Lac-MeLeu-PhLac]

Example 5. Cyclo[MeLeu-Lac-MeLeu-(BocNHCH$_2$CH$_2$O)PhLac-MeLeu-Lac-MeLeu-PhLac]

Example 6. Cyclo[MeLeu-Lac-MeLeu-(NH$_2$CH$_2$CH$_2$O)PhLac-MeLeu-Lac-MeLeu-PhLac] (Compound Code No. PF1022-278)

Example 7. Cyclo[MeLeu-Lac-MeLeu-((CH$_3$)$_2$NCH$_2$CH$_2$O)PhLac-MeLeu-Lac-MeLeu-PhLac] (Compound Code No. PF1022-235)

Example 8. Cyclo[MeLeu-Lac-MeLeu-((C$_2$H$_5$)$_2$NCH$_2$CH$_2$O)PhLac-MeLeu-Lac-MeLeu-PhLac] (Compound Code No. PF1022-236)

Example 9. Cyclo[MeLeu-Lac-MeLeu-(Pr$_2$NCH$_2$CH$_2$O)PhLac-MeLeu-Lac-MeLeu-PhLac] (Compound Code No. PF1022-270)

Example 10. Cyclo[MeLeu-Lac-MeLeu-(Bu$_2$NCH$_2$CH$_2$O)PhLac-MeLeu-Lac-MeLeu-PhLac] (Compound Code No. PF1022-271)

Example 11. Cyclo[MeLeu-((CH$_3$OCH$_2$CH$_2$)$_2$NCH$_2$CH$_2$O)PhLac-MeLeu-Lac-MeLeu-PhLac-MeLeu-Lac] (Compound Code No. PF1022-238)

Example 12. Cyclo[MeLeu-(MorCH$_2$CH$_2$O)PhLac-MeLeu-Lac-MeLeu-PhLac-MeLeu-Lac] (PF1022-239)

Example 13. Cyclo[MeLeu-Lac-MeLeu-(PyrCH$_2$CH$_2$O)PhLac-MeLeu-Lac-MeLeu-PhLac] (Compound Code No. PF1022-284)

Example 14. Cyclo[MeLeu-Lac-MeLeu-(pipCH$_2$CH$_2$O)PhLac-MeLeu-Lac-MeLeu-PhLac] (Compound Code No. PF1022-285)

Example 15. Cyclo[MeLeu-Lac-MeLeu-((C$_2$H$_5$)$_2$NCH$_2$CH$_2$CH$_2$O)PhLac-MeLeu-Lac-MeLeu-PhLac] (Compound Code No. PF1022-274)

Example 16. Cyclo[MeLeu-Lac-MeLeu-((S)-pyrrolidinyl-2-methoxy)PhLac-MeLeu-Lac-MeLeu-PhLac] (Compound Code No. PF1022-302)

Example 17. Cyclo[MeLeu-Lac-MeLeu-(4-imidazolyl-4-methoxy)PhLac-MeLeu-Lac-MeLeu-PhLac] (PF1022-304)

Example 18. Cyclo[MeLeu-Lac-MeLeu-(H$_2$NCSCH$_2$O)PhLac-MeLeu-Lac-MeLeu-PhLac]

Example 19. Cyclo[MeLeu-Lac-MeLeu-(2-imidazolylmethoxy)PhLac-MeLeu-Lac-MeLeu-PhLac] (PF1022-305)

Example 20. Cyclo[MeLeu-Lac-MeLeu-(2-thiazolylmethoxy)PhLac-MeLeu-Lac-MeLeu-PhLac] (Compound Code No. PF1022-306)

Example 21. Cyclo[MeLeu-Lac-MeLeu-(3-(5-methyl-1,2,4-oxadiazolyl)-methoxy)PhLac-MeLeu-Lac-MeLeu-PhLac] (Compound Code No. PF1022-309)

Example 22. Cyclo[MeLeu-Lac-MeLeu-(3-(5-isobutyl-1,2,4-oxadiazolyl)methoxy)PhLac-MeLeu-Lac-MeLeu-PhLac] (Compound Code No. PF1022-310)

Example 23. Cyclo[MeLeu-Lac-MeLeu-(3-(5-(2,6-difluorophenyl)-1,2,4-oxadiazolyl)methoxy)PhLac-MeLeu-Lac-MeLeu-PhLac] (Compound Code No. PF1022-311)

Example 24. Cyclo[MeLeu-Lac-MeLeu-(furfuryloxy)PhLac-MeLeu-Lac-MeLeu-PhLac] (Compound Code No. PF1022-312)

Example 25. Cyclo[MeLeu-Lac-MeLeu-(tetrahydrofurfuryloxy)PhLac-MeLeu-Lac-MeLeu-PhLac] (Compound Code No. PF1022-313)

Example 26. Cyclo[MeLeu-Lac-MeLeu-(2-picolyloxy)PhLac-MeLeu-Lac-MeLeu-PhLac] (Compound Code No. PF1022-314)

Example 27. Cyclo[MeLeu-Lac-MeLeu-(3-picolyl)PhLac-MeLeu-Lac-MeLeu-PhLac] (Compound Code No. PF1022-315)

Example 28. Cyclo[MeLeu-Lac-MeLeu-(4-picolyl)PhLac-MeLeu-Lac-MeLeu-PhLac] (Compound Code No. PF1022-316)

Example 29. Cyclo[MeLeu-Lac-MeLeu-(6-chloro-3-picolyloxy)PhLac-MeLeu-Lac-MeLeu-PhLac] (Compound Code No. PF1022-317)

Example 30. Cyclo[MeLeu-Lac-MeLeu-(2-(1N-methyl-1,4,5,6-tetrahydropyrimidyl)methoxy)PhLac-MeLeu-Lac-MeLeu-PhLac] (Compound Code No. PF1022-318)

Example 31. Cyclo[MeLeu-Lac-MeLeu-(3-(5-isopropyl-1,2,4-oxadiazolyl)-methoxy)PhLac-MeLeu-Lac-MeLeu-PhLac] (Compound Code No. PF1022-341)

Example 32. Cyclo[MeLeu-Lac-MeLeu-(3-(5-cyclohexyl-1,2,4-oxadiazolyl)-methoxy)PhLac-MeLeu-Lac-MeLeu-PhLac] (Compound Code No. PF1022-343)

Example 33. Cyclo[MeLeu-Lac-MeLeu-(NCCH$_2$O)PhLac]$_2$

Example 34. Cyclo[MeLeu-Lac-MeLeu-(BocNHCH$_2$CH$_2$O)PhLac]$_2$

Example 36. Cyclo[MeLeu-Lac-MeLeu-((CH$_3$)$_2$NCH$_2$CH$_2$O)PhLac]$_2$ (Compound Code No. PF1022-262)

Example 37. Cyclo[MeLeu-Lac-MeLeu-((C$_2$H$_5$)$_2$NHCH$_2$H$_2$O)PhLac]$_2$ (Compound Code No. PF1022-263)

Example 38. Cyclo[MeLeu-Lac-MeLeu-(MorCH$_2$H$_2$O)PhLac]$_2$ (Compound Code No. PF1022-266)

Example 39. Cyclo[MeLeu-Lac-MeLeu-(3-(5-isobutyl-1,2,4-oxadiazolylmethoxy)PhLac]$_2$ (Compound Code No. PF1022-330)

Example 40. Cyclo[MeLeu-Lac-MeLeu-(3-(5-(2,6-difluorophenyl)-1,2,4-oxadiazolyl)methoxy)PhLac]$_2$ (Compound Code No. PF1022-331)

Example 41. Cyclo[MeLeu-Lac-MeLeu-(tetrahydrofurfuryloxy)PhLac]$_2$ (Compound Code No. PF1022-333)

Example 42. Cyclo[MeLeu-Lac-MeLeu-(2-picolyloxy)PhLac]$_2$ (Compound Code No. PF1022-334)

Example 43. Cyclo[MeLeu-Lac-MeLeu-(3-(5-isopropyl-1,2,4-oxadiazolyl)-methoxy)PhLac]$_2$ (Compound Code No. PF1022-345)

Example 44. Cyclo[MeLeu-Lac-MeLeu-(3-(5-cyclohexyl-1,2,4-oxadiazolyl)-methoxy)PhLac]$_2$ (Compound Code No. PF1022-347)

Example 45. Cyclo[MeLeu-Lac-MeLeu-PhLac-MeLeu-Lac-MeLeu-(NH$_2$CO)PhLac] (Compound Code No. PF1022-242)

Example 46. Cyclo[MeLeu-Lac-MeLeu-(NH$_2$CO)PhLac]$_2$ (Compound Code No. PF1022-247)

Example 47. Cyclo[MeLeu-Lac-MeLeu-(HOCO)Lac]$_2$ (Compound Code No. PF1022-030) and Cyclo[MeLeu-Lac- MeLeu-(HOCO)Lac-MeLeu-Lac-MeLeu-PhLac] (Compound Code No. PF1022-031)

Example 48. Cyclo[MeLeu-Lac-MeLeu-(($C_6H_5$)$_2$CHOCO) Lac]$_2$ (Compound Code No. PF1022-045) and Cyclo [MeLeu-Lac-MeLeu-($C_6H_5$)$_2$CHOCO)Lac-MeLeu-Lac-MeLeu-PhLac] (Compound Code No. PF1022-046)

Example 49. Cyclo[MeLeu-Lac-MeLeu-($CH_3$CO)PhLac-MeLeu-Lac-MeLeu-PhLac] and Cyclo[MeLeu-Lac-MeLeu-($CH_3$CO)PhLac-MeLeu-Lac-MeLeu-($CH_3$CO)PhLac] (Compound Code No. PF1022-049 and PF1022-048)

Example 50. Cyclo[MeLeu-Lac-MeLeu-(BrCH$_2$CO)PhLac-MeLeu-Lac-MeLeu-PhLac]

Example 51. Cyclo[MeLeu-Lac-MeLeu-(HCOOCH$_2$CO) PhLac-MeLeu-Lac-MeLeu-PhLac]

Example 52. Cyclo[MeLeu-Lac-MeLeu-(HOCH$_2$CO) PhLac-MeLeu-Lac-MeLeu-PhLac]

Example 53. Cyclo[MeLeu-Lac-MeLeu-(HOCO)PhLac-MeLeu-Lac-MeLeu-PhLac] (Compound Code No. PF1022-241)

Example 54. Cyclo[MeLeu-Lac-MeLeu-(MorCO)PhLac-MeLeu-Lac-MeLeu-PhLac] (Compound Code No. PF1022-244)

Example 55. Cyclo[MeLeu-Lac-MeLeu-(($CH_3$)$_2$NCO) PhLac-MeLeu-Lac-MeLeu-PhLac] (Compound Code No. PF1022-243)

Example 56. Cyclo[MeLeu-Lac-MeLeu-(($CH_3$)$_2$NCH$_2$CH$_2$OCO)PhLac-MeLeu-Lac-MeLeu-PhLac] (Compound Code No. PF1022-245)

Example 57. Cyclo[MeLeu-Lac-MeLeu-(MorCH$_2$CH$_2$OCO)PhLac-MeLeu-Lac-MeLeu-PhLac] (Compound Code No. PF1022-246)

Example 58. Cyclo[MeLeu-Lac-MeLeu-(BrCH$_2$CO)PhLac]$_2$

Example 59. Cyclo[MeLeu-Lac-MeLeu-(HCOOCH$_2$CO)PhLac]$_2$

Example 60. Cyclo[MeLeu-Lac-MeLeu-(HOCH$_2$CO)PhLac]$_2$

Example 61. Cyclo[MeLeu-Lac-MeLeu-(OHCO)PhLac]$_2$

Example 62. Cyclo[(MeLeu-Lac-MeLeu-(($CH_3$)$_2$NCO)PhLac]$_2$ (Compound Code No. PF1022-248)

Example 63. Cyclo[MeLeu-Lac-MeLeu-(MorCO)PhLac$_2$ (Compound Code No. PF1022-249)

Example 64. Cyclo[MeLeu-Lac-MeLeu-(MorCH$_2$CH$_2$OCO)PhLac]$_2$ (Compound Code No. PF1022-251)

Example 65. Cyclo[MeLeu-(Mor)PhLac-MeLeu-Lac-MeLeu-PhLac-MeLeu-Lac] (Compound Code No. PF1022-233)

Example 66. Cyclo[MeLeu-(o-Mor)PhLac-MeLeu-Lac-MeLeu-(p-Mor)PhLac-MeLeu-Lac] (Compound Code No. PF1022-280) and Cyclo[MeLeu-(o-Mor)PhLac-MeLeu-Lac]$_2$ (Compound Code No. PF1022-281)

Example 67. Cyclo[MeLeu-Lac-MeLeu-(t-Bu)PhLac-MeLeu-Lac-MeLeu-PhLac] and Cyclo[MeLeu-Lac-MeLeu-(t-Bu)PhLac]$_2$ (Compound Code No. PF1022-051 and PF1022-050)

Example 68. Cyclo[MeLeu-Lac-MeLeu-(t-BuO)PhLac]$_2$ (Compound Code No. PF1022-222)

Example 69. Cyclo[MeLeu-Lac-MeLeu-(BTH)Lac-MeLeu-Lac-MeLeu-PhLac] (Compound Code No. PF1022-038)

Example 70. Cyclo[MeLeu-Lac-MeLeu-(BTH)Lac]$_2$ (Compound Code No. PF1022-037)

Example 71. Cyclo[MeLeu-Lac-MeLeu-(BIM)Lac-MeLeu-Lac-MeLeu-PhLac] (Compound Code No. PF1022-040)

Example 72. Cyclo[MeLeu-Lac-MeLeu-(ATH)PhLac]$_2$ (Compound Code No. PF1022-056).

Referring to the above list of Examples, the substances of Examples 4–46, 49–64, 67, 68 and 72 are examples of the compounds of general formula (I), the substances of Examples 65 and 66 are examples of the compounds of general formula (II), and the substances of Examples 47, 48 and 69–71 are examples of the compounds of general formula (III).

[I] Next, processes for the preparation of the new derivatives of PF1022 substance of general formula (I) according to this invention are explained.

1. Processes Comprising the Chemical Conversion of PF1022 E Substance

The known PF1022 E substance, namely such compound of general formula (I) wherein $R^1$ is hydrogen atom and $R^2$ is hydroxyl group, may be used as the starting material in the below-described processes in order to synthesize such compounds of general formula (I) where $R^1$ is hydrogen atom and $R^2$ is a cyano-($C_1$–$C_6$)alkoxy group, thiocarbamoyl-($C_1$–$C_6$)alkoxy group, amino-($C_1$–$C_6$)alkoxy group, amino-($C_1$–$C_6$)alkoxy group having a protecting group, N-mono-($C_1$–$C_6$)alkylamino-($C_1$–$C_6$)alkoxy group, N,N-di-(($C_1$–$C_6$) alkoxy-($C_1$–$C_6$)alkyl)amino-($C_1$–$C_6$)alkoxy group, or a cyclic amino-($C_1$–$C_6$) alkoxy group of which the cyclic amino group is a 5- or 6-membered ring containing one or more nitrogen atoms and further optionally containing oxygen atom or sulfur atom as the cyclic amino group-constituting atoms, or a ($C_1$–$C_6$) alkoxy group having as a substituent such a saturated or unsaturated 5- or 6 membered heterocyclic ring which contains three or less hetero atoms (nitrogen, oxygen or sulfur atoms) as the heterocyclic ring-constituting atoms and which may have a substituent(being a $C_1$–$C_6$-alkyl group or a $C_3$–$C_6$-cycloalkyl group or a phenyl group optionally substituted by a halogen atom), or $R^2$ is t-butoxy group.

PF1022 E substance may be obtained from the culture broth of the PF1022 substance-producing strain by a fermentation process and by itself has an anthelmintic activity against worms parasitic on animals. We have paid attention on that the possibility of chemical modification of PF1022 E substance would have been extended due to the presence of a phenolic hydroxyl group at the para-position of one of the two benzene rings in the molecule of PF1022 E substance. And thus, we can have synthesized the novel derivative according to this invention, by applying various chemical conversion procedures to the PF1022 E substance. PF1022 E substance itself may also be synthesized from PF1022 substance by the following method:

1-1. Syntheses of PF1022 E Substance from PF1022 Substance

PF1022 E substance can be produced either by a fermentation process (see Japanese patent application first publication Kokai Hei-6-184126), or by a synthetic process (see PCT International Publication No.WO94/19334), as above-mentioned. PF1022 E substance may also be synthesized from PF1022 substance through a method comprising four step chemical reactions. In the latter 4-step synthetic method, PF1022 E substance can be prepared by the method comprising the first step for nitration of the hydroxyl group at the para-position of the benzene ring of PF1022 substance, the second step for reduction of the nitro group into an amino group, the third step for diazotization of the amino group, and the fourth step for hydrolysis of the diazonium salt. The above first step to the fourth step of this synthetic method are now detailed below.

[The first step]

It is well known that, in general, a mixture of concentrated sulfuric acid (or sulfur trioxide) with concentrated nitric acid, or fuming nitric acid alone, and the like is used as a useful reagent for such nitration of hydrogen atom(s) present on benzene ring, which is effected by electrophilic substitution reaction. However, we have already found that, so far as the nitration of PF1022 substance is concerned, it is difficult to introduce a nitro group into only one of the two benzene rings of PF1022 substance and specially at the para-position of the benzene ring with a high selectivity, because PF1022 substance has the two benzene rings which are chemically equivalent to each other.

We have studied on a variety of reagents and reaction conditions, and thus we have now succeeded in achieving the nitration of the phenolic hydroxyl group present at the para-position of the phenyl group of PF1022 substance by a process comprising dissolving the PF1022 substance in acetic anhydride, followed by reacting it with a stoichiometrically specified amount of fuming nitric acid at a low temperature of −30° C. to −10° C.

[The second step]

In general, the reduction of an aromatic nitro group is carried out by a process comprising catalytic reduction with hydrogen gas or sodium borohydride in the presence of a catalyst such as palladium, platinum, Raney nickel, etc., or by a process comprising chemical reduction with an acid in combination with a metal such as iron, tin, zinc, etc.

For the reduction of the nitro derivative of PF1022 substance as obtained in the above first step, it has been found that either a method of reacting said nitro derivative with hydrogen gas under atmospheric pressure in the presence of 5–10% palladium/carbon in an alcoholic solvent, or method of reacting the nitro derivative with tin and concentrated hydrochloric acid in an inert solvent such as dioxane is able to give the target aminated compound in a high yield from said nitro derivative of PF1022 substance.

[The third and fourth steps]

The aminated compound so obtained in the second step is then reacted with nitrous acid in the same manner as that for the diazonation of usual aromatic amino compounds, to produce the corresponding diazonium salt which is relatively stable. In fact, when the amino compound as obtained in the second step is treated with sodium nitrite or a lower alkyl ester of nitrous acid such as amyl nitrite, in combination with a suitable acid such as hydrochloric acid, sulfuric acid, trifluoroacetic acid, etc., added in the reaction system, nitrous acid is generated in situ, and it is further reacted easily with said amino compound so as to give the diazonium salt intended.

Then, in the fourth step, the resulting diazonium salt compound can be hydrolyzed to yield the PF1022 E substance.

1–2. Syntheses of Various PF1022 Derivatives from PF1022 E Substance (A) When PF1022 E substance is used as the starting compound, certain of the compounds of the general formula (I), e.g. such a compound of formula(I) where $R^1$ is H and $R^2$ is 2-aminoethoxy group, or its similar compound where the hydrogen atom (s) of the amino group in said 2-aminoethoxy group is or are replaced by an alkyl group, is possible to be easily prepared by a process comprising three steps of chemical conversions, namely the process comprising the 1st step for cyanomethyl etherification of the phenolic hydroxyl group of PF1022 E substance, the 2nd step for reduction of the cyanomethyl group into 2-aminoethyl group and the 3rd step for N,N-dialkylation of the 2-amino group of said 2-amimoethyl group. This process is now concretely described for its 1st, 2nd and 3rd steps.

[The 1st step]

The reaction for cyanomethyl etherification of the phenolic hydroxyl group of PF1022 E substance may be carried out by reacting it with a halogenated acetonitrile, such as chloroacetonitrile, bromoacetonitrile and iodoacetonitrile in an inert organic solvent, including ethers such as ethyl ether, isopropyl ether, tetrahydrofuran (THF), 1,4-dioxane, etc., ketones such as acetone, 2-butanone etc., halogenated hydrocarbon solvent such as dichloromethane, chloroform and the like, as well as N,N-dimethylformamide (DMF), dimethylsulfoxide (DMSO) and the like, in the presence of such a base, such as potassium t-butoxide, sodium hydride, potassium carbonate, sodium carbonate, and amines such as triethylamine, 1,8-diazabicyclo[5,4,0]-7-undecene, etc., which acts as a hydrogen halide scavenger. Preferably, this 1st step may be effected by the treatment with bromoacetonitrile, either in the presence of sodium hydride in tetrahydrofuran, or in the presence of potassium carbonate in acetone. Under these conditions, the reaction may proceed satisfactorily at room temperature and can give the desired cyanomethyl ether derivative in a higher yield than those when the reaction is effected under another reaction conditions.

[The 2nd step]

The cyanomethyl ether derivative obtained in the above 1st step can then be converted into the corresponding 2-aminoethyl-ether derivative easily by a catalytic reducing reaction in the presence of a catalyst such as palladium, platinum oxide and the like. As the reaction solvent, a lower alcohol such as methanol, ethanol, etc., is relatively suitable and the reaction may proceed smoothly at room temperature with a hydrogen gas under a medium pressure, to give the desired 2-aminoethyl-ether derivative in a high yield.

[The 3rd step]

The 2-aminoethyl ether derivative obtained in the above 2nd step can then be N,N-dialkylated in an inert organic solvent by a process (1) comprising treating said derivative with an alkyl halide in the presence of a base acting as a hydrogen halide scavenger, or by a process (2) comprising treating said derivative with a lower alkanal under such reduction conditions, either by a catalytic reduction with a catalyst such as palladium, platinum oxid under a medium pressure, or by a chemical reduction with using sodium cyansborohydride or sodium borocyanide. Thereby, said derivative can be converted easily into the desired final compound. When the process (1) above is adopted, it is relatively suitable that DMF or DMSO is used as the solvent and that potassium carbonate is used as the base. For the alkyl halide, an alkyl bromide or iodide is better to be used than an alkyl chloride to achieve a higher yield of the desired product. In case of effecting the process (2), a lower alcohol such as methanol, ethanol etc., is relatively suitable to be used as the reaction solvent. In some instances, the alkylation reaction of the amino group of the aminoethyl ether derivative appears to be promoted by addition of a small amount of an acid such as hydrochloric acid, acetic acid, etc.

The substituent of such a type, which can be introduced in place of the phenolic hydroxyl group of PF1022 E substance, includes ordinary linear or branched alkyl, alkenyl and alkynyl groups, as well as those groups having a variety of substituents. To be concrete, methyl, ethyl, n-propyl, isopropyl, n-butyl, isobutyl, sec-butyl, amyl, hexyl allyl, (2-propenyl) 2-hydroxyethyl, 2-methoxyethyl, benzyl groups, etc. are typical examples of the introducible substituent. Introduction of such a cyclic amino group which contains the nitrogen atom of the amino group as the ring-constituting atom, that is, the cyclic amino group-constituting atom and which may be a morpholino, pyrrolidino or piperidino group, etc., maybe effected in a manner similar to the introduction of the aforesaid dialkyl group. (B)

The syntheses of such a compound of general formula (I), where, for example, R¹ is H and R² is 3-aminopropoxy group, may be carried out by a process comprising condensing PF1022 E substance with a 1-halo-3-aminopropane having the protected amino group to form an ether linkage, so that the desired 3-aminopropyl-ether derivative is yielded. Substituents which are similar to those mentioned in respect to the aforesaid 2-aminoethyl-ether derivative, may be introduced as the N-substituents in the 3-aminopropyl-ether derivative, too.

(C) The syntheses of such a compound of general formula (I), where R¹ is H and R² isaheterocyclicring-substituted methoxy group, may be carried out by a process comprising condensing PF1022 E substance with an appropriate halogenated heterocyclic ring compound of general formula (IV)

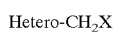
(IV)

wherein Hetero is a heterocyclic ring and X is Cl, Br, I or hydroxyl, with formation of an ether linkage in the same manner as above, whereby a corresponding heterocyclic ring-containing derivative of PF1022 E substance is produced.

The nature of the above group X to be preferred may depend upon the nature of the heterocyclic ring present in the compound (IV). In case where X=halogen, PF1022 E substance may usually be reacted with a halogenated compound of the formula (IV) in the presence of a base acting as a hydrogen halide scavenger in an inert solvent. When X=Cl or Br, the addition of a metal iodide to the reaction mixture may generally promote the reaction more smoothly. As the solvent to be used here, there may be mentioned ethers such as ethylether, isopropylether, tetrahydrofuran (THF), 1,4-dioxane etc.; ketones such as acetone, 2-butanone, etc.; halogenated solvent such as dichloromethane, chloroform, etc. as well as other solvent such as N,N-dimethylformamide (DMF), dimethylsulfoxide (DMSO) and the like. As the base to be used, there may be mentioned potassium t-butoxide, sodium hydride, potassium carbonate, sodium carbonate cesium carbonate etc.; organic base such as triethylamine, 1,8-diazabicyclo[5.4.0]-7-undecene, etc. The reaction temperature to be suitable may depend upon the nature of the heterocyclic derivative as used, as well as the solvent and base to be used. In most cases, good results may be obtained by effecting the reaction at room temperature to 90° C.

In case where X is hydroxyl group in the compound of general formula (IV), the product as intended may easily be obtained by so-called "Mitsunobu" reaction between PF1022 E substance and the compound (IV). To be concrete, the reaction is effected by contacting PF1022 E substance with a condensation reagent consisting of a diazodicarboxylic acid derivative such as ethyl ester of diazocarboxylic acid, azodicarbonyldipiperidine, etc., and a trivalent phosphorus compound such as triphenylphosphine, tributylphosphine, etc., in an inert solvent. As the solvent to be used, THF and the like are typically available.

Incidentally, it should be noted that when an active hydrogen atom which would inhibit the etherification reaction in question is existing in the heterocyclic ring moiety of the halide compound of general formula (IV), previous introduction of an easily cleavable protecting group is necessary for blocking the active hydrogen atom.

When the heterocyclic ring of the halide compound of general formula (IV) is 2-imidazolyl or 2-thiazolyl group, an alternative method may be used. Thus, this alternative method comprises reacting the aforesaid cyanomethyl ether derivative first with O,O'-diethyl dithiophosphate in an aqueous mixed solvent, for example, in a mixture of water-chloroform-toluene, under heating to reflux, thereby to obtain a thiocarbamoylmethyl ether derivative. Then, this thiocarbamoylmethyl ether derivative is reacted with bromoacetaldehyde diethylacetal in an aromatic hydrocarbon solvent such as benzene, toluene, xylene, etc., in the presence of an acid catalyst such as concentrated sulfuric acid, etc., at 70–100° C., thereby to yield a 2-thiazolyl derivative. In a similar manner, said thiocarbamoylmethyl ether derivative may be reacted with methyl iodide in, for example, acetone, and the resulting product is then reacted with aminoacetaldehyde dimethylacetal in an aromatic hydrocarbon solvent such as benzene, toluene, xylene, etc., in the presence of hydrochloric acid at 70–100° C., thereby to yield a 2-imidazolyl derivative.

(D) The compound of general formula (I), where R¹ is hydrogen atom and R² is t-butoxy group, may be prepared by reacting PF1022 E substance with isobutene in the presence of an acid catalyst to O-t-butylate the hydroxyl group of PF1022 E substance so as to give the t-butyl ether derivative.

2. A Process Comprising a Chemical Conversion of PF1022 H Substance

Compounds of general formula (I), where both of R¹ and R² each stand for a cyano-($C_1$–$C_6$)alkoxy group, thiocarbamoyl-($C_1$–$C_6$)alkoxy group, amino-($C_1$–$C_6$)alkoxy group, amino-($C_1$–$C_6$) alkoxy group having an amino-protecting group, N-mono-($C_1$–$C_6$)alkylamino-($C_1$–$C_6$) alkoxy group, N,N-di-($C_1$–$C_6$)alkylamino-($C_1$–$C_6$)alkoxy group, N,N-di-(($C_1$–$C_6$)alkoxy($C_1$–$C_6$)alkyl)amino-($C_1$–$C_6$) alkoxy group, or a cyclic amino-($C_1$–$C_6$) alkoxy group of which the cyclic amino group is a 5- or 6-membered ring containing one or more nitrogen atoms and further optionally containing oxygen atom or sulfur atom as the cyclic amino group-constituting atoms, may be prepared by starting from the compound of general formula (I) where both R¹ and R² are hydroxyl group, namely PF1022 H substance.

PF1022 H substance hitherto could be prepared only by a totally synthetic process(see PCT International publication No. WO93/19053) or by a syntheses from PF1022 substance (see PCT International publications No. WO93/19053 and WO94/19334). It has now been found, however, that PF1022 H substance is contained in a culture broth of the fermentation of the PF1022 substance-producing microorganism (see Japanese patent application No. Hei-8-208201). The chemical structure of PF1022 H substance corresponds to such structure that PF1022 substance has been modified to render its two benzene rings substituted by hydroxyl substituents at the para-positions. Thus, it is possible to synthesize various derivatives from PF1022 H substance by simply applying to PF1022 H substance such chemical modification methods which are just as described hereinbefore practiced for the PF1022 E substance having such structure that one hydroxyl group only has been substituted at the para-position of one benzene ring of PF1022 substance. It is also possible to apply to PF1022 H substance any other chemical reactions which are applicable to a usual phenolic hydroxyl group. Their typical chemical reactions of this kind include acylation (esterification of carboxylic acids), etherification and the like. For example, reaction of PF1022 H substance with isobutene in presence of an acid catalyst will result in O-t-butylation of both the two phenolic hydroxyl groups of PF1022 H substance to give the corresponding alkyl ether derivative.

3. A Process Comprising Formation of Carboxylated Derivative by Reaction at the Hydrogen Atom(s) of the Benzene Ring(s) of PF1022 Substance Such compounds of general formula (I), where either one of $R^1$ and $R^2$, or both of $R^1$ and $R^2$ is or are a ($C_3$–$C_6$) alkanoyl group optionally substituted by a halogen atom or hydroxyl group, or an N-mono-($C_1$–$C_6$)alkylcarbamoyl group, N,N-di-($C_1$–$C_6$) alkylcarbamoyl group or a cyclic amino-carbonyl group of which the cyclic amino group is 5- or 6-membered ring containing one or more nitrogen atoms and further optionally containing oxygen atom or sulfur atom as the cyclic amino group-constituting atoms, or an N-mono-($C_1$–$C_6$)alkylamino ($C_1$–$C_6$)alkoxycarbonyl group, an N,N-di-($C_1$–$C_6$)alkylamino-alkoxycarbonyl group, or a cyclic amino-($C_1$–$C_6$)alkoxycarbonyl group of which the cyclic amino group is a 5- or 6-membered ring containing one or more nitrogen atoms and further optionally containing oxygen or sulfur atom as the cyclic amino group-forming atoms, or a formyloxy-($C_1$–$C_6$)alkylcarbonyl group, as well as such compounds of general formula (I), where either one of $R^1$ or $R^2$, or both of $R^1$ and $R^2$ is or are a carboxyl group, t-butyl group, or 2-amino-thiazolyl group, may be prepared by two methods as described below, i.e. a method (1) of conducting chemical conversion with starting from PF1022 substance, and a method (2) of conducting total syntheses.

The method (1) of conducting chemical conversion of PF1022 substance includes four processes (a) to (d), which are process (a) comprising acylation of the benzene rings of PF1022 substance, particularly comprising acetylation; process (b) comprising chemical conversion of the acetyl derivative belonging to the acyl derivative as obtained by the process (a), into a carboxyl derivative; process (c) comprising synthesis of derivative of PF1022 substance from said carboxyl derivative; and process (d) comprising synthesis of new derivatives of PF1022 substance from the nitro derivative of PF1022 substance.

Method (1) of Conducting Chemical Conversion of PF1022 Substance Includes the Processes (a) to (d) which are now Described in Details.

The process (a) comprising acylation of benzene rings of PF1022 substance:

A variety of electrophilic substitution reactions which are well-known for the acylation of ordinary aromatic compounds, can be applied to acylation of both the two benzene rings of PF1022 substance. By utilizing those known reactions, various types of derivatives of PF1022 substance may be synthesized.

Many examples are hitherto known for that a hetero atom such as oxygen, nitrogen and others is bonded to the benzene rings of PF1022 substance. Nonetheless, there is not yet known such derivatives which would have been derived by forming a further new carbon-carbon linkage on the benzene ring(s) of PF1022 substance. In order to prepare such new compounds having the carbon-carbon linkage(s) on the benzene ring(s) of PF1022 substance, Friedel-Crafts reaction well provides a very effective measure. Thus, usual method for Friedel-Crafts reaction can apply to the acylation of the benzene ring(s) of PF1022 substance. That is, in order to achieve said acylation of PF1022 substance, reaction may be carried out by treating PF1022 substance with an acylating agent such as carboxylic acid chloride, carboxylic anhydride, etc., in an inert solvent such as nitrobenzene, carbon tetrachloride, carbon disulfide, etc., and, if necessary, in the presence as an activating agent of Lewis acid, typically aluminum chloride.

For example, when acetyl group is to be introduced into the benzene ring of PF1022 substance, the above-mentioned inert solvent may be used. However, a better result may be given by carrying out the reaction by treating PF1022 substance with acetyl chloride as both the solvent and the acylating reagent in the presence of aluminum chloride. This acetylation reaction can mainly produce both the ortho-substituted derivative and para-substituted derivative, and these derivatives can be isolated from each other and purified by chromatographic treatment.

When pivaloyl chloride is used as the carboxylic acid chloride, no acylation reaction occurs but there is formed such a derivative of PF1022 substance in which hydrogen atom(s) on the benzene ring(s) of PF1022 substance has (have) been substituted by t-butyl group.

The process (b) comprising chemical conversion of the acetyl derivative, one of the acyl derivatives as obtained by the process (a), into a corresponding carboxyl derivative:

The acetyl derivative as obtained by the above process (a) may be subjected to the following four reaction steps in order to prepare the corresponding carboxyl derivative therefrom, with the intention of further providing various another derivatives thereof.

Thus, of the above four reaction steps, the first step is to prepare the corresponding bromoacetyl derivative by reacting said acetyl derivative with a brominating agent such as N-bromosuccinimide, pyridinium perbromide, bromine, etc. in an inert halogenated solvent such as carbon tetrachloride, chloroform, etc. A particularly preferred example of such reaction is a reaction of the acetyl derivative with a stoichiometric amount of bromine in chloroform in the presence of a catalytic amount of hydrogen bromide, by which the desired product can be obtained in a high yield. The second step is to prepare the corresponding formyloxyacetyl derivative by-treating said bromoacetyl derivative with sodium formate in formic acid. The third step is to effect methanolysis of the formyloxyacetyl derivative so as to give the de-formylated derivative, i.e. the hydroxyacetyl derivative. The fourth step i.e. the final step is to treat the hydroxyacetyl derivative with an oxidizing agent such as sodium periodate, lead tetraacetate, periodic acid, etc., preferably sodium periodate, so as to prepare the carboxyl derivative intended.

Besides, the above-mentioned bromoacetyl derivative may be reacted with thiourea in an inert solvent, preferably in an ether solvent such as tetrahydrofuran and dioxane in the presence of a base such as sodium hydrogen carbonate, sodium carbonate, and the like, so that a 2-aminothiazole ring is formed, whereby a compound having 2-aminothiazole ring(s) at para-position(s) of the benzene ring(s) may be prepared.

The process (c) comprising synthesis of derivatives of PF1022 substance from the corresponding carboxyl derivative:

The carboxyl derivative as obtained by the above process (b) may then be subjected to such a chemical conversion which is conventionally applicable to the carboxyl group, and thereby it is possible to prepare new derivatives of PF1022 substance. Such chemical conversion may include esterification, amidation and the like which may be practiced in a well-known manner.

The process (d) comprising synthesis of derivatives of PF1022 substance from the nitro derivative of PF1022 substance:

In addition to Friedel-Crafts reaction as above-mentioned, it is feasible to utilize Sandmeyer reaction as the carbon-carbon linkage-forming reaction for the introduction of carboxyl group(s) into PF1022 substance on its benzene ring(s).

To be concrete, for this purpose, PF1022 substance maybe first nitrated, followed by reducing the nitro group(s) of the nitration product to give the corresponding amino derivative. This amino derivative is then treated with nitrous acid, thereby to prepare the corresponding diazonium salt on one or both of the benzene rings of PF1022 substance (see PCT international Publication No. WO93/19033). By finally reacting the diazonium salt with a metal cyanide, it is possible to prepare the corresponding cyano compound wherein the cyano group(s) is or are introduced on the benzene ring(s) of PF1022 substance.

The compound so prepared, which has the cyano group(s) on the benzene ring(s) of PF1022 substance, can further be treated by a direct application of any conventional process for the chemical conversion which is applicable to aromatic nitrile compounds. Thus, it is possible that the carboxyl derivative can be prepared efficiently from the corresponding cyano derivative of PF1022 substance.

An advantage of this process over the aforesaid process of utilizing Friedel-Crafts reaction is in that the former process can introduce the cyano group(s) just at the position where the nitro group (s) has (have) been bonded to the benzene ring, and thereby it is possible to avoid the by-formation of regio-isomer(s) which can be involved in the latter Friedel-Crafts process.

Method (2) of conducting total syntheses is described below.

Compounds of general formula (I) of the different type mentioned in the above may also be synthesized by a totally synthetic process with starting from such an L-phenyllactic acid derivative of which the hydrogen atom(s) on the benzene ring(s) of the phenyl group has(have) been substituted by carboxyl group(s).

It may be possible as one practicable method that Friedel-Crafts reaction is applied to the above L-phenyllactic acid derivative similarly to the aforesaid process. However, it is rather meritable to utilize such a starting material which have born a functional group convertible into carboxyl group just at the position of the phenyl group to be desired for a next formation of the carboxyl group. For example, p-amino-L-phenylalanine or p-nitro-L-phenylalanine commercially available is meritably used as the starting material, when a p-substituted derivative of PF1022 substance is to be synthesized as a target product. This is because there is obtained such advantage that the p-carboxyl-L-phenylalanine derivative can be prepared without possibility of the by-formation of other regio-isomer(s) and without any necessity for further working of the purification and isolation of the p-carboxyl-L-phenylalanine derivative as just prepared.

When p-amino-L-phenylalanine mentioned above is used as the starting material, only one of the two amino groups of this alanine compound is required to be reacted, and therefore, first of all, the other amino group has to be selectively protected with an appropriate amino-protecting group. It is then necessary that the protecting group once introduced must be removed from the product at a later stage. In contrast thereto, when p-nitro-L-phenylalanine is used as the starting material, it is possible to take such procedures wherein the a-amino group of this alanine compound is converted into diazonium salt by a conventional means, followed by converting the group of diazonium salt into hydroxyl group to give the p-nitro-L-phenylactic acid, then reducing the nitro group of the latter compound into amino group, and finally converting the amino group into carboxyl group. The latter process is believed to be superior to the former process, because the p-carboxy-L-phenyllactic acid derivative as desired can be prepared without using any amino-protecting group.

The latter-mentioned process starting from p-nitro-L-phenyl alanine is concretely explained below. That is, p-nitro-L-phenylalanine is first treated with a metal nitrite or an alkyl nitrite in an aqueous acidic solution in order to produce the above-mentioned diazonium salt. As said aqueous acidic solution, the aqueous solution of hydrochloric acid, sulfuric acid, acetic acid, etc., is suitable. Acetic acid is preferred. As the usable metal nitrite, there may be mentioned potassium nitrite, sodium nitrite, etc., As the usable alkyl nitrite, there may be mentioned isoamyl nitrite, butyl nitrite, etc. Sodium nitrite is particularly preferred. For sake of easier handling or processing, the p-nitro-L-phenyllactic acid so obtained is then esterified with hydrogen chloride-methanol, hydrogen chloride-ethanol, diphenyldiazomethane, etc., to produce a p-nitro-L-phenyllactate(the ester). The p-nitro group of the resulting ester product is then further converted in diazonium salt in the same manner as in the above-mentioned Sandmeyers process. The diazonium salt thus formed is treated with a metal cyanide to give a p-cyano-L-phenyllactate. As the metal cyanide, there may be used sodium cyanide, potassium cyanide, copper cyanide, etc. Copper cyanide is preferred for attainable higher yield of the desired product. Further, the cyano group of the p-cyano-L-phenyllactate may then be converted into carboxyl group, carboxylic acid ester group, carboxylic amido group, and others, by treating with any known means which is applicable to the usual aromatic cyano group.

By uilizing the so produced derivative of L-phenyl-lactic acid as one of the starting materials, it is feasible to prepare the novel PF1022 derivative according to this invention by totally synthetic processes.

(II) Now, the processes for preparation of the derivatives of PF1022 substance having general formula (III) according to this invention are described.

1. Process comprising the oxidative decomposition (conversion of phenyl group into carbonyl group) of the benzene ring moieties of PF1022 substance and subsequent formation of a compound in which the original benzene ring has been replaced by a heterocyclic ring.

Compound of general formula (III) according to this invention may be produced by firstly preparing Cyclo[MeLeu-Lac-MeLeu-(HOCO)Lac-MeLeu-Lac-MeLeu-PhLac] or Cyclo[Meleu-Lac-MeLeu-(HOCO)Lac-MeLeu-Lac-MeLeu-(HOCO)Lac] having 24-membered ring which is derived by replacement of one or two of the phenyllactic acid residues of PF1022 substance by malic acid residue or residues, and using the so prepared compound as the starting material.

The starting compound as above may be prepared by two different processes, that is, a first process (1) comprising producing the 24-membered ring by a totally synthetic process with using a malic acid derivative having proper protecting group(s) as one of starting materials (see PCT international publication No. WO94/19334), followed by removing the protecting group(s), to give the desired compound; and a second process (2) comprising using PF1022 substance as the starting material, and oxidatively decomposing the benzene ring moieties of PF1022 substance with ruthenium tetraoxide.

In the process (2) just above, it is effective to adopt such a method wherein an "in situ" formation of ruthenium tetraoxide is effected by using a suitable co-oxidizing agent in the presence of a catalytic amount of a ruthenium compound such as ruthenium dioxide, ruthenium trioxide, and the like.

In this method, it is also possible that only one of the two benzene rings of PF1022 substance is converted into carboxyl group, when the amount of co-oxidizing agent used is limited to the stoichiometric amount. As examples of the usable co-oxidizing agent, there may be mentioned salts of halogen oxides such as sodium periodate, potassium periodate, potassium bromate, sodium hypochlorite, potassium perchlorate, etc., as well as periodic acid compounds such as periodic acid hydrate, and heavy metal oxides such as potassium permanganate, potassium dichromate, etc., salts thereof, and also organic base oxides such as N-methylmorpholine-N-oxide, etc., per-acids such as m-chloro-perbenzoic acid, peracetic acid, etc., or per-oxides such as aqueous hydrogen peroxide, t-butylhydroperoxide, and the like. The use of periodic acid hydrate or sodium periodate is preferred.

The mono- and di-carboxylic acid derivatives obtained by the oxidative decomposition of PF1022 substance as above are able to undergo almost all of the chemical reactions which are applicable to carboxyl group, but provided that the reaction conditions used do not decompose the basic skeleton of the cyclodepsipeptide. Typical examples of such chemical reactions may include reactions for synthesis of acid halide or mixed acid anhydrides, reactions for formation of esters with various alcohols, reactions for amidation with various amines, reactions for formation of ortho-esters, and reactions for reduction into aldehydes and alcohols, as well as reactions for formation of hetero cyclic-rings as described below by reaction with 1,2- and 1,3-diamines, amino-alcohols, amino-thiols, and the like. The resulting substances so formed by the above conversions are able to further be converted to into another derivatives.

The mono- and di-carboxylic acid compounds so prepared by the above-mentioned processes are the Cyclo [MeLeu-Lac-MeLeu-(HOCO)Lac-MeLeu-lac-MeLeu-PhLac] or Cyclo[Meleu-Lac-MeLeu-(HOCO)Lac-MeLeu-Lac-MeLeu-(HOCO)Lac]. When these compounds are used as a starting material, such compounds of general formula (III), which are a mono- or bis-heterocyclic derivative of PF1022 substance and in which one or two benzene rings of the parent PF1022 substance has or have been replaced by heterocyclic ring(s), may be synthesized by the following two different routes.

Thus, the two routes include (1) a one step-process comprising the reaction with a 1,2-di-substituted diamine, amino-alcohol, or amino-thiol, etc., with involving the ring formation while dehydration is effected, as well as (2) a two-step process comprising the reaction with a diamine, amino-alcohol, or amino-thiol, etc., with involving dehydration as above and giving the corresponding amide, ester, thioester etc., and the subsequent treatment of the product for its ring formation reaction so as to give the target compound.

Examples of measures for the dehydration used in both the processes (1) and (2) just above include a method of using a dehydrating agent, which may by, for example a compound as prepared upon its use from trifluoromethanesulfonic acid anhydride and triphenylphosphine as known in literature (J. Org. Chem., 52, 4137, 1987), or a carbodiimide such as dicyclohexylcarbodiimide, or molecular sieves, etc., as well as a method of treating the aforesaid mono- or di-carboxylic acid compound under refluxing in the presence of an acid catalyst such as p-toluenesulfonic acid or the like in an apparatus such as Dean-Stark device, with using a solvent such as benzene, toluene and xylene which is capable of forming an azeotropic mixture with water.

(III) The processes for preparation of PF1022 derivatives of general formula (II) according to this invention are described below.

(a) Such a compound of general formula (II), where $R^3$ is a hydrogen atom and $R^4$ is a morpholino group attached to any of the ortho-, meta- and para-positions of the phenyl group shown in the formula (II), may preferably be prepared by the under-mentioned process comprising using, as starting material, the compound of formula Cyclo[MeLeu-Lac-MeLeu-($H_2$N)PhLac-MeLeu-Lac-MeLeu-PhLac] in which an amino group has been introduced into the para-position of one of the benzene rings of PF1022 substance and which was synthesized by the process described hereinbefore.

Illustratively, said compound, Cyclo[MeLeu-Lac-MeLeu-($H_2$N)PhLac-MeLeu-Lac-MeLeu-PhLac] may be reacted with a di-(2-haloethyl)ether in an inert solvent in the presence of a base, whereby cyclization can easily occur at the amino group moiety with conversion of the amino group into the morpholino group, to afford the morpholino derivative.

As the di-(2-haloethyl)ether, di-(2-chloroethyl) ether and di-(2-bromo-ethyl)ether are effective. The latter ether is preferred in view of attainable more smooth progress of the reaction. Addition of an iodide such as sodium iodide, potassium iodide, tetra-(n-butyl)ammonium iodide, etc., to the reaction mixture can achieve a higher yield of the morpholino derivative to be produced.

(b) Such a compound of general formula (II), where $R^3$ is a morpholino group attached to any of the ortho-, meta- and para-positions of the phenyl group shown in the formula (II) and $R^4$ is a morpholino group attached to the ortho- or meta-position of the phenyl group, may be synthesized by a process which comprises treating PF1022 substance with an excess amount of a nitrating agent such as a mixture of concentrated sulfuric acid (or sulfur trioxide) with concentrated nitric acid, fuming nitric acid singly, or the like, to give a mixture of regio-isomers of the di-nitro compounds where one nitro group has been introduced into each of the two benzene rings of PF1022 substance, and subsequently subjecting the resulting di-nitro compound to the chemical conversion in the same manner as for the aforesaid mono-nitro derivative, so as to produce such di-morpholino derivative where one morpholino group has been attached to each of the two benzene rings of PF1022 substance. In this process, too, each of the regio-isomers as produced may be isolated from the other and further purified whenever either at the stage of the intermediate nitro compounds or at the stage of the morpholino compounds obtained as the final product.

Further, in the different processes explained hereinbefore, the protecting group, which is used for the protection of the amino groups present in the starting materials and the intermediate compounds, may be any amino-protecting group which is removable under acid hydrolysis or reduction conditions, for example, benzyloxycarbonyl (Cbz) group, t-butoxycarbonyl(Boc) group, p-methoxybenzyl-oxycarbonyl group, formyl group, and the like, as well as any amino-protecting group which is conventionally used in peptides chemistry and which is removable under neutral conditions, for example, allyloxycarbonyl group, and the like. Preferred amino-protecting groups are t-butoxycarbonyl (Boc) group and benzyloxycarbonyl (Cbz) group. The introduction of the Boc group may be carried out by using a commercially available reagent such as DiBoc reagent, Boc-ON reagent, etc. The introduction of the Cbz group may be effected by Cbz chloride reagent, N-Cbz succinimide reagent, etc. For the both cases, the protection reaction may be done in an inert solvent such as THF, 1,4-dioxane, DMF, etc., and in the presence of an inorganic or organic base. Usually, the Boc group as the amino-protecting group can easily be removed by treating it with an acid such as hydrochloric acid, trifluoroacetic acid, etc., and the Cbz group can easily be removed by catalytic hydrogenation.

Further, the usable carboxyl-protecting group, which is introduced in the starting materials and the intermediate compounds, includes such carboxyl-protecting group which is removable under acid hydrolysis conditions or reducing conditions, for example, t-butyl, diphenylmethyl, benzyl, p-methoxybenzyl, or trityl group and the like, as well as such carboxyl-protecting group which is removable under neutral conditions, for example, allyl group, etc. The carboxyl-protecting group which is removable under acid hydrolysis conditions may be removed by treating with trifluoroacetic acid, methanesulfonic acid, trifluoromethanesulfonic acid or the like. The treatment with trifluoroacetic acid is most preferred to this end. When the carboxyl-protecting group used is such one which is removable under the reducing conditions, this carboxyl-protecting group is preferable to be removed by treating by catalytic reduction in the presence of palladium. The carboxyl-protecting group which is removable under neutral conditions, such as allyl group, may be removed by a method of reacting it with potassium 2-ethylhexanoate in the presence of zero-valent palladium as a catalyst.

The new cyclodepsipeptide derivatives of PF1022 substance according to this invention which are produced as above are able to form acid addition salts with pharmaceutically acceptable inorganic acid, such as hydrochloric acid, sulfuric acid and phosphoric acid, or with pharmaceutically acceptable organic acid, such as acetic acid, propionic acid, citric acid and methanesulfonic acid. Further, the new PF1022 derivatives according to this invention or their salts may be formulated into anthelmintic compositions by mixing with a solid or liquid carrier which is pharmaceutically acceptable.

According to a fourth aspect of this invention, therefore, there is provided a vermicidal or anthelmintic composition comprising as an active ingredient at least one of the new cyclodepsipeptide derivatives of PF1022 substance represented by the above mentioned general formulae (I), (II) and (III), and their salts.

The new cyclodepsipeptide derivatives of the general formulae (I), (II) and (III) or salts thereof, or the compositions containing the same according to this invention may be orally or parenterally administered to animals. The dose of the active ingredient may suitably be determined by preliminary tests, depending upon the nature of parasite to be expelled, nature of host animals in which parasites are living, and other several factors. For instance, in case when roundworms living in chickens are to be expelled by oral administration of the active ingredient, it is shown, as a general guide, that the new compound of this invention according to the general formula (I), (II) or (III) may be orally given the dosage of at least 0.05 mg/kg, preferably of 0.2–3 mg/kg in order to achieve effective elimination of the parasite.

The compound of general formulae (I), (II) or (III) according to this invention may be formulated into a vermicidal or anthelmintic composition in the same manner as for the composition of PF1022 substance which is described in Japanese patent application first publication Kokai No. Hei-3-35796 or European patent application Publication No. 0382173A2.

As host animals to which the novel cyclodepsipeptide derivatives of PF1022 substance according to this invention may be given as anthelmintic agents, there are exemplified stock animals, poultry, experimental animals and companion animals, such as swine, cattle, rabbits, sheep, goats, domestic fowls, turkeys, mice, white rats, guinea pigs, monkeys, dogs, cats, horses, small birds, and others. Illustrative parasites which are living on these host animals, include parasites on cattle, such as twisted stomachworms, stomachworms belonging to the genus Ostertagia, small hairworms, nematodes belonging to the genus Cooperia, nodularworms belonging to the genus Oesophagostomum, amphisomes, intestinal tapeworms (*Moniezia benedeni*), lung worms and liver flukes; parasites in swine, such as, roundworms, whopworms and nodularworms; parasites on dogs, such as roundworms, hookworms, whipworms and heart worms; parasites in cats, such as roundworms and *Spirometra mansoni*; and parasites in chickens, such as roundworms, hairworms and cedal worms. The compounds of this invention are also effective for the elimination of parasites in human bodies, such as roundworms, pinworms, hookworms (*Ancyclostoma duodenale, Ancylostoma ceylanicum, Necator americanus*), oriental hairworms, strongyloides worms and whipworms.

The novel cyclodepsipeptide derivatives of PF1022 substance according to this invention are utilizable for the treatment and prevention of parasitic infections. For the purpose of the treatment, the compounds may be administered orally and parenterally. For oral administration, there are available various methods of administration, including such a method wherein a liquid preparation of the compound is forcedly administered using an implement such as stomach catheter, such a method wherein the compound is mixed in a daily feed or drinking water and the resulting mixture is administered, or such a method wherein the compound is administered in the form of any appropriate preparation for usual oral administration, such as tablets, capsules, pellets, boluses, powders, soft capsules, etc.

Upon parenteral administration, the compounds of this invention may be administered by injections, e.g., subcutaneously, intramusculary, intravenously, intraperitoneally, etc., in the form of a water-insoluble preparation comprising peanut oil, soybean oil, etc. or in the form of a water-soluble preparation comprising glycerol, polyethyleneglycol, etc. In such parenteral preparations, the compound of this invention may, in general, be contained in an amount of 0.1–10% by weight on the weight basis of the composition.

For the purpose of the preventive treatment of parasitic infections, it is a common practice to administer the compound of this invention orally in the form of a mixture of the compound with any daily feed. No limitation is imposed on the administration period in cases of the preventive purposes. However, it is, in most cases, sufficient to administer the compound of this invention for about two months in the case of tresting broiler chickens, and for about five months in the case of treating swine. The concentration of the compound to be administered may be at least 1 ppm and preferably up to 5–10 ppm of the compound in the feed in which the compound is mixed. The administration may preferably be done continuously.

As regards the safety of the novel cyclodepsipeptide derivatives of PF1022 substance according to this invention, some tests have showed that they are of low toxicity to such extent that mice having received a typical derivative of this invention at dose of 300 mg/kg did not show any abnormality, but showed an ordinary increase in body weight.

Results of animal tests for evaluating the anthelmintic activity of the novel cyclodepsipeptide derivatives of PF1022 substance according to this invention have proved that the compounds of this invention possess strong anthelmintic activity equal to or higher than those of the known derivatives of PF1022 substance which are already disclosed in the literature and patent specifications. Moreover, it is to be noted that the novel PF1022 derivatives of this invention can efficiently be synthesized with starting from PF1022 substance and homologues thereof which are the fermentation products.

Next, the anthelmintic activity of the cyclodepsipeptides of this invention is illustrated by Test Examples.

TEST EXAMPLE 1

"in vivo" Test on Anthelmintic Activity Against Sheep Parasites

To sheep on which a nematode, *Haemonchus contortus* has been infested, a test compounds formulated in the form of gelatine capsules was orally administered at its dose (mg) which was accurately calculated on the basis of the body weight (kg) of the tested sheep.

The number of eggs, which were excreted along with feces from the sheep under test, was counted quantitatively both before and after the administration of the test compound. Thus, the extent of the anthelmintic effects of the test compound was evaluated. The test results are shown in Table 1 below, wherein the tested compounds are indicated by the code number of each substance tested. In Table 1, there is shown the dosage of test compound at which involvement of the excretion of eggs could not be observed at all, that is to say, the dosage of each novel cyclodespsipeptide derivative of PF1022 substance according to this invention at which the parasite could be expelled or exterminated completely. From the above tests, the novel PF1022 derivatives of this invention have been demonstrated to have very much high anthelmintic activity which is 2.5–25 times higher than that of PF1022 substance and 2–5 times higher than that of such a known compound similar to PF1022 substance, which is Cyclo[MeLeu-(Mor)PhLac-MeLeu-Lac] disclosed in PCT International Publication No. WO93/19035.

TABLE 1

| Test substance (Example No.) | Adminstration dose (mg/kg) |
|---|---|
| PF1022 substance (Reference compound A) | 0.25 |
| Cyclo[MeLeu-(Mor)PhLac-MeLeu-Lac] (Reference compound B) | 0.05 |
| PG1022-235 substance (Example 7) | 0.1 |
| PG1022-236 substance (Example 8) | 0.01 |
| PG1022-238 substance (Example 11) | 0.01 |
| PG1022-239 substance (Example 12) | 0.025 |
| PG1022-263 substance (Example 37) | 0.01 |
| PG1022-285 substance (Example 14) | 0.1 |
| PG1022-304 substance (Example 17) | 0.05 |
| PG1022-312 substance (Example 24) | 0.05 |
| PG1022-242 substance (Example 45) | 0.01 |
| PG1022-037 substance (Example 70) | 0.1 |
| PG1022-045 substance (Example 48) | 0.1 |
| PG1022-046 substance (Example 48) | 0.1 |
| PG1022-233 substance (Example 65) | 0.05 |
| PG1022-222 substance (Example 68) | 0.05 |

TEST EXAMPLE 2

"in vivo" Test on Anthelmintic Activity Against *Nipostrongylus brasiliensis*

Male rats of Wister strain, which have been artificially infected with *Nippostrongylus brasiliensis*, were used as test animals. The administration dose (mg) of each test compound was accurately calculated on the basis of the body weight (kg) of each rat. Each compound tested was used in the form of a solution in dimethlsulfoxide or methanol. The solution was diluted with a Ringer solution and forcedly administered orally to the test rats. Ten days after the administration, the rats were dissected and the number of adult parasites remaining in the small intestines of the rats was counted. Efficacy was calculated in comparison with the number of adult parasites in the control group of test rats (infected, but untreated) and is shown in Table 2 below.

The novel PF1022 derivatives tested of this invention were demonstrated to possess a high anthelmintic activity which is 2–10 times higher than that of PF1022 substance (Reference compound A).

TABLE 2

| Test compound (Example No.) | Dosage (mg/kg) | Efficacy (%) |
|---|---|---|
| PF1022 substance (Reference compound A) | 10 | 80.2 |
| PF1022-233 substance (Example 65) | 5 | 100 |
|  | 2 | 100 |
|  | 1 | 99.1 |
| PF1022-270 substance (Example 9) | 5 | 99.7 |
|  | 2 | 94.2 |
| PF1022-271 substance (Example 10) | 5 | 100 |
| PF1022-280 substance (Example 66) | 5 | 100 |
|  | 2 | 99.3 |
|  | 1 | 95.8 |

The examples of the preparation of the novel derivatives of PF1022 substance of general formulae (I), (II) or (III) according to this invention are now concretely illustrated with reference to the following Examples 4–72. In the Examples, the following abbreviations are used with the meanings as indicated shown below.

Boc: t-butoxycarbonyl group

Cbz: benzyloxycarbonyl group

Mor: morpholino group

Pyr: pyrrolidino group bonded at its 1-N-position

Pip: piperidino group bonded at its 1-N-position

BHT: benzothiazolyl group bonded at its 2-position

ATH: aminothiazolyl group bonded at its 4-position

BIM: benzimidazolyl group bonded at its 2-position

Me: methyl group

Pr: n-propyl group

Bu: n-butyl group

Lac: D-lactic acid residue of formula

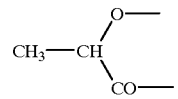

PhLac: D-phenyllactic acid residue of formula

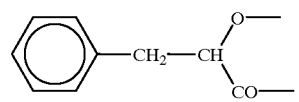

(R)Lac: D-lactic acid residue whose methyl group was substituted by a group —R (R)PhLac: D-phenyllactic acid residue whose phenyl group was substituted by a group —R at the para-position phenyl group (o-R)PhLac: D-phenyllactic acid residue whose benzene ring was substituted by a group —R at the ortho-position of the benzene ring MeLeu: N-methyl-L-leucine residue of formula

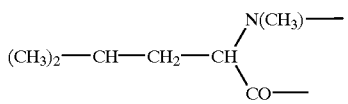

THF: tetrahydrofuran
DMF: N,N-dimethylformamide
DMSO: dimethylsulfoxide
DEAD: diethyl azodicarboxylate
TFA: trifluoroacetic acid
DiBoc reagent: di-t-butyl dicarbonate
HOBt: 1-N-hydroxybenzotriazole
BOP-Cl: bis(2-oxo-3-oxazolidinyl)phosphinic acid chloride Example 1 given below is an example of the preparation of the nitro derivative of PF1022 substance by nitration of the latter; Example 2 given below is an example of the preparation of the corresponding amino derivative by reduction of the nitro group of said nitro derivative; and Example 3 is an example of the syntheses of PF1022 E substance by chemical conversion of the amino group of said amino derivative.

EXAMPLE 1

Preparation of Cyclo[MeLeu-Lac-MeLeu-($O_2N$)PhLac-MeLeu-Lac-MeLeu-PhLac]

PF1022 substance (50 g) was dissolved in acetic anhydride (250 ml), and the resulting solution was maintained below 10° C. under ice-cooling, to which fuming nitric acid (25 ml) was added dropwise. The resulting mixture was stirred for 3 hours for the reaction. The reaction solution obtained was diluted with ethyl acetate (2.5 litres), washed with water, an aqueous saturated sodium hydrogen carbonate solution and water (2.5 litres, each), successively, and was dried over anhydrous sodium sulfate and further evaporated under a reduced pressure to remove the solvent. The resultant residue was purified by a silica gel column chromatography (eluted with ethyl acetate-hexane 1:1, v/v), thus to afford the titled compound (18.6 g; yield 35.5 %) as white powder.

NMR($CDCl_3$): $\delta$=0.78–1.00(24H,m, $\delta$-$CH_3$(MeLeu)), 1.10–1.86(18H,m, $\beta$-$CH_3$(Lac), $\beta$-$CH_2$, $\gamma$-CH(MeLeu)), 2.70–3.25(16H,m,N—Me, $\beta$-$CH_2$(($O_2N$)PhLac,PhLac)), 4.45–5.75(8H,m, $\alpha$-CH), 7.15–7.25(5H,m,aromatic (PhLac)), 7.45, 8.15(each 2H, each d,J=8 Hz,aromatic (($O_2N$)PhLac)).

EXAMPLE 2

Preparation of Cyclo[MeLeu-Lac-MeLeu-($H_2N$)PhLac-MeLeu-Lac-MeLeu-PhLac]

Cyclo[MeLeu-Lac-MeLeu-($O_2N$)PhLac-MeLeu-Lac-MeLeu-PhLac] (18.6 g) as obtained in Example 1 was dissolved in methanol (190 ml), and to the resulting solution was added 10% palladium/carbon (1.9 g). The resulting mixture was catalytically reduced at room temperature under atmospheric pressure. After filtering the resulting reaction solution to remove the catalyst off, the filtered reaction solution was subjected to evaporation to remove the solvent, and the resultant residue was purified by a silica gel column chromatography (eluted with ethyl acetate-hexane=2:1, v/v), thus to afford the titled compound (71 g; yield 39.4%) as white powder.

EXAMPLE 3

Preparation of Cyclo[MeLeu-Lac-MeLeu-(HO)PhLac-MeLeu-Lac-MeLeu-PhLac], Namely PF1022 E Substance Cyclo[MeLeu-Lac-MeLeu-($H_2N$)PhLac-MeLeu-Lac-MeLeu-PhLac] (7.1 g) as obtained in Example 2 was dissolved in TFA (70 ml), and to the resulting solution was added sodium nitrite (0.76 g). The resulting mixture was subjected to the reaction at 60–65° C. for 1 hour. The solvent used was evaporated off from the resulting reaction solution. The residue obtained was dissolved in a mixture of 1,4-dioxane (140 ml) and water (28 ml), and to the resulting solution was added sodium hydrogen carbonate (6.18 g). The resulting mixture was subjected to the reaction at room temperature for 5 hours. The reaction solution so obtained was diluted with ethyl acetate (500 ml), and washed twice with water (500 ml, each), and the solvent was evaporated off from the solution under a reduced pressure. The residue was purified by a silica gel column chromatography (eluted with ethyl acetate-hexane=4:3, v/v) and then crystallized from ethyl acetate to yield the titled compound (2.1 g; 30%) as crystalline white powder.

The PF1022 E substance thus obtained by the synthesis in this Example was confirmed to coincide completely with the PF1022 E substance which was obtained by the fermentation method in respect of its $[\alpha]_D$, NMR and MS spectra.

EXAMPLE 4

Preparation of Cyclo[MeLeu-Lac-MeLeu-($NCCH_2O$)PhLac-MeLeu-Lac-MeLeu-PhLac]

Cyclo[MeLeu-Lac-MeLeu-(HO)PhLac-MeLeu-Lac-MeLeu-PhLac] (namely, PF1022 E substance)(482 mg) as obtained in Example 3 was dissolved in THF (10 ml), and to the resulting solution were added bromoacetonitrile (0.12 ml) and sodium hydride (100 mg) (as a 55% dispersion in mineral oil) under ice-cooling. The mixture obtained was warmed up to room temperature and the reaction was effected at room temperature for 1 hour. The resulting reaction solution was diluted with ethyl acetate (50 ml), washed twice with water (50 ml each) and the solvent was evaporated off from the solution under a reduced pressure. The residue was purified by a silica gel column chromatography (eluted with chloroform-ethyl acetate=1:2, v/v), thus to afford the titled compound (477 mg; yield 94.4%) as white powder.

NMR($CDCl_3$): $\delta$=0.82–1.05(24H,m, $\delta$-$CH_3$(MeLeu)), 1.26–1.71(18H,m, $\beta$-$CH_3$(Lac), $\beta$-$CH_2$, $\gamma$-CH(MeLeu)), 2.73–3.20(16H,m,N—Me, $\beta$-$CH_2$(($NCCH_2O$)PhLac, PhLac)), 3.90–5.70(8H,m, $\alpha$-CH), 4.70(2H,s,$NCCH_2O$), 6.86–6.94(2H,m,aromatic(($NCCH_2O$)PhLac)), 7.20–7.30 (7H,m,aromatic(($NCCH_2O$)PhLac,PhLac)); MS(FD): 1059 (M+1).

EXAMPLE 5

Preparation of Cyclo[MeLeu-Lac-MeLeu-($BocNHCH_2CH_2O$)PhLac-MeLeu-Lac-MeLeu-PhLac]

Cyclo[MeLeu-Lac-MeLeu-($NCCH_2O$)PhLac-MeLeu-Lac-MeLeu-PhLac] (461 mg) as obtained in Example 4 was dissolved in ethanol (1.5 ml), and to the resulting solution were added concentrated hydrochloric acid (0.2 ml) and 10% palladium/carbon (50 mg). The mixture obtained was subjected to catalytic reduction with hydrogen under a moderate pressure (45 psi) at room temperature for 16 hours. After filtering the catalyst off from the reaction solution, the filtrate was concentrated to dryness under a reduced pressure, to give a residue comprising the compound which is titled in Example 6 below but was in the form of a crude hydrochloride.

This residue was dissolved in a mixture of dioxane (10 ml) and water (10 ml), and to the resulting solution were added triethylamine (0.25 ml) and DiBoc reagent (240 mg). The resultant mixture was stirred at room temperature for 2.5 hours. After evaporating the dioxane off from the reaction solution under a reduced pressure, 5% aqueous citric acid and ethyl acetate were added to the residue, followed by separating the aqueous layer and organic layer. The organic layer (solution) so separated was concentrated under a reduced pressure. The residue so obtained was purified by a silica gel column chromatography (eluted with chloroform-ethyl acetate=2:1), thus yielding the titled compound (296 mg; 58.2%) as white powder.

NMR(CDCl$_3$): δ=0.83–1.05(33H,m, δ-CH$_3$(MeLeu), Boc), 1.35–2.01(18H,m, β-CH$_3$(Lac), β-CH$_2$, γ-CH (MeLeu)), 2.74–3.15(20H,m,N—Me, β-CH$_2$ ((BocNHCH$_2$CH$_2$O)PhLac,PhLac)BocNHCH$_2$CH$_2$O), 3.50–5.75(8H,m, α-CH), 686–6.94(2H,m,aromatic ((BocNHCH$_2$CH$_2$O)PhLac)), 7.20–7.30(7H,m,aromatic ((BocNHCH$_2$CH$_2$O)PhLac,PhLac)).

EXAMPLE 6

Preparation of Cyclo[MeLeu-Lac-MeLeu-(NH$_2$CH$_2$CH$_2$O)PhLac-MeLeu-Lac-MeLeu-PhLac] (Compound Code No. PF1022-278 substance)

Cyclo[MeLeu-Lac-MeLeu-(BocNHCH$_2$CH$_2$O)PhLac-MeLeu-Lac-MeLeu-PhLac] (296 mg) as obtained in Example 5 was dissolved in methylene chloride (3 ml), and to the resulting solution was slowly added TFA (0.5 ml) under ice-cooling. The resultant mixture was stirred at room temperature for 2.5 hours. After the mixture was again ice-cooled, TFA (0.2 ml) was further added thereto, and the mixture was stirred at room temperature for 45 minutes. The reaction solution obtained was concentrated under a reduced pressure, and an aqueous saturated sodium hydrogen carbonate and ethyl acetate were added to the residue, followed by separating the aqueous layer and organic layers. The organic layer (solution) so separated was concentrated to dryness under a reduced pressure, thus to afford the titled compound in a quantitative yield as white powder.

EXAMPLE 7

Preparation of Cyclo[MeLeu-Lac-MeLeu((CH$_3$)$_2$NCH$_2$CH$_2$O)PhLac-MeLeu-Lac-MeLeu-PhLac] (Compound Code No. PF1022-235 substance)

Cyclo(MeLeu-Lac-MeLeu-(NH$_2$CH$_2$CH$_2$O)PhLac-MeLeu-Lac-MeLeu-PhLac] hydrochloride (283 mg) was dissolved in ethanol (6 ml), and to the resulting solution were added 37% aqueous formaldehyde solution (0.43 ml) and 10% palladium/carbon (65 mg). The mixture obtained was subjected to a catalytic reduction with hydrogen under atmospheric pressure at room temperature for 8 hours. After the catalyst was filtered off from the reaction solution, the filtrate was concentrated to dryness under a reduced pressure. The residue was purified by a silica gel column chromatography (eluted with chloroform-methanol=20:1, v/v), thus affording the titled compound (192 mg; 68.5%) as white powder.

$[α]_D$=−71.0° (c=0.13,MeOH); NMR(CDCl$_3$): δ=0.80–1.05(24H,m, δ-CH$_3$(MeLeu)), 1.25–1.80(18H,m, β-CH$_3$(Lac), β-CH$_2$, γ-CH(MeLeu)), 2.41(6H,s,N(CH$_3$)$_2$), 2.73–3.20(20H,m,N—CH$_3$(MeLeu), β-CH$_2$(((CH$_3$)NCH$_2$CH$_2$O)PhLac,PhLac),(CH$_3$)NCH$_2$CH$_2$O), 4.08–5.75 (8H,m, α-CH), 6.84, 7.14(each 2H, each d, each J=8 Hz,aromatic((CH$_3$)NCH$_2$CH$_2$OPhLac), 7.26(5H,s,aromatic (PhLac)); MS(SIMS): 1036(M+1).

EXAMPLE 8

Preparation of Cyclo[MeLeu-Lac-MeLeu-((C$_2$H$_5$)$_2$NCH$_2$CH$_2$O)PhLac-MeLeu-Lac-MeLeu-PhLac] (Compound Code No. PF1022-236 substance)

Cyclo[MeLeu-Lac-MeLeu-(NH$_2$CH$_2$CH$_2$O)PhLac-MeLeu-Lac-MeLeu-PhLac] hydrochloride (425 mg) as obtained in Example 6 was dissolved in ethanol (5 ml), and to the resulting solution were added 90% aqueous acetaldehyde solution (39 ml) and 10% palladium/carbon (60 mg). The mixture obtained was subjected to a catalytic reduction with hydrogen under atmospheric pressure at room temperature for 8 hours. After the catalyst was filtered off from the reaction solution, the filtrate was concentrated to dryness under a reduced pressure. The residue was purified by a silica gel column chromatography (eluted with chloroform-methanol 20:1, v/v), thus to yield the titled compound (289 mg; 66.7%) as white powder.

$[α]_D$=−54.8° (c=0.21,MeOH); NMR(CDCl$_3$): δ=0.80–1.07(24H,m, δ-CH$_3$(MeLeu)), 1.25–1.81(18H,m, β-CH$_3$(Lac), β-CH$_2$, γ-CH(MeLeu)), 1.38(6H,t,J=7 Hz,N (CH$_2$CH$_3$)$_2$), 2.61–3.15(24H,m,N—CH$_3$(MeLeu), β-CH$_2$ (((C$_2$H$_5$)$_2$NCH$_2$CH$_2$O)PhLac,PhLac)) 4.00–5.67(8H,m, α-CH), 6.79–6.83, 711–7.14(each 2H, each m,aromatic (((C$_2$H$_5$)$_2$NCH$_2$CH$_2$O)PhLac)), 7.24–7.25(5H,m,aromatic (PhLac)); MS(SIMS): 1064(M+1), 1065(M+2).

EXAMPLE 9

Preparation of Cyclo[MeLeu-Lac-MeLeu-(Pr$_2$NCH$_2$CH$_2$O)PhLac-MeLeu-Lac-MeLeu-PhLac] (Compound Code No. PF1022-270 substance)

Cyclo[MeLeu-Lac-MeLeu-(NH$_2$CH$_2$CH$_2$O)PhLac-MeLeu-Lac-MeLeu-PhLac] (namely, PF1022-278 substance) (500 mg) obtained in Example 6 was dissolved in DMF (5 ml), and to the resulting solution were added potassium carbonate (112 mg) and 1-iodopropane (86 μl). The reaultant mixture was stirred overnight at room temperature. Ethyl acetate and water were added to the resulting reaction solution, and the organic layer (solution) so separated was dried over magnesium sulfate. The solvent was evaporated off from the organic layer. The residue was purified by a silica gel column chromatography, thus yielding the titled compound (160 mg; 54%).

$[α]_D$=−81.9° (c=0.21,MeOH); NMR(CDCl$_3$): δ=0.80–1.05(30H,m, δ-CH$_3$(MeLeu),CH$_3$(propyl)), 1.25–1.80(22H,m, β-CH$_3$(Lac), β-CH$_2$(MeLeu), γ-CH (MeLeu), CH$_2$CH$_3$(Propyl)), 2.48(4H,t,CH$_2$N(Propyl)), 2.75–2.83, 3.00–3.15(20H,m,N—Me(MeLeu), β-CH$_2$ (PhLac), OCH$_2$CH$_2$N), 3.90–5.67(8H,m, α-CH(MeLeu, Lac,PhLac), 6.79–6.82(2H,m,aromatic), 7.12–7.29(7H,m, aromatic); MS(SIMS): 1092(M+1).

EXAMPLE 10

Preparation of Cyclo[MeLeu-Lac-MeLeu (Bu$_2$NCH$_2$CH$_2$O)PhLac-MeLeu-Lac-MeLeu-PhLac] (Compound Code No. PF1022-271 substance)

Cyclo[MeLeu-Lac-MeLeu-(NH$_2$CH$_2$CH$_2$O)PhLac-MeLeu-Lac-MeLeu-PhLac] (namely, PF1022-278 substance) (1.08 g) was dissolved in DMF (10 ml), and to the resulting solution were added potassium carbonate (296 mg) and 1-iodo-butane (270 l). The resultant mixture was stirred at room temperature overnight. Ethyl acetate and water were added to the reaction solution. The organic layer so separated was dried over magnesium sulfate. The solvent was evaporated off therefrom, and the residue was purified by a silica gel chromatography, thus yielding the titled compound (529 mg; 44%).

$[\alpha]_D = -81.8°$ (c=0.17,MeOH); NMR(CDCl$_3$): δ=0.74–1.05(30H,m, δ-CH$_3$(MeLeu), CH$_3$(butyl)), 1.24–1.74(26H,m, β-CH$_3$(Lac), β-CH$_2$(MeLeu), γ-CH (MeLeu), CH$_2$CH$_2$CH$_2$CH$_3$(butyl)), 2.49(4H,t,CH$_2$N (butyl)), 2.73–3.16(20H,m,N—Me(MeLeu), β-CH$_2$ (PhLac),OCH$_2$CH$_2$N), 4.00–5.65(8H,m, α-CH(MeLeu,Lac, PhLac), 6.70–6.80(2H,m,aromatic), 7.12–7.29(7H,m, aromatic); MS(FAB): 1120(M+1).

EXAMPLE 11

Preparation of Cyclo[MeLeu-((CH$_3$OCH$_2$CH$_2$)$_2$NCH$_2$CH$_2$O)PhLac-MeLeu-Lac-MeLeu-PhLac-MeLeu-Lac] (Compound Code No. PF1022-238 substance)

Cyclo[MeLeu-(NH$_2$CH$_2$CH$_2$O)PhLac-MeLeu-Lac-MeLeu-PhLac-MeLeu-Lac] hydrochloride (406 mg) was dissolved in DMF (6 ml), and to the resulting solution were added 2-bromoethyl methyl ether (158 μl), sodium iodide (86 mg) and potassium carbonate (212 mg). The reaction was carried out at 80° C. for 3 hours. The resulting reaction solution was diluted with ethyl acetate (50 ml), and washed twice with water (50 ml, each). The solvent was evaporated off from the solution under a reduced pressure, and the residue was purified by a silica gel column chromatography (eluted with chloroform-ethyl acetate=2:1, v/v), thus to afford the titled compound (132 mg; 30.6%) as white powder.

$[\alpha]_D = -81.8°$ (c=0.11,MeOH); NMR(CDCl$_3$): δ=0.82–1.05(24H,m, δ-CH$_3$(MeLeu)), 1.23–1.81(18H,m, β-CH$_3$(Lac), β-CH$_2$, γ-CH(MeLeu)), 2.74–3.18(34H,m,N—CH$_3$(MeLeu), β-CH$_2$((CH$_3$OCH$_2$CH$_2$)$_2$NCH$_2$CH$_2$O) PhLac,PhLac)) 3.77–5.70(8H,m, α-CH), 6.82, 7.16(each 2H, each d, each J=8 Hz,aromatic(((CH$_3$OCH$_2$CH$_2$)$_2$NCH$_2$CH$_2$O)PhLac), 7.25–7.29(5H,m,aromatic(PhLac)); MS(FD): 1125(M+2).

EXAMPLE 12

Preparation of Cyclo[MeLeu-(MorCH$_2$CH$_2$O) PhLac-MeLeu-Lac-MeLeu-PhLac-MeLeu-Lac] (Compound Code No. PF1022-239 substance)

Cyclo[MeLeu-(NH$_2$CH$_2$CH$_2$O)PhLac-MeLeu-Lac-MeLeu-PhLac-MeLeu-Lac] hydrochloride (227 mg) was dissolved in DMF (1 ml), and to the resulting solution were added 2-bromoethyl ether.(32 μl), sodium iodide (24 mg) and potassium carbonate (59 mg). The reaction was conducted at 80° C. for 6 hours. The reaction solution obtained was diluted with ethyl acetate (20 ml), and washed twice with water (20 ml, each) The solvent used was evaporated off from the solution under a reduced pressure. The residue was purified by a silica gel column chromatography (eluted with chloroform-methanol=50:1, v/v), thus affording the titled compound (95 mg; 41%) as white powder.

$[\alpha]_D = -70.6°$ (c=0.095,MeOH); NMR(CDCl$_3$): δ=0.75–1.05(24H,m, δ-CH$_3$(MeLeu)), 1.25–1.81(18H,m, β-CH$_3$(Lac), β-CH$_2$, γ-CH(MeLeu)), 2.56–3.75(28H,m,N—CH$_3$(MeLeu), β-CH$_2$((MorCH$_2$CH$_2$O)PhLac,PhLac), 4.05–5.67(8H,m, α-CH), 6.83,7.13(each 2H, each d, each J=8 Hz,aromatic((MorCH$_2$CH$_2$O)PhLac)), 7.26(5H,s, aromatic(PhLac)); MS (SIMS): 1078(M+1).

EXAMPLE 13

Preparation of Cyclo[MeLeu-Lac-MeLeu-(PyrCH$_2$CH$_2$O)PhLac-MeLeu-Lac-MeLeu-PhLac] (Compound Code No. PF1022-284 substance)

Cyclo[MeLeu-Lac-MeLeu-(NH$_2$CH$_2$CH$_2$O)PhLac-MeLeu-Lac-MeLeu-PhLac] (namely, PF1022-278 substance) (150 mg) was dissolved in DMF (15 ml), and to the resulting solution were added potassium carbonate (41 mg), sodium iodide (49 mg) and 1,4-dibromobutane (19.4 μl). The resultant mixture was stirred at 50° C. for 5.5 hours. Ethyl acetate and water were added to the resulting reaction solution, followed by separating the aqueous and organtc layers. The organic layer so separated was dried over magnesium sulfate. The solvent was evaporated off from the solution, and the residue was purified by a silica gel chromatography, thus affording the titled compound (55 mg; 39%)

$[\alpha]_D = -85.0°$ (c=0.2,MeOH); NMR(CDCl$_3$): δ=0.80–1.04 (24H,m, δ-CH$_3$(MeLeu)), 1.35–1.89(22H,m, β-CH$_3$(Lac), β-CH$_2$(MeLeu), γ-CH(MeLeu), pyrrolidino-H), 2.64–3.15 (24H,m,N—Me(MeLeu), β-CH$_2$(PhLac), pyrrolidino-H, OCH$_2$CH$_2$N), 4.00–5.70(8H,m, α-CH(MeLeu,Lac,PhLac), 6.80–6.86(2H,m,aromatic), 7.12–7.32(7H,m,aromatic); MS (FAB): 1062(M+1).

EXAMPLE 14

Preparation of Cyclo[MeLeu-Lac-MeLeu-(PipCH$_2$CH$_2$O)PhLac-MeLeu-Lac-MeLeu-PhLac] (Compound Code No. PF1022-285 substance)

Cyclo[MeLeu-Lac-MeLeu-(NH$_2$CH$_2$CH$_2$O)PhLac-MeLeu-Lac-MeLeu-PhLac] (PF1022-278 substance) (296 mg) was dissolved in DMF (3 ml), and to the resulting solution were added potassium carbonate (66 mg), sodium iodide (79 mg) and 1,5-dibromopentane (35.5 μl). The resultant mixture was stirred at 50° C. for 5.5 hours. Ethyl acetate and water were added to the reaction solution obtained. The organic layer so separated was dried over magnesium sulfate. The solvent was evaporated off from the solution, and the residue was purified by a silica gel chromatography, thus affording the titled compound (162 mg; 74%).

$[\alpha]_D = -79.5°$ (c=0.22,MeOH); NMR(CDCl$_3$): δ=0.80–1.05(24H,m, β-CH$_3$(MeLeu)), 1.35–1.81(24H,m, β-CH$_3$(Lac), β-CH$_2$(MeLeu), γ-CH(MeLeu), piperidino-H), 2.48–3.15(24H,m,N—Me(MeLeu), β-CH$_2$(PhLac), O CH$_2$CH$_2$N,piperidino-H), 4.07–5.67(8H,m, α-CH(MeLeu, Lac,PhLac), 6.80–6.86(2H,m,aromatic), 7.12–7.32(7H,m, aromatic); MS(FAB): 1076(M+1).

EXAMPLE 15

Preparation of Cyclo[MeLeu-Lac-MeLeu-((C$_2$H$_5$)$_2$NCH$_2$CH$_2$O)PhLac-MeLeu-Lac-MeLeu-PhLac] (Compound Code No. PF1022-274 substance)

(1) Synthesis of 3-benzyloxycarbonylamino-1-propanol

3-Amino-1-propanol (5.0 g) was dissolved in a mixture of dioxane (50 ml) and water (50 ml), and to the resulting solution were added under ice-cooling sodium hydrogen carbonate (4.3 mg) and benzyloxychloride (15.6 ml). The resultant mixture was stirred at that temperature for 1.5 hours. Ethyl acetate and water were added to the reaction solution obtained. The organic layer so separated was dried over magnesium sulfate. The solvent was evaporated off from the solution, and the residue was purified by a silica gel chromatography, thus affording the title compound (8.5 g; 62%).

NMR(CDCl$_3$): δ=1.70(2H,m), 2.55(1H,t), 3.36(2H,q), 3.68(2H,q), 5.11(2H,s), 7.32–7.37(5H,m)

(2) Synthesis of 3-benzyloxycarbonylamino-1-propanol t-butyldimethylsilyl ether

3-Benzyloxycarbonylamino-1-propanol (8.1 g) was dissolved in methylene chloride (200 ml), and to the resulting solution were added triethylamine (4.1 g) and t-butyldimethylsilyl chloride (7.1 g). The resultant mixture was stirred at room temperature for 1 day. Ethyl acetate and water were added to the reaction solution obtained. The organic layer so separated was dried over magnesium sulfate. The solvent was evaporated off from the solution, and the residue was purified by a silica gel chromatography, thus affording the titled compound (10.1 g; 82%).

NMR(CDCl$_3$): δ=0.12(6H,s), 0.96(9H,s), 1.79(2H,m), 3.39(2H,q), 3.78(2H,t), 5.16(2H,s), 7.38–7.42(5H,m)

(3) Synthesis of N-ethyl 3-benzyloxycarbonylamino-1-propanol t-butyl-dimethylsilyl ether 3-Benzyloxycarbonylamino-1-propanol t-butyldimethylsilyl ether (10.1 g) was dissolved in THF (250 ml), and to the resulting solution were added under ice-cooling ethyl iodide (5.1 ml) and a 60% sodium hydride (as a mineral oil dispersion) (2.0 g). The resultant mixture was stirred under ice-cooling for 30 minutes and then at room temperature for 15 hours. Ethyl acetate and water were added to the reaction solution obtained. The organic layer so separated was washed with water and then dried over magnesium sulfate. The solvent was evaporated off from the solution, and the residue was purified by a silica gel chromatography, thus affording the titled compound (8.5 g; 80%).

NMR(CDCl$_3$): δ=0.03(6H,s), 0.88(9H,s), 1.12(3H,t), 1.74(2H,q), 3.39(4H,q), 3.61(2H,t), 5.12(2H,s), 7.29–7.36 (5H,m).

(4) Synthesis of N-ethyl 3-benzyloxycarbonylamino-1-propanol

N-Ethyl 3-benzyloxycarbonylamino-1-propanol t-butyldimethylsilyl ether (8.5 g) was dissolved in THF (120 ml), and to the resulting solution was added under ice-cooling a solution of 1N tetra-butylammonium fluoride in THF (48 ml). The resultant mixture was stirred at room temperature for 1 hour. Ethyl acetate and water were added to the reaction solution obtained. The organic layer so sepasated was washed with water and then dried over magnesium sulfate. The solvent was evaporated off from the solution, and the residue was purified by a silica gel chromatography, thus affording the titled compound (4.0 g; 71%)

NMR(CDCl$_3$): δ=1.13(3H,t), 1.74–1.78(3H,m), 3.27(2H, q), 3.43(2H,t), 3.57(2H,bs), 5.15(2H,s), 7.27–7.39(5H,m)

(5) Synthesis of N-ethyl 3-benzyloxycarbonylamino-1-tosyloxypropane

N-Ethyl 3-benzyloxycarbonylamino-1-propanol (4.0 g) was dissolved in methylene chloride (20 ml), and to the resulting solution were added pyridine (1.8 ml) and tosyl chloride (3.9 g). The resultant mixture was stirred at room temperature for 2 days. Ethyl acetate and water were added to the reaction solution obtained. The organic layer so separated was washed with an aqueous potassium hydrogen sulfate solution and then with water and then dried over magnesium sulfate. The solvent was evaporated off from the solution, and the residue was purified by a silica gel chromatography, thus affording the titled compound (4.4 g; 69%).

NMR(CDCl$_3$): δ=1.08(3H,t), 1.90(3H,bs), 2.44(3H,s), 3.19–3.30(4H,m), 4.05(2H,bs), 5.15(2H,s), 7.15–7.34(7H, m), 7.76(2H,m)

(6) Synthesis of N-ethyl 3-benzyloxycarbonylamino-1-iodopropane

N-Ethyl 3-benzyloxycarbonylamino-1-tosyloxypropane (1.02 g) was dissolved in acetone (20 ml), and to the resulting solution was added sodium iodide (0.80 g). The resultant mixture was stirred at 45° C. for 2 hours. Ethyl acetate and water were added to the reaction solution obtained, and the organic layer so separated was washed with water and then dried over magnesiumsulfate. The solvent was evaporated off from the solution, and the residue was purified by a silica gel chromatography, thus to afford the titled compound (0.69 g; 76%).

NMR(CDCl$_3$): δ=1.33(3H,t), 2.10(3H,bs), 3.14(2H,m), 3.33(4H,t), 5.12(2H,s), 7.28–7.40(7H,m), 7.76(2H,m).

(7) Synthesis of Cyclo[MeLeu-Lac-MeLeu-(($C_2H_5$)N(Cbz) $CH_2CH_2CH_2O$)PhLac-MeLeu-Lac-MeLeu-PhLac]

PF1022 E substance (412 mg) was dissolved in a mixture of DMF (5.5 ml) and acetone (16 ml), and to the resulting solution were added N-ethyl 3-benzyloxycarbonylamino-1-iodopropane (530 mg) as obtained in the above item (6), as well as cesium carbonate (400 mg) and sodium iodide (56 mg). The reaultant mixture was stirred at room temperature for 7 days. Ethyl acetate and water were added to the reaction solution obtained. The organic layer so separated was washed with water and then dried over magnesium sulfate. The solvent was evaporated off from the solution, and the residue was purified by a silica gel chromatography, thus to afford the titled compound (401 g; 77%).

NMR(CDCl$_3$): δ=0.82–1.04(27H,m, δ-$CH_3$(MeLeu), $CH_3CH_2N$), 1.31–1.81(18H,m, β-$CH_2$, γ-CH(MeLeu), $CH_3$ (Lac)), 2.03(2H,m,$NCH_2CH_2CH_2O$), 2.71–3.15(16H,m, NMe(MeLeu), β-$CH_2$(PhLac)), 3.32(2H,m,$CH_3CH_2NEt$), 3.43(2H,t,$NCH_2CH_2CH_2O$), 3.91(2H,m,$NCH_2CH_2O$), 4.44–5.68(10H,m,$CH_2$(Cbz), α-CH), 6.76–6.80(2H,m, aromatic(($C_2H_5$)N(Cbz)$CH_2CH_2CH_2O$)PhLac)), 7.06–7.38 (12H,m,aromatic(PhLac,($C_2H_5$) N(Cbz)$CH_2CH_2CH_2O$)PhLac)); MS(FAB): 1184(M+1).

(8) Synthesis of Cyclo[MeLeu-Lac-MeLeu-(($C_2H_5$) $_2NCH_2CH_2CH_2O$)PhLac-MeLeu-Lac-MeLeu-PhLac] (Compound Code No. PF1022-274 substance)

Cyclo[MeLeu-Lac-MeLeu-(($C_2H_5$)N(Cbz) $CH_2CH_2CH_2O$) PhLac-MeLeu-Lac-MeLeu-PhLac] (401 mg) obtained in the above item (7) was dissolved in ethanol (6 ml), and to the resulting solution was added 10% Pd/carbon (51 mg). The resultant mixture was stirred under a hydrogen atmosphere at room temperature for 17 hours. After separating the catalyst from the reaction solution by filtration, the solvent was evaporated off from the solution, and the residue was dissolved in ethanol (5 ml). To the resulting solution was added 10% Pd/carbon (38 mg). The mixture obtained was ice-cooled, followed by adding acetaldehyde (5 ml) thereto. The resulting mixture was again stirred under a hydrogen atmosphere at room temperature overnight. The catalyst was removed by filtration from the reaction solution and the solvent was evaporated off. The residue was then purified by a silica gel chromatography, thus yielding the titled compound (240 mg; 73%).

[α]$_D$=−84.9° (c=0.11,MeOH); NMR(CDCl$_3$): δ=0.75–1.08(30H,m, δ-$CH_3$(MeLeu), $CH_3CH_2N$), 1.31–1.77(18H,m, β-CH$_2$, γ-CH(MeLeu), CH$_3$(Lac)), 1.92 (2H,m,NCH$_2$CH$_2$CH$_2$O), 2.49–3.15(22H,m,NMe(MeLeu), β-CH$_2$(PhLac,(C$_2$H$_5$)$_2$NCH$_2$CH$_2$CH$_2$O)PhLac), CH$_3$CH$_2$N,NCH$_2$CH$_2$CH$_2$O), 3.98(2H,m,NCH$_2$CH$_2$O), 4.44–5.68(8H,m, α-CH), 6.78–6.84(2H,m,aromatic((C$_2$H$_5$)$_2$NCH$_2$CH$_2$CH$_2$O)PhLac)), 7.10–7.31(7H,m,aromatic (PhLac,(C$_2$H$_5$)$_2$N(Cbz)CH$_2$CH$_2$CH$_2$O)PhLac)); MS(FAB): 1079(M+1).

EXAMPLE 16

Cyclo[MeLeu-Lac-MeLeu-((S)-pyrrolidinyl-2-methoxy)PhLac-MeLeu-Lac-MeLeu-PhLac] (Compound Code No. PF1022-302 substance (1) Synthesis of N-Boc-(S)-pyrrolidine-2-methanol (S)-Pyrrolidine-2-methanol (0.99 ml) was dissolved in H$_2$O (10 ml), and to the resulting solution were added triethylamine (4.20 ml) and DiBoc reagent (2.40 g). The resultant mixture was stirred at room temperature for 16 hours. To the resulting reaction solution, after being concentrated, ethyl acetate was added. The mixture obtained was washed with a 5% aqueous citric acid, dried over anhydrous magnesium sulfate and then concenteated to remove the solvent therefrom. The residue was purified by a silica gel column chromatography, thus affording the titled compound (1.625 g; 80.8%).

(2) Synthesis of Cyclo[MeLeu-Lac-MeLeu-(N-BOC-(S)-pyrrolidinyl-2-methoxy)PhLac-MeLeu-Lac-MeLeu-PhLac]

N-Boc-(S)-pyrrolidine-2-methanol (522 mg) obtained in the above item (1) was dissolved in THF (5 ml), and to the resulting solution were added DEAD (16 ml) and triphenylphosphine (271 mg). The resultant mixture was stirred at room temperature for 30 minutes. Then, PF1022 E substance (500 mg) was added thereto and the mixture was stirred at room temperature overnight. Further, DEAD (0.16 ml) and triphenylphosphine (271 mg) were added thereto, and the resulting mixture was stirred at room temperature for 10 days. The reaction solution obtained was concentrated, and ethyl acetate and water were added to the residue. The organic layer so separated was dried over anhydrous magnesium sulfate and then concentrated to remove the solvent. The residue so obtained was purified by a silica gel column chromatography, to yieldthe titled compound (386 mg; 64.8%).

(3) Synthesis of Cyclo[MeLeu-Lac-MeLeu-((S)-pyrrolidinyl-2-methoxy)PhLac-MeLeu-Lac-MeLeu-PhLac]

Cyclo[MeLeu-Lac-MeLeu-(N-Boc-(S)-pyrrolidinyl-2-methoxy)PhLac-MeLeu-Lac-MeLeu-PhLac] (386 mg) as obtained in the above step (2) was dissolved in methylene chloride (4 ml), and to the resulting solution was added TFA (0.4 ml) under ice-cooling. The resultant mixture was stirred at room temperature for 3 hours. The reaction solution so obtained was concentrated, and to the residue were added ethyl acetate and water. The organic layer so separated was washed with an aqueous saturated sodium hydrogen carbonate solution and then dried over anhydrous magnesium sulfate. The solvent was removed from the solution by evaporation, and the residue was purified by a silica gel chromatography, to afford the titled compound (182 mg; 51%)

$[\alpha]_D = -80.0°$ (c=0.11,MeOH); NMR(CDCl$_3$): δ=0.80–1.05(24H,m, δ-CH$_3$(MeLeu)), 1.36–2.01(22H,m, β-CH$_3$(Lac), β-CH$_2$(MeLeu), γ-CH(MeLeu), pyrrolidinyl-H), 2.75–3.15(19H,m,N—Me(MeLeu), β-CH$_2$(PhLac), pyrrolidinyl-H), 3.65–3.71, 3.97, 4.44, 5.09, 5.31–5.67(11H, m, α-CH(MeLeu,Lac, PhLac), OCH$_2$,NH), 6.81–6.85(2H, m,aromatic), 7.12–7.27(7H,m,aromatic); MS (FAB) 1048 (M+1).

EXAMPLE 17

Cyclo[MeLeu-Lac-MeLeu-(imidazolyl-4-methoxy) PhLac-MeLeu-Lac-MeLeu-PhLac] (PF1022-304 substance)

(1) Synthesis of N-Boc-4-(hydroxymethyl)-imidazole 4-(Hydroxymethyl)-imidazole hydrochloride (955 mg) was dissolved in a mixture of 1,4-dioxane (10 ml) and water (10 ml), and to the resulting solution were added triethylamine (3.1 ml) and DiBoc reagent (1.86 g). The resultant mixture was stirred at room temperature for 4 hours. After the solvent was removed from the resulting reaction solution by evaporation, ethyl acetate and 5% acetie aicl were added to the residue. The organic layer so separated was dehydrated with anhydrous magnesium sulfate. The solvent was evaporated off from the solution, and the residue was purified by a silica gel chromatography, thus affording the titled compound (560 mg; 39.8%).

(2) Synthesis of Cyclo[MeLeu-Lac-MeLeu-(N-Boc-imidazolyl-4-methoxy)PhLac-MeLeu-Lac-MeLeu-PhLac]

PF1022 E substance (200 mg) was dissolved in THF (2 ml), and to the resulting solution were added DEAD(65 μl), triphenylphosphine (108 mg) and N-Boc-4-(hydroxymethyl)-imidazole (205 mg). The resultant mixture was stirred at room temperature for 2 hours. After the reaction solution obtained was concentrated, ethyl acetate was added to the concentrate, followed by removing insoluble material formed by filtration. The filtrate was washed with water and dehydrated with anhydrous magnesium sulfate. The solvent was evaporated of from the solution, and the residue was purified by a silica gel column chromatography, affording the titled compound (100 mg; 46.3%).

(3) Synthesis of Cyclo[MeLeu-Lac-MeLeu-(imidazolyl-4-methoxy)PhLac-MeLeu-Lac-MeLeu-PhLac]

Cyclo[MeLeu-Lac-MeLeu-(N-Boc-imidazolyl-4-methoxy)PhLac-MeLeu-Lac-MeLeu-PhLac] (110 mg) obtained in the step (2) above was dissolved in methylene chloride (1 ml), and to the resulting solution TFA (0.1 ml) was added under ice-cooling. The resultant mixture was stirred at room temperature for 1.5 hours for effecting the elimination of the amino-protecting group. After the reaction solution so obtained was concentrated, ethyl acetate and an aqueous saturated sodium hydrogen carbonate were added to the residue. The organic layer so separated was dried over anhydrous magnesium sulfate and the solvent was distilled off from the solution. The resulting residue was purified by a silica gel column chromatography, yielding the titled compound of this EXAMPLE 17 (61.4 mg; 61.2%).

$[\alpha]_D = -80.0°$ (c=0.17,MeOH); NMR(CDCl$_3$): δ=0.82–1.05(24H,m, δ-CH$_3$(MeLeu)), 1.26–1.78(18H,m, β-CH$_3$(Lac), β-CH$_2$(MeLeu), γ-CH(MeLeu)), 2.72–3.16 (16H,m,N—Me(MeLeu), δ-CH$_2$(PhLac), 5.03(2H,s,OCH$_2$), 4.48, 5.06, 5.34–5.70(8H,m, α-H(MeLeu,Lac,PhLac), 6.88–6.94(2H,m,aromatic), 7.10–7.27(7H,m,aromatic); MS(FAB): 1045(M+1).

EXAMPLE 18

Cyclo[MeLeu-Lac-MeLeu-(H$_2$NSCCH$_2$O)PhLac-MeLeu-Lac-MeLeu-PhLac]

Cyclo[MeLeu-Lac-MeLeu-(NCCH$_2$O)PhLac-MeLeu-Lac-MeLeu-PhLac] (2.07 g) as obtained in Example 4 and O,O'-diethyl dithiophosphate (3.0 ml) were dissolved in a mixture of water (0.35 ml), chloroform (2 ml) and toluene (2 ml), followed by heating under refluxing condition for 30 minutes. The reaction solution obtained was allowed to cool to room temperature and then diluted with ethyl acetate (100 ml), washed with water (50 ml) and then with an aqueous saturated sodium hydrogen carbonate solution. The washed solution was dried over anhydrous sodium sulfate. The solvent was evaporated off from the solution under a reduced pressure, and the residue was purified by a silica gel column chromatography (eluted with chloroform-ethyl acetate= 5:1~1:1), to afford the titled compound (1.67 g) as white powder.

EXAMPLE 19

Cyclo[MeLeu-Lac-MeLeu-(2-imidazolylmethoxy) PhLac-MeLeu-Lac-MeLeu-PhLac] (PF1022-305 substance)

Cyclo[MeLeu-Lac-MeLeu-($H_2NCSCH_2O$)PhLac-MeLeu-Lac-MeLeu-PhLac] (403 mg) as obtained in Example 18 above was dissolved in acetone (20 ml), and to the resulting solution was added methyl iodide (0.25 ml), and the resultant mixture was stirred at 30° C. for 2 days. The resulting reaction solution was concentrated and the residue was dissolved in benzene (4 ml). To the resulting solution was added aminoacetaldehyde dimethylacetal (40 μl), and the mixture obtained was stirred at 80° C. for 90 minutes. Then, 6N hydrochloric acid (4 ml) was added to the reaction solution obtained, followed by stirring at 100° C. for 1 hour. The resulting reaction solution was allowed to cool to room temperature, and then diluted with ethyl acetate (50 ml), washed with a mixture of 2N NaOH (10 ml) and an aqueous saturated sodium hydrogen carbonate (30 ml) and then with an aqueous saturated sodium chloride solution (30 ml) and further dried over anhydrous sodium sulfate. The dried solution was concentrated under a reduced pressure, and the residue was purified by a silica gel column chromatography (eluted gradiently with chloroform-methanol= 100:1~30:1), thus to afford the titled compound (231 mg) as white powder.

$[\alpha]_D = -94.2°$ (c=0.12,MeOH); $^1$H-NMR(CDCl$_3$): δ=0.71–1.06(27H,m), 1.18–1.82(15H,m), 2.7–3.22(16H,m), 4.46(1H,m), 5.0–5.72(9H,m), 6.85–6.94(2H,m), 7.07(2H,s), 7.1–7.34(7H,m), 10.2(1H,bs); MS(FAB): 1045(M+1).

EXAMPLE 20

Cyclo[MeLeu-Lac-MeLeu-(2-thiazolylmethoxy) PhLac-MeLeu-Lac-MeLeu-PhLac] (Compound Code No. PF1022-306 substance)

Cyclo[MeLeu-Lac-MeLeu-($H_2NCSCH_2O$)PhLac-MeLeu-Lac-MeLeu-PhLac] (280 mg) as obtained in Example 18 was dissolved in toluene (1.5 ml), and to the resulting solution were added bromoacetaldehyde diethylacetal (0.5 ml) and concentrated sulfuric acid (2 drops). The resultant mixture was stirred at 90° C. for 30 minutes. The reaction solution so obtained was allowed to cool to room temperature, then diluted with ethyl acetate (30 ml), washed with an aqueous saturated sodium hydrogen carbonate (20 ml), and further dried over anhydrous sodium sulfate. The dried solution was concentrated under a reduced pressure, and the resulting residue was purified by a silica gel column chromatography (eluted with chloroform-ethyl acetate= 4:1~2:1), thus to afford the titled compound (86.9 mg) as white powder.

$[\alpha]_D = -101.7°$ (c=0.11,MeOH); $^1$H-NMR(CDCl$_3$): δ=0.74–1.08(27H,m), 1.18–1.86(15H,m), 2.7–3.22(16H,m), 4.47(1H,m), 5.02–5.72(9H,m), 6.88–6.98(2H,m), 7.14–7.34 (7H,m), 7.37(1H,d,J=3.2 Hz), 7.80(1H,d,J=3.2 Hz); MS (FAB): 1062(M+1).

EXAMPLE 21

Cyclo[MeLeu-Lac-MeLeu-(3-(5-methyl-1,2,4-oxadiazolyl)-methoxy)PhLac-MeLeu-Lac-MeLeu-PhLac] (Compound Code No. PF1022-309 substance)

PF1022 E substance (300 mg) was dissolved in acetone (9 ml), and to the resulting solution were added potassium carbonate (214 mg), sodium iodide (232 mg) and 3-chloromethyl-5-methyl-1,2,4-oxadiazole (268 mg). The resultant mixture was stirred at 40° C. for 8 hours. After the solvent was removed from the reaction solution by evaporation, ethyl acetate and water were added to the residue. The organic layer so separated was dried over magnesium sulfate and the solvent was removed by evaporation. The residue was purified by a silica gel chromatography, to yield the titled compound (260 mg; 79%)

$[\alpha]_D = -89.6°$ (c=0.28,MeOH); NMR(CDCl$_3$): δ=0.83–1.04(24H,m, δ-CH$_3$(MeLeu)), 1.26–1.76(18H,m, β-CH$_3$(Lac), β-CH$_2$(MeLeu), γ-CH(MeLeu)), 2,67(3H,s,5-Me(oxazolyl)), 2.72–3.13(16H,m,N—Me(MeLeu), β-CH$_2$ (PhLac)), 4.50–5.67(8H,m, α-CH(MeLeu,Lac,PhLac)), 6.93–6.95(2H,m,aromatic), 7.16–7.26(7H,m,aromatic); MS(FAB): 1061(M+1).

EXAMPLE 22

Cyclo[MeLeu-Lac-MeLeu-(3-(5-isobutyl-1,2,4-oxadiazolyl)-methoxy)PhLac-MeLeu-Lac-MeLeu-PhLac] (Compound Code No. PF1022-310 substance)

PF1022E substance (509 mg) was dissolved in a mixture of DMF (4 ml) and acetone (13 ml), and to the resulting solution were added 3-chloromethyl-5-isobutyl-1,2,4-oxadiazole (512 mg) and cesium carbonate (522 mg) and the mixture so obtained was stirred at room temperature for 5 days. Ethyl acetate and water were added to the resulting mixture. The organic layer as separated was washed with water and dried over magnesium sulfate. The solvent was removed by evaporation, and the residue was purified by a silica gel chromatography, yielding the titled compound (465 mg; 81%).

$[\alpha]_D = -88.2°$ (c=0.11,MeOH); NMR(CDCl$_3$): δ=0.82–1.04(30H,m, δ-CH$_3$(MeLeu), α-CH$_3$(Lac), CH(CH$_3$)CH$_2$CH$_3$(isobutyl)), 1.35–1.90(20H,m, β-CH$_2$, γ-CH(MeLeu), CH$_3$(Lac), CH(CH$_3$)CH$_2$CH$_3$(isobutyl)), 2.63–3.15(18H,m,NMe(MeLeu), β-CH$_2$(PhLac,3-(5-isobutyl-1,2,4-oxadiazolylmethoxy)PhLac), 4.40–5.67(8H, m, α-CH), 6.90–6.96(2H,m,aromatic(3-(5-isobutyl-1,2,4-oxadiazolylmethoxy)PhLac), 7.14–7.28(7H,m,aromatic (PhLac,3-(5-isobutyl-1,2,4-oxadiazolylmethoxy)PhLac); MS(FAB): 1103(M+1).

EXAMPLE 23

Cyclo[MeLeu-Lac-MeLeu-(3-(5-(2,6-difluorophenyl)-1,2,4-oxadiazolyl)-methoxy)PhLac-MeLeu-Lac-MeLeu-PhLac] (Compound Code No. PF1022-311 substance)

A mixture of PF1022 E substance (250 mg), potassium carbonate (108 mg), sodium iodide (47.0 mg), 3-(5-(2,6-difluorophenyl)-1,2,4-oxadiazoly) methyl chloride (210 mg) and acetone (5 ml) was stirred at room temperature for 2 days. The reaction solution so obtained was diluted with ethyl acetate (50 ml), washed with water (30 ml) containing 2N hydrochloric acid (1 ml) and then with an aqueous saturated sodium chloride solution (30 ml) and further dried over anhydrous sodinm sulfate. The dried solution was concentrated under a reduced pressure, and the residue obtained was purified by a silica gel column chromatography (eluted with chloroform-ethyl acetate=8:1), to yield the titled compound (270 mg) as white powder.

$[\alpha]_D$=−88.4° (c=0.11,MeOH); $^1$H-NMR(CDCl$_3$): δ=0.75–1.1(27H,m), 1.2–1.82(15H,m), 2.7–3.22(16H,m), 4.48(1H,m), 5.06–5.74(9H,m), 6.95–7.38(11H,m), 7.59(1H, tt,J=5.9,8.2 Hz); MS(FAB): 1159(M+1).

EXAMPLE 24

Cyclo[MeLeu-Lac-MeLeu-(furfuryloxy)PhLac-MeLeu-Lac-MeLeu-PhLac] (Compound Code No. PF1022-312 substance)

PF1022 E substance (306 mg) was dissolved in THF (6 ml), and to the resulting solution were added, under ice-cooling, triphenylphosphine (83.2 mg), DEAD (0.049 ml) and furfuryl alcohol (0.027 ml). The resultant mixture was stirredat roomtemperature for 2.5hours. Underice-cooling again, triphenyl phosphine, DEAD and furfuryl alcohol, each in the same amount as above, were added to the resulting reaction solution, followed by further stirring at room temperature for 2 hours. Then, isopropylether and ethyl acetate were added to the reaction solution so obtained, and insoluble triphenylphosphine oxide so deposited was filtered off. The solvent was evaporated off from the solution under a reduced pressure. The residue was purified by a preparative reverse phase liquid chromatography using ODS, thus to afford the titled compound (168 mg; 50.6%) as white powder.

$[\alpha]_D$=−92.6° (c=0.11,MeOH); NMR(CDCl$_3$): δ=0.80–1.05(m,27H, (27H,m, δ-CH$_3$(Leu), δ-CH$_3$(Lac)), 1.39(3H,m, β-CH$_3$(Lac)), 1.47–1.76(12H,m, β-CH$_2$, γ-CH (Leu)), 2.73–3.02(12H,m,NMe), 3.055–3.15(4H,m, β-CH$_2$ (PhLac), 4.47–5.68(8H,m, α-CH)), 4.97(2H,s,OCH$_2$ (furfuryl)), 6.40(2H,m,C=CH—CH=CH—O(furfuryl)), 6.89,7.15(each 2H, each d, each J=0.77,aromatic (furfuryloxyPhLac)), 7.27(5H,m,aromatic(PhLac)), 7.44 (1H,d,J=0.14,C=CH—CH=CH—O); MS(FAB): 1045 (M+1).

EXAMPLE 25

Cyclo[MeLeu-Lac-MeLeu-(tetrahydrofurfuryloxy) PhLac-MeLeu-Lac-MeLeu-PhLac] (Compound Code No. PF1022-313 substance)

PF1022 E substance (202 mg) was dissolved in THF (4 ml), and to the resulting solution were added, under ice-cooling, triphenylphosphine (164 mg), DEAD (0.097 ml) and tetrahydrofurfuryl alcohol (0.12 ml). The resultant mixture was stirred at room temperature for 94 hours and then at 50° C. for 23 hours. Isopropylether and ethyl acetate were added to the resulting reaction solution, and insoluble triphenylphosphine oxide so deposited was removed from the solution by filtration. The solvent was evaporated off from the solution under a reduced pressure. The residue was purified by a preparative reverse phase liquid chromatography using ODS, to afford the titled compound (110 mg; 45.6%) as white powder.

$[\alpha]_D$=−96.0° (c=0.10,MeOH); NMR(CDCl$_3$): δ=0.80–1.04(m,27H,(27H,m, δ-CH$_3$(Leu), β-CH$_3$(Lac)), 1.39(3H,m, β-CH$_3$(Lac)), 1.26–2.14(14H,m,CHOCH$_2$ CH$_2$CH$_2$(tetrahydrofurfuryl), β-CH$_2$, γ-CH(Leu)), 2.73–2.82(12H,m,NMe), 3.01–4.33(11H,m, β-CH$_2$(PhLac, tetrahydrofurfuryloxyPhLac)), OCH$_2$, CHOCH$_2$CH$_2$ CH$_2$(tetrahydrofurfuryl)), 4.47–5.68(8H,m, α-CH), 6.83, 7.12(each 2H, each d, each J=0.77,aromatic (tetrahydrofurfuryloxyPhLac)), 7.27(5H,m,aromatic (PhLac)); MS(FAB): 1049(M+1).

EXAMPLE 26

Cyclo[MeLeu-Lac-MeLeu-(2-picolyloxy)PhLac-MeLeu-Lac-MeLeu-PhLac] (Compound Code No. PF1022-314 substance)

PF1022 E substance (200 mg) was dissolved in acetone (4 ml), and to the resulting solution were added, cesium carbonate (169 ml), a solution of 2-picolyl chloride (532 mg) in dimethylformamide (9 ml) and sodium iodide(30 mg). The resultant mixture was refluxed for 5 hours and then stirred further at room temperature for 15.5 hours. Ethyl acetate was added to the resulting reaction solution. The mixture obtained was washed with water, a 5% aqueous potassium hydrogen sulfate solution and a 7% aqueous sodium chloride solution (20 ml each), successively, and dried over anhydrous magnesium sulfate. After the solvent was removed from the dried solution by evaporated under a reduced pressure, and the residue was purified by a silica gel column chromatography (eluted with n-hexane-ethyl acetate=3:2~2:1), to afford the titled compound (167 mg; 76.5%) as white powder. $[\alpha]_D$=−87.2° (c=0.11,MeOH); NMR(CDCl$_3$): δ=0.80–1.04(27H,m, δ-CH$_3$(Leu), β-CH$_3$ (Lac)), 1.38(3H,m, β-CH$_3$(Lac)), 1.47–1.76(12H,m, β-CH$_2$, γ-CH(Leu)), 2.72–3.01(12H,m,NMe), 3.05–3.16(4H,m, β-CH$_2$(PhLac)), 4.45–5.67(8H,m, α-CH), 5.17(2H,s,OCH$_2$ (2-picolyloxy)), 6.91,7.16(each 2H, each d, each J=0.84, aromatic((2-picolyloxy)PhLac)), 7.25(6H,m,aromatic (PhLac,2-picolyl)), 7.51(1H,d,J=0.76,aromatic(2-picolyl)), 7.70(1H,t,J=0.76,aromatic(2-picolyl)), 8.60(d,1H,J=0.46, aromatic(2-picolyl)); MS(FAB): 1056(M+1).

EXAMPLE 27

Cyclo[MeLeu-Lac-MeLeu-(3-picolyloxy)PhLac-MeLeu-Lac-MeLeu-PhLac] (Compound Code No. PF1022-315 substance)

3-Picolyl chloride hydrochloride (1.0 g) was added to a mixture of methylene chloride (30 ml) and an aqueous saturated sodium hydrogen carbonate solution (30 ml), followed by separating the aqueous and organic layers. The organic layer so separated was dried over anhydrous sodium sulfate and then concentrated under a reduced pressure. To the resulting residue were added PF1022 E substance (501 mg), cesium carbonate (676 mg), sodium iodide (77.5 mg), acetone (8 ml) and DMF (4 ml). The resultant mixture was stirred at 70° C. for 18 hours, and then at 90° C. for 4.5 hours. The reaction solution obtained was allowed to cool to room temperature, then diluted with ethyl acetate (50 ml), washed with water (40 ml), a 0.1N hydrochloric acid (40 ml) and an aqueous saturated sodium chloride solution (40 ml), successively, and further dried over anhydrous sodium sulfate. The dried solution was concentrated under a reduced pressure, and the residue was purified by a silica gel column chromatography (eluted with n-hexane-ethyl acetate-1:1~ethyl acetate), to yield the titled compound (137 mg).

$[\alpha]_D$=−84.9° (c=0.12,MeOH); $^1$H-NMR(CDCl$_3$): δ=0.72–1.08(27H,m), 1.2–1.86(15H,m), 2.7–3.22(16H,m), 4.48(1H,m), 5.0–5.73(9H,m), 6.86–6.94(2H,m), 7.14–7.36 (10H,m), 7.76(1H,d,J=7.6 Hz), 8.59(1H,d,J=3.7 Hz,8.68 (1H,s); MS(FAB): 1056(M+1).

EXAMPLE 28

Cyclo[MeLeu-Lac-MeLeu-(4-picolyloxy)PhLac-MeLeu-Lac-MeLeu-PhLac] (Compound Code No. PF1022-316 substance)

4-Picolyl chloride hydrochloride (775 g) was added to a mixture of methylene chloride (30 ml) and an aqueous saturated sodium hydrogen carbonate solution (30 ml), followed by separating the aqueous and organic layers. The organic layer so separated was dried over anhydrous sodium sulfate and then concentrated under a reduced pressure. To the resulting residue were added PF1022 E substance (251 mg), cesium carbonate (220 mg), sodium iodide (38.1 mg), acetone (15 ml) and DMF (5 ml). The resultant mixture was stirred at 80° C. for 8.5 hours, and then at room temperature overnight. The reaction solution obtained was diluted with ethyl acetate (50 ml), washed with an aqueous saturated sodium hydrogen carbonate solution (50 ml), a 0.2N hydrochloric acid (40 ml) and an aqueous saturated sodium chloride solution (40 ml), successively, and then dried over anhydrous sodium sulfate. The dried solution was concentrated under a reduced pressure. The residue was purified by a silica gel column chromatography (eluted with n-hexane-ethyl acetate-2:1ethyl acetate), to yield the titled compound (70.4 mg) as white powder.

$[\alpha]_D = -84.4°$ (c=0.11,MeOH); $^1$H-NMR(CDCl$_3$): δ=0.76–1.06(27H,m), 1.2–1.82(15H,m), 2.72–3.22(16H,m), 4.48(1H,m), 5.02–5.72(9H,m), 6.84–6.93(2H,m), 7.12–7.35 (7H,m), 7.35(2H,d,J=5.4 Hz), 8.62(2H,d,J=5.4 Hz); MS(FAB): 1056(M).

EXAMPLE 29

Cyclo[MeLeu-Lac-MeLeu-(6-chloro-3-picolyloxy)PhLac-MeLeu-Lac-MeLeu-PhLac] (Compound Code No. PF1022-317 substance)

PF1022 E substance (178 mg) was dissolved in a mixture of DMF (1.5 ml) and acetone (5 ml), and to the resulting solution were added 2-chloro-4-chloromethylpyridine (97 mg) and cesium carbonate (194 mg). The resultant mixture was stirred under reflux for 4 hours. Ethyl acetate and water were added to the reaction solution obtained, and the organic layer so separated was washed with water and dried over magnesium sulfate. The solvent was removed from the dried solution by evaporation, and the residue was purified by a silica gel chromatography, affording the titled compound (162 mg; 76%).

$[\alpha]_D = -91.1°$ (c=0.09,MeOH); NMR(CDCl$_3$): δ=0.72–1.07(27H,m, δ-CH$_3$(MeLeu), β-CH$_3$(Lac)), 1.23–1.81(15H, β-CH$_2$, γ-CH(MeLeu), β-CH$_3$(Lac)), 2.48–3.17(16H,m,NMe(MeLeu), OCH$_2$(picolyl), β-CH$_2$ (PhLac,(6-chloro-3-picolyloxy)PhLac), 4.45–5.69(8H,m, α-CH), 6.78–6.84(2H,m,aromatic((6-chloro-3-picolyloxy) PhLac)), 7.10–7.31(7H,m,aromatic(PhLac,(6-chloro-3-picolyloxy)PhLac), 8.38(1H,m,H-2(picolyl), 8.40(2H,dd,H-4,5(picolyl)).

EXAMPLE 30

Cyclo[MeLeu-Lac-MeLeu-(2-(1-N-methyl-1,4,5,6-tetrahydropyrimidyl)methoxy)PhLac-MeLeu-Lac-MeLeu-PhLac] (Compound Code No. PF1022-318 substance)

Cyclo[MeLeu-Lac-MeLeu-(H$_2$NCSCH$_2$O)PhLac-MeLeu-Lac-MeLeu-PhLac] (403 mg) was dissolved in acetone (20 ml), and to the resulting solution was added methyl iodide (0.25 ml). The resultant mixture was stirred at 30° C. for 24 hours and then at 40° C. for 1 day. The reaction solution obtained was concentrated and the residue was dissolved in benzene (8 ml), and to this solution were added N-methyl-1,3-propanediamine (41 μl) and a 10% methanolic solution of hydrogen chloride (0.15 ml). The resultant mixture was stirred at room temperature for 1 day. Then, ethanol (5 ml) was added and the mixture so obtainedwas furtherstirred at 80° C. for 1 hour. The reaction solution as formed was allowed to cool to room temperature, then diluted with ethyl acetate (50 ml), washed with an aqueous saturated sodium hydrogen carbonate solution (30 ml) and with an aqueous saturated sodium chloride solution (30 ml), in order, and further was dried over anhydrous sodium sulfate. The dried solution was concentrated under a reduced pressure, and the residue was purified by a silica gel column chromatography (eluted with chloroform-methanol= 30:1~10:1), thus to afford the titled compound (133 mg).

$[\alpha]_D = -72.1°$ (c=0.10,MeOH); $^1$H-NMR(CDCl$_3$): δ=0.7–2.0(46H,m), 2.76–3.60(23H,m), 4.47(1H,m), 5.0–5.72(9H,m), 7.10–7.36(9H,m); MS(FAB): 1075(M+1).

EXAMPLE 31

Cyclo[MeLeu-Lac-MeLeu-(3-(5-isopropyl-1,2,4-oxadiazolyl)-methoxy)PhLac-MeLeu-Lac-MeLeu-PhLac] (Compound Code No. PF1022-341 substance)

PF1022 E substance (300 mg) was dissolved in acetone (6 ml), and to the solution were added potassium carbonate (215 mg), sodium iodide (233 mg) and 3-chloromethyl-5-isopropyl-1,2,4-oxadiazole (250 mg). The resultant mixture was stirred at 40° C. for 30 hours. After the solvent was removed from the resulting reaction solution by evaporation, ethyl acetate and water were added to the residue. The organic layer so separsted was dried over magnesium sulfate. The solvent was removed by evaporation, and the residue was purified by a silica gel chromatography, affording the titled compound (241 mg; 71%).

$[\alpha]_D = -88.8°$ (C=0.12,MeOH); NMR(CDCl$_3$): δ=0.83–1.04(24H,m, δ-CH$_3$(MeLeu)), 1.43(6H,d,J=7.0, CH$_3$(isopropyl)), 1.36–1.76(18H,m, β-CH$_3$(Lac), β-CH$_2$ (MeLeu), γ-CH(MeLeu)), 2.72–3.31(16H,m,N—Me (MeLeu), β-CH$_2$(PhLac)), 3.26(1H,m,CH(isopropyl)), 4.50–5.67(8H,m, α-CH(MeLeu,Lac,PhLac), 5.12(2H,s, OCH$_2$), 6.93–6.96(2H,m,aromatic), 7.15–7.29(7H,m, aromatic); MS(FAB): 1089(M+1).

EXAMPLE 32

Cyclo[MeLeu-Lac-MeLeu-(3-(5-cyclohexyl-1,2,4-oxadiazolyl)-methoxy)PhLac-MeLeu-Lac-MeLeu-PhLac] (Compound Code No. PF1022-343 substance)

PF1022 E substance (300 mg) was dissolved in acetone (6 ml), and to the solution were added potassium carbonate (214 mg), sodium iodide (233 mg) and 3-chloromethyl-5-cyclohexyl-1,2,4-oxadiazole (312 mg). The resultant mixture was stirred at 40° C. for 20 hours. After the solvent was removed from the reaction solution by evaporation, ethyl acetate and water were added to the residue. The organic layer so separated was dried over magnesium sulfate. The solvent was removed by evaporation, and the residue was purified by a silica gel chromatography, affording the titled compound (260 mg; 74%).

$[\alpha]_D = -81.0°$ (c=0.11,MeOH); NMR(CDCl$_3$): δ=0.83–1.05(24H,m, β-CH$_3$(MeLeu)), 1.26–2.13(28H,m, β-CH₃(Lac), β-CH₂(MeLeu), γ-CH(MeLeu), (CH₂)₅ (cyclohexyl)), 2.72–3.15(17H,m,N—Me(MeLeu), β-CH₂ (PhLac), CH(cyclohexyl)), 4.50–5.67(8H,m, α-CH(MeLeu, Lac,PhLac), 5.12(2H,s,OCH₂), 6.93–6.96(2H,m,aromatic), 7.15–7.29(7H,m,aromatic); MS(FAB): 1129(M+1).

EXAMPLE 33

Cyclo[MeLeu-Lac-MeLeu-(NCCH₂O)PhLac]₂

A mixture of PF1022 H substance (201 mg), potassium carbonate (144 mg), bromoacetonitrile (0.15 ml) and acetone (5 ml) was stirred at room temperature for 2.5 hours. The reaction solution so obtained was diluted with ethyl acetate (25 ml), washed with water (10 ml) containing 2N hydrochloric acid (2 ml), and further dried over anhydrous sodium sulfate. The dried solution was concentrated under a reduced pressure, and the residue was purified by a silica gel column chromatography (eluted with chloroform-ethyl acetate=4:1~1:1), to afford the titled compound (210 mg) as white powder. ¹H-NMR(CD₃OD): δ=0.78–1.06(27H,m), 1.1–1.9(15H,m), 2.78–3.22(16H,m), 4.94(1H,m), 5.13–5.83 (7H,m), 6.95–7.04(4H,m), 7.25–7.35(4H,m).

EXAMPLE 34

Cyclo[MeLeu-Lac-MeLeu-(BocNHCH₂CH₂O) PhLac]₂

Cyclo[MeLeu-Lac-MeLeu-(NCCH₂O)PhLac]₂ (9.5 g) as obtained in Example 33 was dissolved in ethanol (100 ml), and to the solution were added 10% Pd/carbon (1.0 g) and concentrated hydrochloric acid (1.5 ml). The resultant mixture was subjected to reduction with hydrogen under a medium pressure in a Parr-reduction vessel for 15 hours (for the formation of amino group by reduction of cyano group). After the catalyst was removed from the reaction solution by filtration, the solvent was evaporated off. The resulting residue was dissolved in a mixture of dioxane (200 ml) and water (200 ml). To the resulting solution were added DiBoc reagent (di-t-butyldicarboxylate) (15 g) and triethylamine (6 ml). The resultant mixture was stirred at room temperature for 15 hours. Ethyl acetate and water were added to the reaction solution as formed. The organic layer so separated was washed with water and dried over magnesium sulfate. The solvent was removed from the dried solution by evaporation, and the residue was purified by a silica gel chromatography, thus yielding the titled compound (3.67 g; 34%)

NMR(CDCl₃): δ=0.79–1.04(27H, δ-CH₃(MeLeu), β-CH₃ (Lac)), 1.31–1.77(33H,m, δ-CH₂, γ-CH(MeLeu), β-CH₃ (Lac), BocNH), 2.73–3.08(16H,m,NMe(MeLeu), β-CH₂ ((BocNHCH₂CH₂O)PhLac)), 3.51(2H,m,NHCH₂CH₂O), 3.97(2H,t,NHCH₂CH₂O), 4.44–5.68(8H,m, α-CH), 678–6.84(4H,m,aromatic), 7.10–7.31(4H,m,aromatic).

EXAMPLE 35

Cyclo[MeLeu-Lac-MeLeu-(CbzNHCH₂CH₂O) PhLac]₂

Cyclo[MeLeu-Lac-MeLeu-(NCCH₂O)PhLac]₂ (2.02 g) as obtained in Example 33 was dissolved in ethanol (50 ml), and to the solution were added concentrated hydrochloric acid (0.5 ml) and 10% Pd/carbon (204 mg). The resultant mixture was subjected to catalytic reduction in a Parr-reduction vessel (at 45 psi.) overnight. The catalyst was removed from the reaction solution by filtration, and to the filtrate obtained were added chloroform (100 ml) and an aqueous saturated sodium hydrogen carbonate (50 ml), followed by separating the aqueous and organic layers. The aqueous layer was again extracted with chloroform (50 ml). The organic layers so obtained in the two extraction steps were combined together and dried over anhydrous sodium sulfate. Then, the dried solution was concentrated to dryness under a reduced pressure.

The crude product of the free amino compound thus obtained (2.21 g) was dissolved in methylene chloride (50 ml), and to the solution were added, under ice-cooling, triethylamine (0.8 ml) and benzyloxycarbonyl chloride (0.7 ml). The resultant mixture was stirred under ice-cooling for 2.5 hours. The reaction solution obtained was diluted with chloroform (50 ml), washed with a 10% sodium chloride solution, and was dried over anhydrous sodium sulfate. The dried solution was concentrated under a reduced pressure. The residue obtained was purified by a silica gel column chromatography (eluted with ethyl acetate-hexane= 1:2~2:1), thus to yield the titled compound (693 mg) as white powder.

¹H-NMR(CD₃OD): δ=0.75–1.05(27H,m), 1.38(3H,t,J= 7.0 Hz), 1.3–2.0(12H,m), 2.81,2.87,2.90,2.99(each 3H, each s), 2.9–3.2(4H,m), 3.49(4H,t,J=5.5 Hz), 3.99(4H,t,J=5.5 Hz), 4.75(1H,dd,J=4.6,10.8 Hz), 5.07(4H,s), 5.1–5.8(7H,m), 6.87(4H,d,J=8.3 Hz), 7.19(4H,d,J=8.3 Hz), 7.2–7.4(10H,m); MS(SIMS): 1335(M+1).

EXAMPLE 36

Cyclo[MeLeu-Lac-MeLeu-((CH₃)₂NCH₂CH₂O) PhLac]₂ (Compound Code No. PF1022-262 substance)

Cyclo[MeLeu-Lac-MeLeu-(CbzNHCH₂CH₂O)PhLac]₂ (300 mg) as obtained in Example 35 was dissolved in ethanol (5 ml), and to the solution were added 1N hydrochloric acid (0.66 ml) and 10% Pd/carbon (30 mg). The resultant mixture was stirred under hydrogen atmosphere at atmospheric pressure and at room temperature for 2 hours. After adding aqueous 37% solution of formaldehyde (0.71 ml) to the resulting reaction solution, the latter was stirred overnight, followed by further adding aqueous 37% solution of formaldehyde (3.6 ml) thereto. The resulting mixture was stirred at room temperature overnight. The catalyst was removed from the resulting reaction solution by filtration, and the solvent was removed from the solution by evaporation. Then, to the resultant residue were added ethyl acetate and an aqueous saturated sodium hydrogen carbonate solution, followed by separating the aqueous layer and organic layers. The organic layer so separated was dehydrated by anhydrous magnesium sulfate. The solvent was evaporated off from the dried solution, and the residue was purified by a silica gel chromatography, thus affording the titled compound (118 mg; 48%).

[α]$_D$=−83.3° (c=0.21,MeOH); NMR(CDCl₃): δ=0.80–1.05(24H,m, δ-CH₃(MeLeu)), 1.26–2.02(30H,m, β-CH₃(Lac), β-CH₂(MeLeu), γ-CH(MeLeu), (CH₃)₂N), 2.74–3.06(20H,m,N—Me(MeLeu), β-CH₂(PhLac), OCH₂CH₂N), 4.50, 5.04–5.65(8H,m,α-H(MeLeu,Lac, PhLac), 6.78–6.90(2H,m,aromatic), 7.16–7.18(7H,m, aromatic); MS(SIMS): 1123(M+1).

EXAMPLE 37

Cyclo[MeLeu-Lac-MeLeu-((C₂H₅)₂NHCH₂CH₂O) PhLac]₂ (Compound Code No. PF1022-263 substance)

Cyclo[MeLeu-Lac-MeLeu-(CbzNHCH₂CH₂O)PhLac]₂ (312.1 mg) and 10% Pd/carbon (33.7 mg) were mixed with ethanol (5 ml) containing 2N hydrochloric acid (0.3 ml), and the mixture was stirred under hydrogen atmosphere for 5 hours. To the resulting reaction solution, under ice-cooling, 90% aqueous acetaldehyde (6 ml) was added dropwise. The resultant mixture was stirred overnight under the same reduction condition as that above, while the temperature was slowly elevated up to room temperature. The catalyst was removed from the resulting reaction solution by filtration and the filtrate so obtained was concentrated under a reduced pressure. The residue was purified by a preparative TLC (developed with chloroform-methanol=20:1), to yield the titled compound (204 mg) as white powder.

$[\alpha]_D$=−88.0° (c=0.22,MeOH); $^1$H-NMR(CDCl$_3$): δ=0.78–1.10(39H,m), 1.2–1.84(15H,m), 2.64(8H,q,J=7.3 Hz), 2.7–3.14(20H,m), 4.01(4H,t,J=6.2 Hz), 4.47(1H,m), 5.08(1H,q,J=7.0 Hz), 5.17(1H,dd,J=5.4,9.7 Hz), 5.28–5.68 (5H,m), 6.81(4H,d,J=8.5 Hz), 7.13(4H,d,J=8.5 Hz); MS(SIMS): 1179(M+1).

EXAMPLE 38

Cyclo[MeLeu-Lac-MeLeu-(MorCH$_2$CH$_2$O)PhLac]$_2$ (Compound Code No. PF1022-266 substance)

Cyclo[MeLeu-Lac-MeLeu-(CbzNHCH$_2$CH$_2$O)PhLac]$_2$ (290 mg) was mixed with ethanol (5 ml) containing 2N hydrochloric acid (0.3 ml), and the mixture was stirred under hydrogen atmosphere in the presence of 10% Pd-carbon (30 mg) for 2.5 hours. The catalyst was removed from the reaction solution by filtration and the filtrate so obtained was concentrated under a reduced pressure. To the residue were added potassium carbonate (180 mg), sodium iodide (40 mg) and bis-bromoethyl ether (0.07 ml). The resultant mixture was dissolved in DMF (5 ml), followed by stirring at 80° C. for 5 hours. Then, the resulting reaction solution was allowed to cool to room temperature and then was added with water (30 ml). The mixture so obtained was extracted with chloroform twice (firstly 50 ml and secondly 20 ml of chloroform), and the extracts obtained were combined together and dried over anhydrous sodium sulfate. The solution so dried was concentrated under a reduced pressure. The residue was purified by a silica gel column chromatography (eluted with chloroform-methanol=20:1), thus affording the titled compound (181 mg) as white powder.

$[\alpha]_D$=−84.3° (c=0.19,MeOH); $^1$H-NMR(CDCl$_3$): δ=0.70–1.10(27H,m), 1.2–2.0(15H,m), 2.57(8H,t,J=4.5 Hz), 2.7–3.15(20H,m), 3.73(8H,t,J=4.5 Hz), 4.07(4H,t,J=5.6 Hz), 4.47(1H,m), 5.07(1H,q,J=7.0 Hz), 5.18(1H,dd,J=5.5, 10.0 Hz), 5.30–5.66(5H,m), 6.81(4H,d,J=8.4 Hz), 7.14(4H, d,J=8.4 Hz); MS(SIMS): 1207(M+1).

EXAMPLE 39

Cyclo[MeLeu-Lac-MeLeu-(3-(5-isobutyl-1,2,4-oxadiazolyl)-methoxy)PhLac]$_2$ (Compound Code No. PF1022-330 substance)

PF1022 H substance (500 mg) was dissolved in a mixture of acetone (10 ml) and DMF (1 ml), and to the solution were added potassium carbonate (352 mg), 3-chloromethyl-5-isobutyl-1,2,4-oxadiazole (442 mg) and sodium iodide (382 mg). The resultant mixture was subjected to the reaction at room temperature for 24 hours and then at 50° C. for 31 hours. Ethyl acetate (50 ml) and water (50 ml) were added to the resulting reaction solution to separate the aqueous and organic layers. The organic layer so separated was dried over anhydrous magnesium sulfate. The solvent was removed from the dried solution by evaporation under a reduced pressure, and the residue was purified by a silica gel column chromatography (eluted with chloroform ethyl acetate= 2:1~1:1), thus to afford the titled compound (467 mg; 72.8%) as white powder.

$[\alpha]_D$=−78.1° (c=0.11,MeOH); NMR(CDCl$_3$): δ=0.80–1.05(33H,m, δ-CH$_3$(MeLeu), β-CH$_3$(Lac), CH(CH$_3$)CH$_2$CH$_3$(isobutyl)), 1.36–1.41(9H,m, β-CH$_3$ (Lac), CH(CH$_3$)CH$_2$CH$_3$(isobutyl)), 1.49–2.01(16H,m, β-CH$_2$, γ-CH (MeLeu), CH(CH$_3$)CH$_2$CH$_3$(isobutyl)), 2.63–3.03(12H,m,NMe), 4.45–5.62(8H,m, α-CH), 5.13(4H, s,OCH$_2$), 6.93, 7.16(each 2H, each d, each J=0.77,aromatic), 6.94, 7.17(each 2H, each d, each J=0.67,aromatic); MS (FAB): 1257(M+1).

EXAMPLE 40

Cyclo[MeLeu-Lac-MeLeu-(3-(5-(2,6-difluorophenyl)-1,2,4-oxadiazolyl)-methoxy)PhLac]$_2$ (Compound Code No. PF1022-331 substance)

A mixture of PF1022 H substance (251 mg), potassium carbonate (171 mg), sodium iodide (103 mg), 3-(5-(2,6-difluorophenyl)-1,2,4-oxadiazolyl)-methyl chloride (358 mg) and acetone (6 ml) was stirred at room temperature for 64 hours. The reaction solution so obtained was diluted with ethyl acetate (50 ml), washed with water (30 ml) containing 2N hydrochloric acid (1 ml) and then with an aqueous saturated sodium chloride solution (30 ml), followed by drying over anhydrous sodium sulfate. The dried solution was concentrated under a reduced pressure, and the residue was purified by a silica gel column chromatography (chloroform-ethyl acetate=10:1~1:1), thus to afford the titled compound (311 mg).

$[\alpha]_D$=−84.4° (c=0.11,MeOH); $^1$H-NMR(CDCl$_3$): δ=0.70–1.08(27H,m), 1.2–1.84(15H,m), 2.7–3.2(16H,m), 4.48(1H,m), 5.02–5.72(11H,m), 6.86–7.36(12H,m), 7.58 (2H,t t,J=5.9,8.2 Hz); MS(FAB): 1369(M+1).

EXAMPLE 41

Cyclo[MeLeu-Lac-MeLeu-(tetrahydrofurfuryloxy) PhLac]$_2$ (Compound Code No. PF1022-333 substance)

PF1022 H substance (150 mg) was dissolved in THF (3 ml), and to the solution were added, under ice-cooling, tetrahydrofurfuryl alcohol (0.15 ml), triphenylphosphine (281 mg) and DEAD (0.17 ml). The resultant mixture was stirred at room temperature for 3.5 hours and then at 50° C. for 3 hours and finally at room temperature for 16 hours. The resulting reaction solution was concentrated under a reduced pressure to remove the solvent. To the residue was added isopropylether to deposit triphenylphosphine oxide. The deposited material was removed by filtration, and the resulting filtrate was concentrated under a reduced pressure to remove the solvent. The residue so obtained was purified by a preparative reverse phase liquid chromatography using ODS, thus to afford the titled compound (62 mg; 35 3%) as white powder.

$[\alpha]_D$=−91.6° (c=0.11,MeOH); NMR(CDCl$_3$): δ=0.80–1.46(27H,m, δ-CH$_3$(Leu), β-CH$_3$(Lac)), 1.35–1.46 (3H,m, β-CH$_3$(Lac)), 1.49–2.11(16H,m,tetrahydrofurfuryl-4-CH$_2$, β-CH$_2$, γ-CH(Leu)), 2.73–3.02(12H,m,NMe), 3.04–3.08(4H,m, β-CH$_2$(tetrahydrofurfuryloxy)PhLac)), 3.79–4.32(14H,m,tetrahydrofurfuryl-2,3,5-CH$_2$, OCH$_2$CH(tetrahydrofurufuryl)), 4.67–5.65(8H,m, α-CH), 6.83,7.12(each 2H, each d, each J=0.77,aromatic (tetrahydrofurfuryloxyPhLac), 6.84,7.13(each 2H, each d, each J=0.67,aromatic(tetrahydrofurfuryloxyPhLac)); MS(FAB): 1149(M+1).

EXAMPLE 42

Cyclo[MeLeu-Lac-MeLeu-(2-picolyloxy)PhLac]$_2$ (Compound Code No. PF1022-334 substance)

PF1022 H substance (300 mg) was dissolved in acetone (6 ml), and to the solution were added a solution of 2-picolyl chloride (787 mg) in DMF (12 ml), cesium carbonate (500 mg) and sodium iodide (87 mg). The resultant mixture was refluxed for 2 hours and then further stirred at room temperature for 17 hours. The resulting reaction solution, after addition of ethyl acetate (50 ml) thereto, was washed with a 10% aqueous sodium chloride solution and then with a 5% aqueous sodium sulfite solution (50 ml, each) and further dried over anhydrous magnesium sulfate. The solvent was removed from the dried solution by evaporation under a reduced pressure. The residue was purified by a silica gel column chromatography (eluted with chloroform-ethyl acetate=5:1~ethyl acetate), thus to afford the titled compound (175 mg; 50%) as white powder.

$[\alpha]_D$=−82.6° (c=0.12,MeOH); NMR(CDCl$_3$): δ=0.80–0.96(24H,m, δ=CH$_3$(Leu)), 1.02(3H,t,J=1.4, β-CH$_3$ (Lac)), 1.38(3H,m, β-CH$_3$(Lac)), 1.50–1.83(12H,m, β-CH$_2$, γ-CH(Leu)), 2.73–3.01(12H,m,NMe), 3.02–3.09(4H,m, β-CH$_2$(PhLac)), 4.45–5.65(8H,m, α-CH) 5.17(4H,s,OCH$_2$ (2-picolyloxy)), 6.91,7.15(each 4H, each d, each J=0.73, aromatic((2-picolyloxy)PhLac), 7.21–7.27(2H,m,aromatic (2-picolyl)), 7.47–7.52(2H,m,aromatic(2-Picolyl)), 7.68–7.77(2H,m,aromatic(2-Picolyl)), 8.59–8.61(2H,m, aromatic(2-Picolyl)); MS(FAB): 1163(M+1).

EXAMPLE 43

Cyclo[MeLeu-Lac-MeLeu-(3-(5-isopropyl-1,2,4-oxadiazolyl)-methoxy)PhLac]$_2$ (Compound Code No. PF1022-345 substance)

PF1022 H substance (400 mg) was dissolved in acetone (8 ml), and to the solution were added potassium carbonate (563 mg), sodium iodide (611 mg) and 3-chloromethyl-5-isopropyl-1,2,4-oxadiazole (655 mg). The resultant mixture was stirred at 40° C. for 48 hours. The solvent was removed from the reaction solution by evaporation, and ethyl acetate and water were added to the residue. The organic layer so separated was dried over magnesium sulfate. The solvent was removed from the dried solution by evaporation. The residue was purified by a silica gel chromatography, followed by a preparative reverse phase liquid chromatography using ODS, thus to afford the titled compound (137 mg; 27.3%)

$[\alpha]_D$=−88.6° (c=0.1,MeOH); NMR(CDCl$_3$): δ=0.81–1.04 (24H,m, δ-CH$_3$(MeLeu)), 1.43(12H,d,J=7.0,CH$_3$ (isopropyl)), 1.35–1.75(18H,m, β-CH$_3$(Lac), β-CH$_2$ (MeLeu), γ-CH(MeLeu)), 2.72–3.08(16H,m,N—Me (MeLeu), β-CH$_2$(PhLac)), 3.26(2H,m,CH(isopropyl)), 4.50, 5.02–5.70(8H,m, α-H(MeLeu,Lac,PhLac)), 5.11(4H,s, OCH$_2$), 6.91–6.96(2H,m,aromatic), 7.15–7.19(7H,m, aromatic); MS(FAB): 1229(M+1).

EXAMPLE 44

Cyclo[MeLeu-Lac-MeLeu-(3-(5-cyclohexyl-1,2,4-oxadiazolyl)-methoxy)PhLac]$_2$ (Compound Code No. PF1022-347 substance)

PF1022 H substance (400 mg) was dissolved in a mixture of acetone (8 ml) and DMF (4 ml), and to the resulting solution were added potassium carbonate (563 mg), sodium iodide (611 mg) and 3-chloromethyl-5-cyclohexyl-1,2,4-oxadiazole (818 mg). The resultant mixture was stirred at 40° C. for 48 hours, followed by removing the solvent from the reaction solution by evaporation. Ethyl acetate and water were added to the residue obtained, and the organic layer as separated was dried over magnesium sulfate. The solvent was removed from the dried solution by evaporation. The residue was purified by a silica gel chromatography, followed by a preparative reverse phase liquid chromatography using ODS, thus to afford the titled compound (135 mg; 25%).

$[\alpha]_D$=−62.7° (c=0.21,MeOH); NMR(CDCl$_3$): δ=0.91–1.15(24H,m, δ-CH$_3$(MeLeu)), 1.30–2.25(38H,m,β-CH$_3$(Lac), β-CH$_2$(MeLeu), γ-CH(MeLeu), (CH$_2$)$_5$ (cyclohexyl)), 2.50–3.25(18H,m,N—Me(MeLeu), β-CH$_2$ (PhLac), CH(cyclohexyl)), 4.20,4.50,5.35–5.75(8H,m, α-CH(MeLeu,Lac,PhLac)), 5.12(4H,s,OCH$_2$), 6.95–7.05 (2H,m,aromatic), 7.23–7.27(7H,m,aromatic); MS(FAB): 1309(M+1).

EXAMPLE 45

Cyclo[MeLeu-Lac-MeLeu-PhLac-MeLeu-Lac-MeLeu-(NH$_2$CO)PhLac] (Compound Code No. PF1022-242 substance)

(1) Synthesis of H—L—(O$_2$N)PhLac-OH

L-p-Nitrophenylalanine monohydrate (15.2 g) was dissolved in a mixture of water (230 ml), 1,4-dioxane (230 ml) and acetic acid (230 ml). To the resulting solution was added an aqueous solution of sodium nitrite (4.58 g) four times at each interval of 30 minutes at a temperature below 10° C., and the resultant mixture was allowed to undergo the reaction at that temperature for 30 minutes. After the 1,4-dioxane was evaporated from the resulting reaction solution under a reduced pressure, the pH of the residue so obtained was adjusted to the value of pH 1.0 with the addition of 1N hydrochloric acid under ice-cooling. The residue was then extracted with ethyl acetate (500 ml). The extract obtained was washed with a 20% aqueous sodium chloride solution (500 ml), then dried over anhydrous magnesium sulfate and concentrated under a reduced pressure to remove the solvent therefrom.

The resulting residue was dissolved in a 90% aqueous methanol (150 ml), and the pH of the resulting solution was adjusted to pH 12 with the addition of a 2N aqueous sodium hydroxide solution under ice-cooling, and the solution was stirred at room temperature for 1 hour. The pH of the resulting reaction solution was adjusted to pH 7.0 with the addition of a 1N hydrochloric acid under ice-cooling, and the solvent was removed from said solution by evaporation under a reduced pressure. The residue so obtained was dissolved in water (300 ml), and the pH of the solution was adjusted to pH 2.0 with the addition of a 1N hydrochloric acid under ice-cooling, after which the solution was extracted with ethyl acetate (450 ml). The extract so obtained was washed with a 10% aqueous sodium chloride solution (450 ml), then dried over anhydrous magnesium sulfate and concentrated under a reduced pressure to remove the solvent. Thus, the titled compound was obtained in a crude product form (10.7 g) as a yellow oil. This was used in the next reaction step without purification.

NMR(CD$_3$OD): δ=2.99–3.31(2H,m, β-CH$_2$), 4.39(1H,m, α-CH), 7.84(4H,dd,J=17.4,9.0,aromatic).

(2) Synthesis of H—L—(O$_2$N)PhLac-OMe

H—L—(O$_2$N)PhLac-OH (10.7 g) was dissolved in methanol (215 ml), and to the solution was added thionyl chloride (7.4 ml) under ice-cooling. The resultant mixture was allowed to undergo the reaction at room temperature for 45 minutes. The pH of the reaction solution so obtained was adjusted to pH 7.0 with addition of a 2N aqueous sodium hydroxide to the solution under ice-cooling. The solvent was removed from the solution by evaporation under a reduced pressure. The residue was dissolved in ethyl acetate (450 ml), and the solution was washed twice with water (450 ml each) and dried over anhydrous magnesium sulfate. The solvent was removed from the dried solution by evaporation under a reduced pressure, and the residue was purified by a silica gel column chromatography (eluted with toluene-ethyl acetate=6:1, v/v), thus to afford the titled compound (9.59 g; 64.2% yield, based on p-nitrophenylalanine) as white crystals.

$[\alpha]_D$=−6.79° (c 0.22,MeOH); NMR(CDCl$_3$): δ=2.97(1H, d,J=0.5,OH), 3.16(2H,ddd,J=0.4,0.7,1.4,4.9, β-CH$_2$), 3.80 (3H,s,COOMe), 4.49(1H,d t,J=0.5,0.7, α-CH), 7.77(4H,dd, J=0.8,20.4,aromatic)

(3) Synthesis of H—L—(H$_2$N)PhLac-OMe

H—L—(O$_2$N)PhLac-OMe (9.59 g) was dissolved in methanol (192 ml) under nitrogen atmosphere, and to the resulting solution were added a 10% Pd/carbon (960 mg) and acetic acid (0.2 ml). The resultant mixture was reduced with hydrogen under atmospheric pressure for 5 hours. The catalyst was removed from the reaction solution by filtration, and then the filtrate obtained was concentrated under a reduced pressure to remove the solvent, and thus to afford the titled compound in the form of a crude product (8.37 g) as white crystals. This was used directly in the next reaction step without any purification.

NMR(CDCl$_3$): δ=2.93(2H,ddd,J=0.6,0.7,1.4,3.9, β-CH$_2$), 3.27(2H,b s,NH$_2$), 3.74(3H,s,COOMe), 4.37(1H,dd,J=0.4, 0.6, α-CH), 6.79(4H,dd,J=0.8,10.0,aromatic).

(4) Synthesis of H—L—(NC)PhLac-OMe

H—L—(H$_2$N)PhLac-OMe (8.30 g) was dissolved in a 1N hydrochloric acid (83 ml), and to the solution was added dropwise an aqueous solution of sodium nitrite (3.42 g) under ice-cooling. The resultant mixture was subjected to the reaction for 30 minutes in order to convert the amino compound into the corresponding diazonium salt. The resulting reaction solution was adjusted to pH 6.5 with the addition of a 10% aqueous potassium carbonate solution. On the other hand, cuprous chloride (8.86 g) was suspended in water (35 ml), and to the suspension was added dropwise an aqueous solution of potassium cyanide (11.36 g) under ice-cooling, and the mixture so obtained was stirred for 3 hours. To the resulting aqueous solution of copper cyanide as formed was added the aqueous solution (at pH 6.5) of the diazonium salt produced as above and also was added ethyl acetate (83 ml). The resultant mixture was subjected to reaction at room temperature for 2 hours.

The reaction solution so obtained was filtered to remove insoluble material, and ethyl acetate (200 ml) was added to the filtrate to separate the aqueous and organic layers. The organic layer as separated was washed with water (400 ml) and dried over anhydrous magnesium sulfate. The solvent was removed from the dried solution by evaporation under a reduced pressure, and the residue was purified by a silica gel column chromatography (eluted with toluene-ethyl acetate=3:1, v/v), thus affording the titled compound (4.53 g; 50.0%) as a yellow oil.

NMR(CDCl$_3$): δ=2.91(1H,d,J=0.5,OH), 3.10(2H,ddd,J= 0.4,0.7,1.4,5.0, β-CH$_2$), 3.79(3H,s,COOMe), 4.47(1H,d t,J= 0.7,0.5, α-CH), 7.47(4H,dd,J=0.8,6.6,aromatic).

(5) Synthesis of H—L—(NH$_2$CO)PhLac-OMe

H—L—(NC)PhLac-OMe (4.25 g) was dissolved in methanol (42.5 ml), and to the solution were added a 30% aqueous hydrogen peroxide solution (7.05 ml) and triethylamine (4.33 ml) under ice-cooling. The resultant mixture was stirred under ice-cooling for 2 hours. Then, further two portions (4.7 ml each) of 30% aqueous hydrogen peroxide solution were added to the resulting reaction mixture at intervals of 3 hours, followed by effecting the reaction for 18 hours. The resultant reaction solution was adjusted to pH 6.9 with the addition of a 1N hydrochloric acid, followed by removing the solvent therefrom by evaporation under a reduced pressure. Thus, the titled compound was obtained in the form of a crude product as white crystals. This was used in the next reaction step without any purification.

NMR(CDCl$_3$): δ=3.04(2H,ddd,J=0.5,0.8,1.4,4.3, β-CH$_2$), 3.69(3H,s,COOMe), 4.40(1H,dd,J=0.5,0.8, α-CH), 7.56 (4H,dd,J=0.8,12.4,aromatic).

(6) Synthesis of H—L—(NH$_2$CO)PhLac-OH

H—L—(NH$_2$CO)PhLac-OMe (4.63 g) was dissolved in a mixture of acetone (93 ml) and water (46 ml), and to the resulting solution was added a 1N aqueous sodium hydroxide (31 ml) under ice-cooling. The reaction was conducted under ice-cooling for 15 hours. The resulting reaction solution was adjusted to pH 7 with the addition of a 1N hydrochloric acid and the solvent was removed from the reaction solution by evaporation under a reduced pressure. Thus, the titled compound was afforded in the form of its crude product as white crystals. This was used in the next reaction step without any purification.

(7) Synthesis of H—L—(NH$_2$CO)PhLac-OBn

H—L—(NH$_2$CO)PhLac-OH (4.34 g) was dissolved in DMSO (90 ml), and to the solution were added benzyl bromide (4.9 ml) and potassium carbonate (8.6 g). The reaction was conducted at 40° C. for 3 hours. Then, benzyl bromide (2.5 ml) and potassium carbonate (4.3 g) were further added to the reaction solution, and the reaction was further conducted at 40° C. for 1 hour.

After ethyl acetate (400 ml) was added to the reaction solution so obtained, the solution was washed with water (400 ml) and dried over anhydrous magnesium sulfate. The solvent was removed from the solution by evaporation under a reduced pressure, and the residue was purified by a silica gel column chromatography (eluted with chloroform-methanol=20:1, v/v), thus affording the titled compound (6.26 g; 99% yield based on H—L—(NC)PhLac-OMe) as white crystals.

$[\alpha]_D$=−19.1° (c=0.21,MeOH);

NMR(CD$_3$OD): δ=3.04(2H,ddd,J=0.5,0.7,1.4,2, β-CH$_2$), 4.44(1H,dd,J=0.6,0.8, α-CH), 5.11(2H,s,COOCH$_2$Ph), 7.25–7.33(7H,m,aromatic), 7.74(2H,d,J=0.8,aromatic).

(8) Synthesis of Boc-MeLeu-(NH$_2$CO)PhLac-OBn

H—(NH$_2$CO)PhLac-OBn (490 mg) was dissolved in THF (12.3 ml), and to the solution were added Boc-MeLeu-OH (442 mg) and triphenylphosphine (515 mg). Then, DEAD (0.31 ml) was added dropwise to the resulting mixture, and the reaction was conducted at room temperature for 1 hour. The solvent was removed from the resulting reaction solution by evaporation under a reduced pressure, and the residue was dissolved in ethyl acetate (50 ml). The resultant solution was washed, successively, with water, a 5% aqueous potassium hydrogen sulfate solution, a 7% aqueous sodium hydrogen carbonate solution and a 20% aqueous sodium chloride solution (50 ml each), and subsequently dried over anhydrous magnesium sulfate. The solvent was removed by evaporation under a reduced pressure, and the residue was purified by a silica gel column chromatography (eluted with chloroform-ethyl acetate=5:1, v/v), thus to afford the titled compound (594 mg; 68.8%) as white crystals.

NMR(CD$_3$OD): δ=0.89(6H,m, δ=CH$_3$(MeLeu)), 1.41, 1.48(9H,2s,Boc), 1.48–1.57(2H,m, β-CH$_2$(MeLeu)), 2.59 (3H,s,NMe(MeLeu)), 3.19–3.26(2H,m, β-CH$_2$(PhLac)), 4.08–4.18(1H,m, α-CH(MeLeu)), 5.11(2H,m,COOCH$_2$Ph), 5.34(1H,m, α-CH(PhLac)), 7.25–7.36(7H,m,aromatic), 7.79 (2H,d,J=0.7,aromatic).

(9) Synthesis of H-MeLeu-(NH$_2$CO)PhLac-OBn

Boc-MeLeu-(NH$_2$CO)PhLac-OBn (535 mg) was dissolved in an ice-cooled trifluoroacetic acid (5.35 ml), and the resulting solution was stirred under ice-cooling for 3 hours. The solvent was removed from the reaction solution by evaporation under a reduced pressure. Then, the residual amount of trifluoroacetic acid was removed from the residue by azeotropic distillation with toluene. The residue so obtained was dissolved in ethyl acetate (50 ml). The solution obtained was washed, successively, with a 7% aqueous sodium hydrogen carbonate solution and a 20% aqueous sodium chloride solution (50 ml, each) and dried over anhydrous magnesium sulfate. The solvent was removed from the dried solution by evaporation under a reduced pressure, thus to afford the titled compound in the form of its crude product (387 mg; 89.8%) as an oil. This was used in the next reaction step without purification.

NMR(CD$_3$OD): δ=0.74(6H,s×2,6H, δ-CH$_3$(MeLeu)), 1.33(2H,m, β-CH$_2$(MeLeu)), 2.14(3H,s,NMe), 3.12–3.20 (2H,m, β-CH$_2$(PhLac)), 3.30–3.67(1H,m,1H, α-CH (MeLeu)), 5.16(2H,s,COOCH$_2$Ph), 5.37(1H,dd,J=0.4,1.0, α-CH(PhLac)), 7.29–7.35(7H,m,aromatic), 7.82(2H,d,J= 0.8,aromatic)

(10) Synthesis of Boc-MeLeu-Lac-MeLeu-(NH$_2$CO)PhLac-OBn

Boc-MeLeu-Lac-OH (2.64 g) was dissolved in methylene chloride (53 ml), and to the solution was added H-MeLeu-(NH$_2$CO)PhLac-OBn (3.42 g). To the resultant mixture then were added, under ice-cooling, diisopropylethylamine (3.6 ml) and N,N-bis(2-oxo-3-oxazolydinyl)phosphinic acid chloride (BOP-Cl) (2.65 g). The mixture so obtained was subjected to reaction under ice-cooling for 24 hours. The solvent was removed from the reaction solution by evaporation and the residue was dissolved in ethyl acetate (200 ml). The resulting solution was washed, successively, with a 5% aqueous potassium hydrogen sulfate solution (200 ml) and a 20% aqueous sodium chloride solution (200 ml), and the solvent was evaporated off from the washed solution under a reduced pressure. The residue so obtained was purified by a silica gel column chromatography (eluted with chloroform-methanol=30:1, v/v), thus affording the titled compound (55.18 g; 89 1%) as white powder.

$[α]_D=-28.7°$ (c=0.21,MeOH); NMR(CDCl$_3$): δ=0.83–0.93(12H,m, δ-CH$_3$(MeLeu)), 0.83–1.47(12H,m, Boc, β-CH$_3$(Lac)), 1.60–1.77(4H,m, β-CH$_2$(MeLeu)), 2.82, 2.85(each 3H, each s,NMe), 3.20(d,2H,J=0.6, β-CH$_2$ (PhLac)), 4.30–5.37(m,6H, α-CH(MeLeu,Lac,PhLac), COOCH$_2$Ph), 7.18–7.38(7H,m,aromatic), 7.72(2H,d,J=0.8, aromatic).

(11) Synthesis of H-MeLeu-Lac-MeLeu-(NH$_2$CO)PhLac-OBn

Boc-MeLeu-Lac-MeLeu-(NH$_2$CO)PhLac-OBn (3.1 g) was dissolved inmethylene chloride (15.5 ml), and to the solution was added an ice-cooled trifluoroacetic acid (9.3 ml). The reaction was effected at room temperature for 30 minutes. The solvent and trifluoroacetic acid (THF) were evaporated off from the reaction solution under a reduced pressure, and further the residual TFA remaining in the solution was removed by azeotropic distillation with toluene. The residue so obtained was dissolved in ethyl acetate (200 ml), and the solution was washed, successively, with a 7% aqueous sodium hydrogen carbonate solution and a 20% aqueous sodium chloride solution (200 ml, each) and was dried over anhydrous magnesium sulfate. The solvent was removed from the dried solution by evaporation under a reduced pressure, thus to afford the titled compound in the form of a crude product (2.62 g; 97.9%) as an oil. This was used in the next reaction step without purification.

(12) Synthesis of Boc-MeLeu-Lac-MeLeu-PhLac-MeLeu-Lac-MeLeu-(NH$_2$CO)PhLac-OBn

Boc-MeLeu-Lac-MeLeu-PhLac-OH (1.07 g) and H-MeLeu-Lac-MeLeu-(NH$_2$CO)PhLac-OBn (1.06 g) were dissolved in methylene chloride (20 ml), and to the solution were added, under ice-cooling, diisopropylethylamine (0.6 ml) and BOP-Cl (0.52 g). With the resultant mixture, the reaction was conducted under ice-cooling for 2 hours. The solvent was removed from the resulting reaction solution by evaporation under a reduced pressure, and the residue was dissolved in ethyl acetate (100 ml). The solution obtained was washed with a 20% aqueous sodium chloride solution (100 ml) and dried over anhydrous magnesium sulfate. The solvent was removed from the dried solution by evaporation under a reduced pressure, and the resulting residue was purified by a silica gel column chromatography (eluted with chloroform-methanol=40:1, v/v), thus affording the titled compound (1.68 g; 82.2%) as white powder.

$[α]_D=-39.5°$ (c=0.11,MeOH); NMR(CDCl$_3$): δ=0.78–0.97(24H,m, δ-CH$_3$(MeLeu)), 1.43(9H,s,9H,Boc), 1.14–1.73(8H,m, β-CH$_2$(MeLeu)), 2.68, 2.79, 2.83, 2.88 (each s, each 3H,NMe), 2.76–3.74(4H,m, βCH$_2$(PhLac)), 4.76–5.60(10H,m, α-CH(MeLeu,Lac,PhLac),COOCH$_2$Ph), 7.21–7.76(14H,m,aromatic).

(13) Synthesis of H-MeLeu-Lac-MeLeu-PhLac-MeLeu-Lac-MeLeu-(NH$_2$CO)PhLac-OBn

Boc-MeLeu-Lac-MeLeu-PhLac-MeLeu-Lac-MeLeu-(NH$_2$CO) PhLac-OBn (1.6 g) was dissolved in methylene chloride (8.0 ml), and to the solution was added, under ice cooling, trifluoroacetic acid (4.8 ml), followed by effecting the reaction at room temperature for 30 minutes. The solvent and TFA were evaporated off from the reaction solution under a reduced pressure. The residual TFA remaining in the reaction solution was further removed by azeotropic distillation with toluene. The resulting residue was dissolved in ethyl acetate (150 ml), and the solution was washed, successively, with a 7% aqueous sodium hydrogen carbonate solution and a 20% aqueous sodium chloride solution (150 ml, each) and was dried over anhydrous magnesium sulfate. The solvent was removed from the dried solution by evaporation under a reduced pressure, thus to afford the titled compound in the form of its crude product (1.59 g; 100%) as an oil. This was used in the next reaction step without purification.

NMR(CDCl$_3$): δ=0.80–0.98(24H,m, δ=CH$_3$(MeLeu)), 1.34–1.53(6H,s,CH$_3$(Lac)), 1.14–2.05(8H,m, β-CH$_2$ (MeLeu)), 2.41, 2.73, 2.87, 2.95(each 4H, each s,NMe), 2.61–3.34(4H,m, β-CH$_2$(PhLac)), 5.05–5.47(10H,m, α-CH (MeLeu,Lac,PhLac), COOCH$_2$Ph), 7.22–7.38(12H,m, aromatic), 7.73(2H,d,J=0.8,aromatic).

(14) Synthesis of H-MeLeu-Lac-MeLeu-PhLac-MeLeu-Lac-MeLeu-(NH$_2$CO)PhLac-OH

H-MeLeu-Lac-MeLeu-PhLac-MeLeu-Lac-MeLeu-(NH$_2$CO)PhLac-OBn (1.46 g) was dissolved in methanol (30 ml), and to the solution were added, 10% Pd-activated carbon (146 mg) and acetic acid (0.1 ml) under a nitrogen atmosphere. The resultant mixture was subjected to reduction with hydrogen under atmospheric pressure for hour. The catalyst was removed from the reaction solution by filtration, and the solution was then concentrated under a reduced pressure for removal of the solvent, thus affording the titled compound (1.25 g; 93.0%) as an oil. This was used in the next reaction step without purification.

NMR(CDCl$_3$): δ=0.86–1.02(27H,m, β-CH$_3$(Lac), δ-CH$_3$(MeLeu), 1.29–1.72(11H,m, βCH$_3$(Lac), βCH$_2$(MeLeu)), 2.40–2.52(3H,NMe), 2.77–3.21(13H,m,NMe, β-CH$_2$(PhLac)), 5.02–5.51(8H,m, α-CH(MeLeu,LacPhLac)), 7.21–7.78(9H,m,aromatic).

(15) Synthesis of Cyclo[MeLeu-Lac-MeLeu-phLac-MeLeu-Lac-MeLeu-(NH$_2$CO)-PhLac] (Compound Code No. PF1022-242 substance)

H-MeLeu-Lac-MeLeu-PhLac-MeLeu-Lac-MeLeu-(NH$_2$CO)PhLac-OH (1.24 g) was dissolved in THF (174 ml), and to the solution were added 1-hydroxy-benzotriazole (0.83 g) and N-methylmorpholine (0.54 ml) under stirring. To the resultant mixture was added a mixture of lithium chloride (0.52 g), sodium chloride (0.72 g), potassium chloride (0.92 g), cesium chloride (2.07 g), 1-(3-dimethylaminopropyl)-3-ethylcarbodiimide hydrochloride (2.35 g), THF (1120 ml) and DMF (320 ml). The so resulting mixture was stirred for reaction at room temperature for 18 hours.

The solvent was removed from the resulting reaction solution by evaporation under a reduced pressure, and the residue was dissolved in ethyl acetate (120 ml). The solution so obtained was washed, successively, with a 5% aqueous potassium hydrogen sulfate solution, a 7% aqueous sodium hydrogen carbonate solution and a 5% aqueous sodium chloride solution (120 ml each) and was dried over anhydrous magnesium sulfate. The solvent was removed from the dried solution by evaporation under a reduced pressure, and the residue was purified by a silica gel column chromatography (eluted with ethyl acetate), thus to afford the titled compound (0.77 g; 63.3%) as white powder.

$[\alpha]_D$=−78.4° (c=0.14,MeOH); NMR(CDCl$_3$): δ=0.69–1.04(27H,m, β-CH$_3$(Lac), δ-CH$_3$(MeLeu)), 1.23–1.41(3H,m,CH$_3$(Lac)), 1.44–1.84(8H,m, β-CH$_2$(MeLeu)), 2.62–3.08(12H,m,NMe), 3.10–3.24(4H,m, β-CH$_2$(PhLac)), 4.45–5.79(8H,m, α-CH(MeLeu,Lac,PhLac)), 7.25–7.34(7H,m,aromatic), 7.79(2H,d,J=0.8, aromatic).

EXAMPLE 46

Cyclo[MeLeu-Lac-MeLeu-(NH$_2$CO)PhLac]$_2$
(Compound Code No. PF1022-247 substance)

(1) Synthesis of Boc-MeLeu-Lac-MeLeu-(NH$_2$CO)PhLac-OH

Boc-MeLeu-Lac-MeLeu-(NH$_2$CO)PhLac-OBn (1.8 g) was dissolved in methanol (36 ml), and to the solution were added a 10% Pd-activated carbon (1.18 g) and acetic acid (0.1 ml) under a nitrogen atmosphere. The resultant mixture was subjected to reduction with hydrogen at atmospheric pressure for 2.5 hours. The catalyst was removed from the resulting reaction solution by filtration, and the reaction solution was concentrated under a reduced pressure, removing the solvent therefrom and thus affording the titled compound in the form of its crude product (1.53 g; 99.1%) as an oil. This was used in the next reaction step without purification.

(2) Synthesis of Boc-MeLeu-Lac-MeLeu-(NH$_2$CO)PhLac-MeLeu-Lac-MeLeu-(NH$_2$CO)PhLac-OBn Boc-MeLeu-Lac-MeLeu-(NH$_2$CO)PhLac-OH (1.56 g) and MeLeu-Lac-MeLeu-(NH$_2$CO)PhLac-OBn (1.53 g) were dissolved in methylene chloride (31 ml), and to the solution were added, under ice-cooling, diisopropylethylamine (0.85 ml) and BOP-Cl (0.96 g). With the resultant mixture, the reaction was conducted under ice-cooling for 6 hours.

The solvent was removed from the resulting reaction solution by evaporation under a reduced pressure, and the residue was dissolved in ethyl acetate (200 ml). The solution obtained was washed, successively, with a 5% aqueous potassium hydrogen sulfate solution, a 7% aqueous sodium hydrogen carbonate solution and a 20% aqueous sodium chloride solution (200 ml each) and was dried over anhydrous magnesium sulfate. Then, the solvent was removed from the dried solution by evaporation under a reduced pressure.

The residue so obtained was purified by a silica gel column chromatography (eluted with chloroform-methanol=30:1, v/v), thus affording the titled compound (1.92 g; 63.1%) as white powder.

$[\alpha]_D$=−37.9° (c=0.10,MeOH); NMR(CDCl$_3$): δ=0.70–0.85(24H,m, β-CH$_3$(Lac), δ-CH$_3$(MeLeu)), 1.18–1.86(11H,m, β-CH$_3$(Lac), β-CH$_2$(MeLeu)), 2.68–3.15 (16H,m,NMe, β-CH$_2$(PhLac)), 5.03–5.32(10H,m, α-CH(MeLeu,Lac,PhLac), COOCH$_2$), 7.13–7.70(13H,m, aromatic).

(3) Synthesis of H-MeLeu-Lac-MeLeu-(NH$_2$CO)PhLac-MeLeu-Lac-MeLeu-(NH$_2$CO)-PhLac-OBn Boc-MeLeu-Lac-MeLeu-(NH$_2$CO)PhLac-MeLeu-Lac-MeLeu-(NH$_2$CO)PhLac-OBn (1.8 g) was dissolved in methylene chloride (9 ml), and to the solution was added an ice-cooled TFA (5.4 ml). The resultant mixture was subjected to the reaction at room temperature for 1 hour. The resulting reaction solution was heated so that solvent and trifluoroacetic acid were evaporated off under a reduced pressure. The residual trifluoroacetic acid remaining in the residue obtained was removed by azeotropic distillation with toluene. The residue so afforded was dissolved in ethyl acetate (200 ml), and the resulting solution was washed, successively, with a 7% aqueous sodium hydrogen carbonate solution and a 20% aqueous sodium chloride solution (200 ml each) and was dried over anhydrous magnesium sulfate. Then the solvent was removed from the dried solution by evaporation under a reduced pressure, thus to afford the titled compound in the form of its crude product (1.64 g; 99%) as an oil. This was used in the next reaction step without purification.

(4) Synthesis of H-MeLeu-Lac-MeLeu-(NH$_2$CO)PhLac-MeLeu-Lac-MeLeu-(NH$_2$CO)PhLac-OH H-MeLeu-Lac-MeLeu-(NH$_2$CO)PhLac-MeLeu-Lac-MeLeu-(NH$_2$CO)PhLac-OBn (1.63 g) was dissolved in methanol (33 ml), and to the solution were added, under a nitrogen atmosphere, 10% Pd-activated carbon (163 mg) and acetic acid (0.2 ml). The resultant mixture was subjected to reduction with hydrogen at atmospheric pressure for 2.5 hours. The catalyst was removed from the resulting reaction solution by filtration, and the solvent was removed from the solution by evaporation under a reduced pressure, thus to afford the titled compound in the form of its crude product (1.44 g; 95.9%) as an oil. This was used in the next reaction step without purification.

(5) Synthesis of Cyclo[MeLeu-Lac-MeLeu-(NH$_2$CO)PhLac]$_2$ (Compound Code No. PF1022-247 substance)

H-MeLeu-Lac-MeLeu-(NH$_2$CO)PhLac-MeLeu-Lac-MeLeu-(NH$_2$CO)PhLac-OH (44 g) was dissolved in THF (202 ml), and to the solution were added a mixture of 1-hydroxybenzotriazole (0.92 g) and N-methylmorpholine (0.6 ml). The resultant mixture was stirred. To said mixture was then added a mixture of lithium chloride (0.58 g), sodium chloride (0.80 g), potassium chloride (1.02g), cesium chloride (2.30 g), 1-(3-dimethylaminopropyl)-3-ethyl-carbodiimide hydrochloride (2.62 g), THF (1.31 ml) and DMF (37 5 ml). The resulting mixture was stirred for reaction at room temperature for 16 hours.

The resulting reaction solution was concentrated under a reduced pressure to remove the solvent from the reaction solution. The residue was dissolved in ethyl acetate (150 ml), and the solution so obtained was washed, successively, with a 5% aqueous potassium hydrogen sulfate solution, a 7% aqueous sodium hydrogen carbonate solution and a 20% aqueous sodium chloride solution (150 ml each) and was dried over anhydrous magnesium sulfate. Then the solvent was removed from the dried solution by evaporation under a reduced pressure. The residue so obtained was purified by a silica gel column chromatography (eluted with chloroform-methanol=10:1, v/v), thus affording the titled compound (0.93 g; 65.4%) as white powder.

$[\alpha]_D=-75.4°$ (c=0.11,MeOH); NMR(CDCl$_3$): δ=0.56–1.04(27H,m, β-CH$_3$(Lac), δ-CH$_3$(MeLeu)), 1.41 (3H,m, β-CH$_3$(Lac)), 1.25–1.80(8H,m, β-CH$_2$(MeLeu)), 2.79, 2.82, 2.86, 3.07(12H, each s,NMe), 3.12–3.27(4H,m, β-CH$_2$(PhLac)), 4.45–5.71(8H,m, α-CH(MeLeu,Lac,PhLac)), 5.91,6.31(each 1H, each bs,CONH$_2$)), 7.30–7.81 (8H,m,aromatic).

EXAMPLE 47.

Cyclo[MeLeu-Lac-MeLeu-(HOCO)Lac]$_2$ (Compound Code No. PF1022-030 substance) and Cyclo[MeLeu-Lac-MeLeu-(HOCO)Lac-MeLeu-Lac-MeLeu-PhLac] (Compound Code No. PF1022-031 substance)

(1) PF1022 substance (4.0 g) and orthoperiodic acid (9.15 g) were placed in a mixture of carbon tetrachloride (8 ml), acetonitrile (8 ml) and water (12 ml), which was then stirred and to which ruthenium trichloride n-hydrate (11.4 mg) was added further under stirring of the mixture. After the resulting mixture was further stirred at room temperature for 2 hours, orthoperiodic acid (9.10 g) was added, and after stirring for further 2.5 hours, orthoperiodic acid (9.12 g) was added thereto. The resulting mixture was further stirred at room temperature overnight. To the resulting reaction solution was added diethylether (5 ml) under ice-cooling and the mixture so obtained was stirred for 50 minutes. Then chloroform (30 ml) and water (30 ml) were added to said mixture to separate the aqueous and organic layers. The organic layer was isolated. The aqueous layer was further extracted with chloroform (30 ml). The chloroform extract was combined with the organic layer isolated as above, followed by drying over anhydrous sodium sulfate. The dried solution was concentrated under a reduced pressure. The residue obtained was purified by a silica gel column chromatography (eluted with chloroform-methanol=20:1~8:1), thus to afford a mixture of both the titled compounds (2.85 g)

(2) PF1022-045 substance (0.95 g), which is a compound given in the following Example 48 below, was dissolved in methylene chloride (3 ml), and to the solution were added a small amount of water and trifluoroacetic acid (3 ml). The resultant mixture was stirred at room temperature for 3.5 hours. The reaction solution so obtained was concentrated under a reduced pressure, and the resultant residue was purified by a silica gel column chromatography (eluted with chloroform-ethyl acetate=10:1 and then with chloroform-methanol=10:1), thus to afford the titled compound (PF 1022-030 substance)(617 mg) as white powder.

On the other hand, PF1022-046 substance (5.11 g), which is a compound given in the following Example 48, was dissolved in methanol (100 ml), and to the solution was added a 10% Pd/carbon (248 mg). The resultant mixture was stirred under a hydrogen atmosphere for 24 hours. The catalyst was removed from the resulting reaction solution by filtration, and the filtrate obtained was concentrated under a reduced pressure. The resultant residue was purified by a silica gel column chromatography (eluted with chloroform-methanol=50:1~10:1), thus affording the titled compound (PF1022-031 substance)(4.08 g) as white powder.

PF1022-030 substance: MS(FAB): 885(M); PF1022-031 substance: $[\alpha]_D=-70.0°$ (c=0.11,MeOH); $^1$H-NMR(CDCl$_3$): δ=0.78–1.10(27H,m), 1.12–1.92(15H,m), 2.3–3.3(18H,m), 4.44–4.76(1H,m), 5.02–5.96(7H,m), 7.2–7.36(5H,m); MS(FAB+) 917(M$^+$).

EXAMPLE 48

Cyclo[MeLeu-Lac-MeLeu-((C$_6$H$_5$)$_2$CHOCO)Lac]$_2$ (Compound Code No. PF1022-045 substance) and Cyclo[MeLeu-Lac-MeLeu-((C$_6$H$_5$)$_2$CHOCO)Lac-MeLeu-Lac-MeLeu-PhLac] (Compound Code No. PF1022-046 substance)

The mixture (2.85 g) of the titled compounds described in Example 47 (1) was dissolved in ethyl acetate (30 ml), and to the solution was added, dropwise, a solution of diphenyldiazomethane (1.52 g) in ethyl acetate (15 ml) over 45 minutes. The resultant mixture was stirred at room temperature overnight and then added with acetic acid (1.0 ml), after which the mixture was stirred for further 6 hours. The reaction solution so obtained was washed, successively, with an aqueous saturated sodium hydrogen carbonate solution (50 ml), a 10% aqueous potassium hydrogen sulfate solution (50 ml) and an aqueous saturated sodium chloride solution (50 ml) and was dried over anhydrous sodium sulfate. The dried solution was concentrated under a reduced pressure, and the resultant residue was purified by a silica gel column chromatography (eluted with ethyl acetate-n-hexane= 1:3~1:2), thus affording both the titled compounds (1.64 g and 0.23 g, respectively), each as white powder.

PF1022-045 substance: $[\alpha]_D=-56.4°$ (c=0.11,MeOH); $^1$H-NMR(CD$_3$OD, KSCN was added): δ=0.74–1.0(24H,m), 1.22–2.0(18H,m), 2.86(6H,s), 3.09(6H,s), 2.86–3.20(4H,m), 5.25–5.77(8H,m), 6.94(2H,s), 7.23–7.45(20H,m); MS(FD) :1217(M+1); PF1022-046 substance: $[\alpha]_D=-74.1°$ (c=0.11, MeOH); $^1$H-NMR(CDCl$_3$): δ=0.7–1.1(27H,m), 1.2–2.0 (15H,m), 2.68–3.26(16H,m), 4.36–4.52(1H,m), 4.96–5.94 (7H,m), 6.81–6.90(1H,m), 7.16–7.40(15H,m); MS(FD) :1082(M).

EXAMPLE 49

Cyclo[MeLeu-Lac-MeLeu-(CH$_3$CO)PhLac-MeLeu-Lac-MeLeu-PhLac] and Cyclo[MeLeu-Lac-MeLeu-(CH$_3$CO)PhLac-MeLeu-Lac-MeLeu-(CH$_3$CO) PhLac] (Compound Code No. PF1022-049 substance and Compound Code No. PF1022-048 substance, respectively)

Aluminium chloride (5.02 g) was added to an ice-cooled acetyl chloride (3.5 ml) under a nitrogen atmosphere, and to the resulting solution was then added, dropwise, under vigorous stirring, a solution of PF1022 substance (2.0 g,) in acetyl chloride (5 ml), The resultant mixture was heated under reflux for 30 minutes. The reaction solution so obtained was cooled to room temperature, and then solid material precipitated in the solution were dissolved in ethyl acetate (10 ml) added. The resultant whole mixture was further diluted with ethyl acetate (100 ml), washed, successively, with a cold water (80 ml) containing a concentrated hydrochloric acid (2 ml), water (80 ml), an aqueous saturated sodium hydrogen carbonate solution (50 ml, twice) and an aqueous saturated sodium chloride solution (50 ml) and was dried over anhydrous sodium sulfate. The dried solution was concentrated under a reduced pressure.

The resulting residue was purified by a silica gel column chromatography (eluted with ethyl acetate-hexane=1:1) and then by a preparative reverse phase HPLC using ODS (eluted with 75%~70% aqueous acetonitrile containing 0.05% TFA). Thus, both the titled compounds (PF1022-049 substance: 200 mg; and PF1022-048 substance: 190 mg) were obtained each as white powder. Further, 808 mg of PF1022 substance was recovered.

PF1022-048 substance: $^1$H-NMR(CDCl$_3$): δ=0.7–1.08 (27H,m), 1.18–1.82(15H,m), 2.56–3.28(19H,m), 4.46(1H, m), 5.0–5.76(7H,m), 7.16–7.46(7H,m), 7.8–7.92(2H,m). PF1022-049 substance: $^1$H-NMR(CDCl$_3$): δ=0.7–1.1(27H, m), 1.16–2.02(15H,m), 2.56–3.28(22H,m), 4.47(1H,m), 5.0–5.72(7H,m), 7.2–7.5(4H,m), 7.3–7.95(4H,m).

EXAMPLE 50

Cyclo[MeLeu-Lac-MeLeu-(BrCH$_2$CO)PhLac-MeLeu-Lac-MeLeu-PhLac]

Cyclo[MeLeu-Lac-MeLeu-(CH$_3$CO)PhLac-MeLeu-Lac-MeLeu-PhLac] (101 mg), which was obtained in Example 49 above, was dissolved in chloroform (10 ml), and to the solution were added, dropwise, a 1.56M solution of bromine in chloroform (0.07 ml) and a 48% hydrobromic acid (1 drop). The resultant mixture was stirred at 25≅ C. for 3.5 hours. The reaction solution so obtained was concentrated, and the residue was purified by a silica gel column chromatography (eluted with ethyl acetate-hexane=1:1), thus to afford the titled compound (88.1 mg).

$^1$H-NMR(CDCl$_3$): δ=0.7–1.1(27H,m), 1.2–1.8(15H,m), 2.68–3.30(16H,m), 4.40(2H,s), 4.46(1H,m), 5.0–5.74(7H, m), 7.14–7.44(7H,m), 7.84–7.97(2H,m).

EXAMPLE 51

Cyclo[MeLeu-Lac-MeLeu-(HCOOCH$_2$CO)PhLac-MeLeu-Lac-MeLeu-PhLac]

Cyclo[MeLeu-Lac-MeLeu-(BrCH$_2$CO)PhLac-MeLeu-Lac-MeLeu-PhLac] (88.1 mg) was dissolved in acetone (8 ml), and to the solution was added a buffered solution of 0.7 M formic acid-sodium formate (pH 4.2) (2 ml.) The resultant mixture was stirred at 60° C. for 90 minutes. The reaction solution so obtained was allowed to cool to room temperature and then diluted with ethyl acetate (50 ml), followed by washing, successively, with a 10% potassium hydrogen sulfate solution (30 ml), an aqueous saturated sodium hydrogen carbonate solution (30 ml) and an aqueous saturated sodium chloride solution (30 ml) and drying over anhydrous sodium sulfate. The dried solution was concentrated under a reduced pressure, to obtain in the titled compound (82.5 mg). This was used in the next reaction step without any purification.

$^1$H-NMR(CDCl$_3$): δ=0.7–1.06(27H,m), 1.2–1.8(15H,m), 2.68–3.30(16H,m), 4.46(1H,m), 5.40(2H,s), 5.0–5.72(7H, m), 7.16–7.44(7H,m), 7.75–7.90(2H,m), 8.28(1H,s).

EXAMPLE 52

Cyclo[MeLeu-Lac-MeLeu-(HOCH$_2$CO)PhLac-MeLeu-Lac-MeLeu-PhLac]

Cyclo[MeLeu-Lac-MeLeu-(HCOOCH$_2$CO)PhLac-MeLeu-Lac-MeLeu-PhLac] (82.5 mg) was dissolved in methanol (9.5 ml), and to the solution was added 2N HCl (0.5 ml). The resultant mixture was stirred at room temperature overnight. The resulting reaction solution was concentrated under a reduced pressure, giving the titled compounds (83.1 mg). This was used in the next reaction step without any purification.

$^1$H-NMR(CDCl$_3$): δ=0.7–1.06(27H,m), 1.15–1.8(15H, m), 2.65–3.30(16H,m), 4.46(1H,m), 4.84(2H,s), 5.0–5.74 (7H,m), 7.1–7.45(7H,m), 7.75–7.90(2H,m).

EXAMPLE 53

Cyclo[MeLeu-Lac-MeLeu-(HOCO)PhLac-MeLeu-Lac-MeLeu-PhLac] (Compound Code No. PF1022-241 substance)

Cyclo[MeLeu-Lac-MeLeu-(HOCH$_2$CO)PhLac-MeLeu-Lac-MeLeu-PhLac] was dissolved in THF (5 ml), and to the solution were added sodium per-iodate (174 mg) and water (1 drop). The resultant mixture was stirred at room temperature for 7 hours. The reaction solution obtained was diluted with ethyl acetate (50 ml), then washed with an aqueous 10% sodium chloride solution(30 ml) containing 2N hydrochloric acid(2 ml) and was dried over anhydrous sodium sulfate. The dried solution was concentrated under a reduced pressure. The residue was purified by a silica gel column chromatography (eluted with chloroform-methanol= 50:1~50:2), thus affording the titled compound (71.1 mg) as white powder.

$^1$H-NMR(CDCl$_3$): δ=0.7–1.1(27H,m), 1.17–1.82(15H, m), 2.68–3.32(16H,m), 4.48(1H,m), 5.0–5.73(7H,m), 7.12–7.40(7H,m), 7.95–8.07(2H,m); MS(SIMS):993(M+1).

EXAMPLE 54

Cyclo[MeLeu-Lac-MeLeu-(MorCO)PhLac-MeLeu-Lac-MeLeu-PhLac] (Compound Code No. PF1022-244 substance)

Cyclo[MeLeu-Lac-MeLeu-(HOCO)PhLac-MeLeu-Lac-MeLeu-PhLac] (121 mg) was dissolved in methylene chloride (4 ml) under a nitrogen atmosphere, and to the resulting solution were added triethylamine (40 μl) and ethyl chlorocarbonate (13 μl) at −15° C. The resultant mixture was stirred for 10 minutes, and then added with morpholine (12 μl). The temperature of the mixture so obtained was slowly elevated up to room temperature, and the mixture was stirred for further 30 minutes. After a 10% aqueous solution of potassium hydrogen sulfate (10 ml) was added to the reaction solution obtained, the latter was extracted with chloroform (15 ml). The remaining aqueous layer was again extracted with chloroform (10 ml). The organic layers (the extracts in chloroform) were combined and dried over anhydrous sodium sulfate. The organic solution was concentrated under a reduced pressure, and the residue was purified by a silica gel column chromatography (eluted with chloroform-methanol=80:1~20:1), thus to afford the titled compound (75.8 mg) as white powder.

[α]$_D$=−83.2° (c=0.03,MeOH); $^1$H-NMR(CDCl$_3$): δ=0.73–1.06(27H,m), 1.10–1.85(15H,m), 2.65–3.24(16H, m), 3.27–4.0(8H,bs), 4.47(1H,m), 5.0–5.72(7H,m), 7.16–7.40(9H,m); MS (SIMS): 1062(M+1).

EXAMPLE 55

Cyclo[MeLeu-Lac-MeLeu-((CH$_3$)$_2$NCO)PhLac-MeLeu-Lac-MeLeu-PhLac] (Compound Code No. PF1022-243 substance)

Cyclo[MeLeu-Lac-MeLeu-(HOCO)PhLac-MeLeu-Lac-MeLeu-PhLac] (namely, PF1022-241 substance) (150 mg), which was obtained in Example 53, was dissolved in THF (3 ml), and to the solution were added, under ice-cooling, DCC (46.7 mg), HOBt (26.5 mg), triethylamine (0.046 ml) and dimethylamine hydrochloride (14.8 mg). The resultant mixture was stirred for reaction for 2 hours. Then, DCC, HOBt, triethylamine and dimethylamine hydrochloride of the same amounts as those used above, respectively, were again added to the resulting reaction solution. The mixture so obtained was allowed to react further for 3.5 hours, followed by further adding thereto DCC, HOBt, triethylamine and dimethylamine hydrochloride of the same amounts as those used above, respectively. Subsequently, the reaction was continued for further 15 hours.

The reaction solution so obtained was filtered to remove insoluble materials. The resulting filtrate was concentrated under a reduced pressure to remove the solvent. The residue obtained was dissolved in ethyl acetate (20 ml), and the solution was washed, successively, with a 5% aqueous potassium hydrogen sulfate solution, a 7% aqueous sodium hydrogen carbonate solution and a 20% aqueous sodium chloride solution (20 ml each) and was dried over anhydrous magnesium sulfate. The solvent was removed from the dried solution by evaporation under a reduced pressure, and the residue was purified by a silica gel column chromatography (eluted with ethyl acetate), thus to afford the titled compound (117 mg, 76.6%) as white powder.

$[\alpha]_D = -87.4°$ (c=0.10,MeOH); NMR(CDCl$_3$): $\delta$=0.80–1.05(27H,m, $\delta$-CH$_3$(MeLeu), $\beta$-CH$_3$(Lac)), 1.25–1.42(3H,m, $\delta$-CH$_3$(Lac)), 1.48–1.68(12H,m, $\beta$-CH$_2$, $\gamma$-CH(MeLeu)), 2.73–3.19(22H,m,NMe(MeLeu), Me$_2$NCO, $\beta$-CH$_2$(PhLac,(CH$_3$)$_2$NCO)PhLac), 4.48–5.68(8H,m, $\alpha$-CH), 7.24–7.39(9H,m,aromatic); MS(SIMS): 1020(M+1).

EXAMPLE 56

Cyclo[MeLeu-Lac-MeLeu-((CH$_3$)$_2$NCH$_2$CH$_2$OCO) PhLac-MeLeu-Lac-MeLeu-PhLac] (Compound Code No. PF1022-245 substance)

Cyclo[MeLeu-Lac-MeLeu-(HOCO)PhLac-MeLeu-Lac-MeLeu-PhLac] (namely, PF1022-241 substance) (183 mg) was dissolved in THF (3.7 ml), and to the solution were added, under ice-cooling, DCC (57 mg), HOBt (33 mg), triethylamine (0.031 ml) and dimethylaminoethanol (0.022 ml). The resultant mixture was stirred for reaction for 4 hours. Then, DCC (19 mg), HOBt (12 mg), triethylamine (0.013 ml) and dimethylaminoethanol (0.01 ml) were further added to the reaction mixture, and the latter was stirred for the reaction further for 18 hours. Subsequently, to the reaction mixture, DCC, HOBt, triethylamine and dimethylamino ethanol were further added, each in their same amounts as those used above. The resulting mixture was further stirred for the reaction for 15 hours.

The reaction solution so obtained was filtered to remove insoluble materials, and the resultant filtrate was concentrated under a reduced pressure to remove the solvent. The residue was dissolved in ethyl acetate (20 ml), and the solution was washed, successively, with a 5% aqueous potassium hydrogen sulfate solution a 7% aqueous sodium hydrogen carbonate solution and a 20% aqueous sodium chloride solution (20 ml each) and was dried over anhydrous magnesium sulfate. The solvent was removed from the dried solution by evaporation under a reduced pressure. The residue was purified by a silica gel column chromatography (eluted with chloroform-methanol=15:1), thus affording the titled compound (131 mg; 66.9%) as white powder.

$[\alpha]_D = -89.3°$ (c=0.10,MeOH); NMR(CDCl$_3$): $\delta$=0.80–1.05(27H,m, $\delta$-CH$_3$(MeLeu), $\beta$-CH$_3$(Lac)), 1.25–1.41(3H,m, $\beta$-CH$_3$(Lac)), 1.42–1.75(12H,m, $\beta$-CH$_2$, $\gamma$-CH(MeLeu)), 2.34(6H,s,NMe2((CH$_3$)$_2$NCH$_2$CH$_2$OCO)) 2.69–2.83(12H,m,NMe(MeLeu)), 3.01–3.20(6H,m, $\beta$CH$_2$(PhLac,(CH$_3$)$_2$NCH$_2$CH$_2$OCO)PhLac), CH$_2$((CH$_3$)$_2$NCH$_2$CH$_2$OCO)), 4.41(2H,t,=05,CH$_2$((CH$_3$)$_2$NCH$_2$CH$_2$OCO), 4.47–5.68(8H,m, $\alpha$-CH(Lac)), 7.25–7.34 (7H,m,PhLac,(CH$_3$)$_2$NCH$_2$CH$_2$OCO)PhLac), 7.97(2H,m,(CH$_3$)$_2$NCH$_2$CH$_2$OCO)PhLac); MS (FAB): 1064(M+1).

EXAMPLE 57

Cyclo[MeLeu-Lac-MeLeu-(MorCH$_2$CH$_2$OCO) PhLac-MeLeu-Lac-MeLeu-PhLac] (Compound Code No. PF1022-246 substance)

Cyclo[MeLeu-Lac-MeLeu-(HOCO)PhLac-MeLeu-Lac-MeLeu-PhLac] (namely, PF1022-241 substance) (207.5 mg) was dissolved in THF (4 ml), and to the solution were added, under ice-cooling, DCC (62 mg), HOBt (35 mg), triethylamine (0.034 ml) and morpholinoethanol (0.029 ml). The resultant mixture was stirred for the reaction for 16 hours. Then, DCC (21 mg), HOBt (14 mg), triethylamine (0.008 ml) and morpholinoethanol (0.007 ml) were further added to the reaction mixture, and the mixture was stirred for further 18 hours.

The reaction solution so obtained was filtered to remove insoluble materials, and the resultant filtrate was concentrated under a reduced pressure to remove the solvent. The residue was dissolved in ethyl acetate (20 ml) and the solution obtained was washed, successively, with a 5% aqueous potassium hydrogen sulfate solution, a 7% aqueous sodium hydrogen carbonate solution and a 20% aqueous sodium chloride solution (20 ml each) and was dried over anhydrous magnesium sulfate. The solvent was removed from the dried solution by evaporation under a reduced pressure. The residue obtained was purified by a silica gel column chromatography (eluted with chloroform-methanol=30:1), thus to afford the titled compound (115 mg; 49.8%) as white powder.

$[\alpha]_D = -105°$ (c=0.11,MeOH); NMR(CDCl$_3$): $\delta$=0.80–1.06(27H,m, $\delta$-CH$_3$(MeLeu), $\beta$-CH$_3$(Lac)), 1.38–1.43(3H,m, $\beta$-CH$_3$(Lac)), 1.53–1.91(12H,m, $\beta$-CH$_2$, $\gamma$-CH(MeLeu)), 2.59(4H,t,J=0.4,Mor), 2.76–2.85(12H,m, NMe(MeLeu)), 3.03–3.38(6H,m, $\beta$-CH$_2$(PhLac,(CH$_3$)$_2$NCH$_2$CH$_2$OCO)PhLac), CH$_2$(MorCH$_2$CH$_2$OCO)), 3.73 (4H,m,J=0.4,Mor), 5.09–5.71(8H,m, $\overline{\alpha\text{-CH}}$(Lac)), 7.28(5H, m,aromatic(PhLac), 7.34,7.99(each 2H, each m,(MorCH$_2$CH$_2$OCO)PhLac), MS(FAB): 1106(M+1).

EXAMPLE 58

Cyclo(MeLeu-Lac-MeLeu-(BrCH$_2$CO)PhLac]$_2$

Cyclo[MeLeu-Lac-MeLeu-(CH$_3$CO)PhLac]$_2$ (1.10 g) was dissolved in chloroform (100 ml), and to the solution were added 1.56M bromine solution in chloroform (1.5 ml) and a 48% hydrobromic acid (1 drop). The resultant mixture was stirred at room temperature for 1 hour 40 minutes. The reaction solution so obtained was washed with a saturated aqueous sodium hydrogen carbonate solution (75 ml), and the aqueous washing obtained was extracted with chloroform (50 ml). The organic layers so obtained were combined, dried over anhydrous sodium sulfate and concentrated under a reduced pressure to give the titled compound (0.96 g).

EXAMPLE 59

Cyclo[MeLeu-Lac-MeLeu-(HCOOCH$_2$CO)PhLac]$_2$

Cyclo[MeLeu-Lac-MeLeu-(BrCH$_2$CO)PhLac]$_2$ (0.96 g) was dissolved in acetone (80 ml), and to the solution was added a buffered solution of 0.7N formic acid-sodium formate (pH 4.2) (20 ml). The resultant mixture was stirred at 60° C. for 75 minutes. The acetone was evaporated off from the resulting reaction solution under a reduced pressure. To the residue were added a 10% aqueous sodium chloride solution (50 ml) and a 2N hydrochloric acid (2 ml). The resulting mixture was extracted twice with chloroform (60 ml each). The organic layers (the extracts in chloroform) were combined and dried over anhydrous sodium sulfate. The dried organic solution was concentrated under a reduced pressure to give the titled compound (0.90 g)

EXAMPLE 60

Cyclo[MeLeu-Lac-MeLeu-(HOCH$_2$CO)PhLac]$_2$

Cyclo[MeLeu-Lac-MeLeu-(HCOOCH$_2$CO)PhLac]$_2$ (0.90 g) was dissolved in methanol (95 ml), and to the solution was then added a 2N aqueous HCl (5 ml). The resultant mixture was stirred at 30° C. for 2 hours. The resulting reaction solution was concentrated under a reduced pressure to give the titled compound (0.90 g).

EXAMPLE 61

Cyclo[MeLeu-Lac-MeLeu-(HOCO)PhLac]$_2$

Cyclo[MeLeu-Lac-MeLeu-(HOCH$_2$CO)PhLac]$_2$ (0.90 g) was dissolved in THF (90 ml), and to the solution were added sodium periodate (4.15 g) and water (10 ml). The resultant mixture was stirred at room temperature overnight. The THF was evaporated off from the resulting reaction solution, and a 10% aqueous sodium chloride solution (100 ml) containing a 2N HCl (5 ml) was added to the residue obtained. The mixture so obtained was extracted twice with chloroform (100 ml, 50 ml). The organic layers (the extracts in chloroform) were combined and dried over anhydrous sodium sulfate. The solvent was removed from the dried solution by evaporation under a reduced pressure. The residue was purified by a silica gel column chromatography (eluted with chloroform-methanol=50:1~50:3), thus affording the titled compound (855 mg) as white powder.

$^1$H-NMR(CD$_3$OD, KSCN was added): δ=0.86(6H,d,J=6.7 Hz), 0.89(12H,d,J=6.7 Hz), 0.94(6H,d,J=6.7 Hz), 1.18–1.42(4H,m), 1.46(6H,d,J=6.7 Hz), 1.57(4H,dd,J=7.0, 8.2), 1.81(4H,dd,J=6.7,7.9), 2.92(6H,s), 3.06(6H,s), 3.16(2H,dd,J=9.0,14.1), 3.27(2H,dd,J=5.3,14.1), 5.32–5.45(6H,m), 5.62(2H,dd,J=5.3,9.0), 7.48(4H,d,J=8.2 Hz), 8.00(4H,d,J=8.2 Hz); MS(SIMS): 1060(M+Na), 1037(M+1).

EXAMPLE 62

Cyclo[MeLeu-Lac-MeLeu-((CH$_3$)$_2$NCO)PhLac]$_2$ (Compound Code No. PF1022-248 substance)

Cyclo[MeLeu-Lac-MeLeu-(HOCO)PhLac]$_2$ (50.2 mg), HOBt (42.0 mg), dimethylamine hydrochloride (36.2 mg) and triethylamine (0.1 ml) were dissolved in THF (3 ml), and to the solution DCC (53.7 mg) was added. The resultant mixture was stirred at room temperature overnight. The reaction solution so obtained was filtered to remove insoluble material. The resulting filtrate was diluted with ethyl acetate (20 ml), and then was washed, successively, with a 10% potassium hydrogen sulfate solution (10 ml) and an aqueous saturated sodium chloride solution (10 ml) and was dried over anhydrous sodium sulfate. The dried solution was concentrated under a reduced pressure, and the residue was purified by a silica gel column chromatography (eluted with chloroform-methanol=50:1), thus affording the titled compound (52.8 mg) as white powder.

$[α]_D$=−85.7° (c=0.10,MeOH); $^1$H-NMR(CDCl$_3$): δ=0.76–1.08(27H,m), 1.10–1.84(15H,m), 2.72–3.26(28H,m), 4.50(1H,m), 5.03–5.70(7H,m), 7.26–7.44(8H,m); MS(FD):1091(M+1).

EXAMPLE 63

Cyclo[MeLeu-Lac-MeLeu-(MorCO)PhLac]$_2$ (Compound Code No. PF1022-249 substance)

Cyclo[MeLeu-Lac-MeLeu-(HOCO)PhLac]$_2$ (203 mg) was dissolved in methylene chloride (10 ml) under a nitrogen atmosphere, and to the solution were added triethylamine (0.14 ml) and ethyl chlorocarbonate (0.05 ml) at −10° C. The resultant mixture was stirred at −10° C. for 5 minutes. After morpholine (0.05 ml) was added to the reaction mixture at the same temperature, the mixture was slowly warmed up to room temperature and stirred for further 2 hours.

To the reaction solution so obtained was added a 10% aqueous potassium hydrogen sulfate (20 ml), and the resultant mixture was extracted with chloroform (20 ml). The remaining aqueous layer was again extracted with chloroform (20 ml). The organic layers (the extracts in chloroform) were combined and dried over anhydrous sodium sulfate. The dried organic solution was concentrated under a reduced pressure. The residue was purified by a silica gel column chromatography (eluted with chloroform-ethyl acetate=4:1~1:1, subsequently with chloroform-methanol=50:1~20:1), thus to afford the titled compound (120 mg) as white powder.

$[α]_D$=−73.0° (c=0.04,MeOH); $^1$H-NMR(CDCl$_3$): δ=0.74–1.04(27H,m), 1.10–1.80(15H,m), 2.70–3.23(16H,m), 3.24–4.0(16H,bs), 4.47(1H,dd,J=5.1,9.5 Hz), 5.06(1H,q,J=6.7 Hz), 5.2–5.68(6H,m), 7.18–7.37(8H,m); MS(FD):1075(M+1).

EXAMPLE 64

Cyclo[MeLeu-Lac-MeLeu(MorCH$_2$CH$_2$OCO)PhLac]$_2$ (Compound Code No. PF1022-251 substance)

Cyclo[MeLeu-Lac-MeLeu-(HOCO)PhLac]$_2$ (193 mg), HOBt (541 mg) and morpholino-ethanol (0.06 ml) were dissolved in THF (5 ml), and to the resulting solution DCC (118 mg) was added. The mixture obtained was stirred at room temperature overnight. The reaction solution so obtained was filtered to remove insoluble material, and the resultant filtrate was diluted with ethyl acetate (20 ml), and the diluted solution was then washed successively with a 10% potassium hydrogen sulfate solution (10 ml) and an aqueous saturated sodium chloride solution (10 ml) and was dried over anhydrous sodium sulfate and. The dried solution was concentrated under a reduced pressure, and the residue was purified by a silica gel column chromatography (eluted with chloroform-methanol=25:1), thus to afford the titled compound (210 mg) as white powder.

$[α]_D$=−75.6° (c=0.09,MeOH); $^1$H-NMR(CDCl$_3$): δ=0.70–1.08(27H,m), 1.16–1.82(15H,m), 2.56(8H,t,J=4.5 Hz), 2.65–3.28(20H,m), 3.70(8H,t,J=4.5 Hz), 4.44(5H,m), 5.06(1H,q,J=6.7 Hz), 5.15–5.74(6H,m), 7.32(4H,d,J=8.2 Hz), 7.96(4H,d,J=8.2 Hz); MS(FD):1263(M+1).

EXAMPLE 65

Cyclo[MeLeu-(p-Mor)PhLac-MeLeu-Lac-MeLeu-PhLac-MeLeu-Lac] (Compound Code No. PF1022-233 substance)

Cyclo[MeLeu-(H$_2$N)PhLac-MeLeu-Lac-MeLeu-PhLac-MeLeu-Lac] (1.06 g) was dissolved in DMF (5 ml), and to the solution were added 2-bromoethylether (383 mg), potassium carbonate (228 mg) and sodium iodide (124 mg). The resultant mixture was stirred at 90° C. for 5 hours to conduct the reaction. The reaction solution obtained was diluted with ethyl acetate (100 ml), and the diluted solution was washed twice with water (100 ml each) and was dried over anhydrous sodium sulfate. The solvent was removed from the dried solution by evaporation under a reduced pressure. The residue was purified by a silica gel column chromatography (eluted with ethyl acetate-hexane=1:1, v/v), thus affording the titled compound (420 mg; 37%) as white powder.

$[\alpha]_D = -75.3°$ (c=0.19,CHCl$_3$); NMR(CDCl$_3$): δ=0.80–1.05(24H,m, δ-CH$_3$(MeLeu)), 1.24–1.86(18H,m, β-CH$_3$(Lac), β-CH$_2$, γ-CH(MeLeu)), 2.64–3.49(20H,m,N—Me, β-CH$_2$((Mor)PhLac,PhLac), CH$_2$NCH$_2$(Mor)), 3.73–3.86(4H,m,CH$_2$OCH$_2$(Mor)), 4.32–5.70(8H,m, α-CH), 6.81,7.12(each 2H, each d, each J=9H z,aromatic ((Mor)PhLac)), 7.27(5H,m,aromatic(PhLac)).

EXAMPLE 66

Cyclo[MeLeu-(o-Mor)PhLac-MeLeu-Lac-MeLeu-(p-Mor)PhLac-MeLeu-Lac] (Compound Code No. PF1022-280 substance) and Cyclo[MeLeu-(o-Mor)PhLac-MeLeu-Lac]$_2$ (Compound Code No. PF1022-281 substance)

Fuming nitric acid (100 g) was cooled to −40° C. to −50° C., and then added with PF1022 substance (20 g) slowly while maintaining the temperature below −20° C. The resultant mixture was stirred at −25° C. to −20° C. for 1 hour to conduct the reaction. The reaction solution obtained was poured into ice-water (1 liter) and well stirred until a pale yellow powder was formed. This powder was collected by filtration and dried, and the dry powder, without purification, was dissolved in methanol (400 ml). To the solution obtained was added a 10% Pd/carbon (2 g). The resultant mixture was subjected to catalytic reduction under atmospheric pressure for 3 hours.

The reaction solution so obtained was filtered to remove the catalyst, and the resultant filtrate was concentrated to dryness. The solid residue, without purification, was dissolved in DMF (60 ml), and to the solution were added bromoethyl ether (8 ml), potassium carbonate (8.9 g) and sodium iodide (4.8 g). The resultant mixture was stirred at 90° C. for 3 hours to conduct the reaction. The reaction solution obtained was diluted with ethyl acetate (1 liter), and washed twice with water (1 liter each) and was dried over anhydrous sodium sulfate. The solvent was evaporated off from the dried solution under a reduced pressure. The residue was purified by a silica gel column chromatography (eluted with ethyl acetate-hexane=2:1, v/v) followed by column chromatography using ODS reverse phase (eluted with CH$_3$CN—H$_2$O=2:1, v/v), thus to afford both the titled compounds (310 mg and 180 mg, respectively), each as white powder.

PF1022-280 substance: $[\alpha]_D = -104°$ (c=0.38,CHCl$_3$); NMR(CDCl$_3$): δ=0.80–1.06(24H,m, δ-CH$_3$(MeLeu)), 1.22–1.81(18H,m, β-CH$_3$(Lac), β-CH$_2$, γ-CH(MeLeu)), 2.73–3.18(24H,m,N—Me, β-CH$_2$((o-Mor)PhLac,(Mor)PhLac), CH$_2$NCH$_2$(Mor)), 3.80–3.87(8H,m,CH$_2$O CH$_2$(Mor)), 4.46–5.72(8H,m, α-CH), 6.73–6.84(5H,m, aromatic), 7.12–7.21(3H,m,aromatic) MS(SIMS): 1119(M+ 1); PF1022-281 substance: $[\alpha]_D = -85.9°$ (c=0.22,CHCl$_3$); NMR(CDCl$_3$): δ=0.78–1.04(24H,m, δ-CH$_3$(MeLeu)), 1.10–1.84(18H,m, β-CH$_3$(Lac), β-CH$_2$, γ-CH(MeLeu)), 2.75–3.27(24H,m,N—Me, β-CH$_2$((o-Mor)PhLac,(Mor) PhLac),CH$_2$NCH$_2$(Mor)), 3.83(8H,bs,CH$_2$OCH$_2$(Mor)), 4.32–6.09(8H,m, α-CH), 7.00–7.30(8H,m,aromatic); MS(SIMS): 1119(M+1).

EXAMPLE 67

Cyclo[MeLeu-Lac-MeLeu-(p-t-Bu)PhLac-MeLeu-Lac-MeLeu-PhLac] (Compound Code No. PF1022-051 substance) and Cyclo[MeLeu-Lac-MeLeu-(p-t-Bu)PhLac]$_2$ (Compound Code No. PF1022-050 substance)

To a suspension of PF1022 substance (2.0 g) in pivaloyl chloride (10 ml) was added aluminum chloride (2.13 g) in small portions under ice-cooling. The resultant mixture was then warmed up to 80° C. over 1 hour. Immediately thereafter, the reaction solution as obtained was allowed to cool to room temperature over 30 minutes. The solid material formed in the solution was separated and dissolved in ethyl acetate (4 ml). The resulting solution was diluted with ethyl acetate (100 ml) and the diluted solution was washed successively with cold water (50 ml) containing concentrated hydrochloric acid(2 ml), water (50 ml), an aqueous saturated sodium hydrogen carbonate solution (50 ml) and an aqueous saturated sodium chloride solution (50 ml) and was dried over anhydrous sodium sulfate. The dried solution was concentrated under a reduced pressure, and the resulting residue was purified by a silica gel column chromatography (eluted with ethyl acetate-hexane=1:5~1:1), thus to afford both the titled compounds, PF1022-050 substance (229 mg) and PF1022-051 substance (400 mg), each as white powder. Further, PF1022 substance (460 mg) was recovered.

PF1022-050 substance: $^1$H-NMR(CDCl$_3$): δ=0.7–1.1 (27H,m), 1.15–1.90(33H,m), 2.6–3.25(16H,m), 4.47(1H, m), 5.0–5.8(7H,m), 7.0–7.35(8H,m) MS(SIMS): 1060(M+ 1); PF1022-051 substance: $^1$H-NMR(CDCl$_3$): δ=0.7–1.1 (27H,m), 1.2–1.85(24H,m), 2.64–3.20(16H,m), 4.46(1H, m), 5.0–5.75(7H,m), 7.0–7.45(9H,m); MS(SIMS): 1005 (M+1).

EXAMPLE 68

Cyclo[MeLeu-Lac-MeLeu-(t-BuO)PhLac]$_2$ (Compound Code No. PF1022-222 substance)

PF1022 H substance.(3.59 g) was dissolved in a mixture of methylene chloride (36 ml) and ethyl acetate (1.8 ml), and to the resulting solution were added isobutene (7 ml) and concentrated sulfuric acid (0.6 ml) at −40° C. The resultant mixture was stirred at room temperature for 1 hour in a sealed reaction vessel. The reaction solution so obtained was again cooled to −40° C. and the reaction vessel was opened, into which reaction vessel isobutene (7 ml) was again introduced. The reaction vessel was again sealed and its content was stirred at room temperature for 14 hours and then cooled again to −30° C. The reaction vessel was opened. To the reaction solution obtained was added triethylamine (4 ml), and the solvent was evaporated off from the solution under a reduced pressure.

The residue so obtained was dissolved in ethyl acetate (250 ml) and the resulting solution was washed, successively, with a 5% potassium hydrogen sulfate and a 20% aqueous sodium chloride solution and was dried over anhydrous magnesium sulfate. The solvent was evaporated off from the dried solution under a reduced pressure. The residue was purified by a silica gel column chromatography (eluted with chloroform-ethyl acetate=2:1, v/v), thus affording the titled compound (1.43 g; 35.7%) as white powder.

[α]$_D$=−113° (c=0.1,MeOH); $^1$H-NMR(CDCl$_3$): δ=0.85–1.05(27H,m), 1.32(18H,s), 1.39(3H,d,J=0.7), 1.41–1.93(12H,m), 2.69–2.96(12H,m), 3.08(4H,m), 4.50–5.64(8H,m), 7.02(8H,d d); MS(SIMS): 1093(M+1).

EXAMPLE 69

Cyclo[MeLeu-Lac-MeLeu-(BTH)Lac-MeLeu-Lac-MeLeu-PhLac] (Compound Code No. PF1022-038 substance)

Triphenylphosphine oxide (1.79 g) was dissolved in methylene chloride (10 ml) under a nitrogen atmosphere, and to the solution was added a 0.7M solution (4.5 ml) of anhydrous trifluoromethane sulfonic acid in methylene chloride under ice-cooling. The resultant mixture was stirred at 0° C. for 30 minutes. Thereafter, to the reaction solution so obtained was added, dropwise, a solution of Cyclo[MeLeu-Lac-MeLeu-(HOCO)Lac-MeLeu-Lac-MeLeu-PhLac] (1.18 g) and orthoaminothiophenol (0.14 ml) in methylene chloride (5.5 ml). The mixture obtained was stirred at 0° C. for 2 hours.

To the resulting reaction solution was added chloroform (30 ml), and the resultant mixture was washed, successively, with a 5% potassium hydrogen sulfate (30 ml), an aqueous saturated sodium hydrogen carbonate solution (30 ml×2) and an aqueous saturated sodium chloride solution (30 ml) and was dried over anhydrous sodium sulfate. The solvent was evaporated off from the dried solution under a reduced pressure, and then ethyl acetate (30 ml) and diethylether (50 ml) were added to the residue obtained. The precipitate formed in the resulting solution was filtered off, and the filtrate obtained was concentrated to give a residue. While, 0.7M solution (4.5 ml) of anhydrous trifluoromethane sulfonic acid in methylene chloride was added to an ice-cooled solution of triphenylphosphine oxide (1.79 g) in methylene chloride (10 ml) under a nitrogen atmosphere, and the resultant mixture was stirred at 0° C. for 1 hour. To the mixture after the stirring was then added the methylene chloride solution of the residue mentioned just above. The resultant mixture was slowly warmed up to room temperature and stirred at room temperature for 2 hours and 45 minutes.

To the thus resulting reaction solution was added chloroform (30 ml). The resultant mixture was washed, successively, with water (30 ml) and an aqueous saturated sodium hydrogen carbonate solution (30 ml) and was dried over anhydrous sodium sulfate. After the dried solution was concentrated under a reduced pressure, ethyl acetate (1 ml) and diethylether (20 ml) were added to the residue obtained. The precipitate as formed in the resulting solution was filtered off, and the filtrate was concentrated. Again, diethylether (15 ml) was added to the residue obtained. The precipitate formed in the resulting solution again was filtered off, and the filtrate was concentrated. The residue so obtained by the concentration of the latter filtrate was purified by silica gel column chromatography (two times) (eluted with chloroform-ethyl acetate 8:1 and with toluene-ethyl acetate=3:1~2:1), thus to afford the titled compound (418 mg) as white powder.

[α]$_D$=−109° (c=0.11,MeOH); $^1$H-NMR(CD$_3$OD,KSCN was added): δ=0.70–1.02(24H,m), 1.18–1.90(18H,m), 2.93 (3H,s), 2.96(3H,s), 3.03(3H,s), 3.18(3H,s), 3.0–3.2(2H,m), 3.6–3.8(2H,m), 5.28–5.50(6H,m), 5.56(1H,dd,J=5.9,8.6 Hz), 5.95(1H,dd,J=5.4,8.2 Hz), 7.22–7.60(7H,m), 8.0(2H,t, J=8.1 Hz); MS(SIMS): 1006(M+1).

EXAMPLE 70

Cyclo[MeLeu-Lac-MeLeu-(BTH)Lac]$_2$ (Compound Code No. PF1022-037 substance)

Triphenylphosphine oxide (3.65 g) was dissolved in 1,2-dichloroethane (20 ml) under a nitrogen atmosphere, and to the solution was added, under ice-cooling, a 0.7M solution (9.5 ml) of trifluoromethanesulfonic anhydride in methylene chloride. The resultant mixture was stirred at 0° C. for 30 minutes. To said mixture were then added dropwise Cyclo [MeLeu-Lac-MeLeu-(HOCO)Lac-MeLeu-Lac-MeLeu-(HOCO)Lac] (1.16 g) and a solution of ortho-aminothiophenol (0.31 ml) in 1,2-dichloroethane (11 ml). The resultant mixture was warmed up to 80° C. over 45 minutes and stirred at the same temperature for 1 hour.

Chloroform (50 ml) was added to the resulting reaction solution, and the mixture so obtained was washed with water (30 ml) and dried over anhydrous sodium sulfate. The dried solution was concentrated under a reduced pressure, and the residue obtained was purified by a silica gel column chromatography (eluted with chloroform-ethyl acetate= 8:1~10:3), thus affording the titled compound (0.26 g) as white powder.

[α]$_D$=−65.1° (c=0.10,MeOH); $^1$H-NMR(CDCl$_3$): δ=0.5–1.1(27H,m), 1.18–1.85(15H,m), 2.76–3.76(16H,m), 4.49(1H,dd,J=5.3,9.7 Hz), 5.09(1H,q,J=6.8 Hz), 5.22–5.62 (4H,m), 6.08(1H,t,J=7.5 Hz), 6.17(1H,t,J=7.3 Hz), 7.30–7.58(4H,m), 7.80–8.00(4H,m); MS(FD): 1062(M).

EXAMPLE 71

Cyclo[MeLeu-Lac-MeLeu-(BIM)Lac-MeLeu-Lac-MeLeu-PhLac] (Compound Code No. PF1022-040 substance)

Cyclo[MeLeu-Lac-MeLeu-(HOCO)Lac-MeLeu-Lac-MeLeu-PhLac] (366 mg), ortho-phenylenediamine (55.9 mg), BOP-Cl (142.7 mg) and diisopropylethylamine (0.16 ml) were dissolved in methylene chloride (15 ml), and the resulting solution as stirred at room temperature for 4 hours. Chloroform (30 ml) was added to the reaction solution so obtained. The resultant mixture was washed with an aqueous saturated sodium hydrogen carbonate solution (30 ml), and dried over anhydrous sodium sulfate and was concentrated under a reduced pressure. The resulting residue was purified by a silica gel column chromatography (eluted with chloroform-methanol=100:1). The main product (389 mg) was dissolved in benzene (40 ml), and to the solution was added p-toluenesulfonic acid hydrate (14.5 mg). The resultant mixture was heated under reflux in a Dean-Stark apparatus for 4 hours. Then, additional amount (70 mg) of p-toluenesulfonic acid hydrate was added to the reaction mixture in said apparatus, and the heating of the mixture under reflux was continued for further 5 hours. After the reaction solution so obtained was allowed to cool to room temperature, ethyl acetate (50 ml) was added thereto. The resultant mixture was washed with an aqueous sodium hydrogen carbonate solution (40 ml), dried over anhydrous sodium sulfate and concentrated under a reduced pressure to remove the solvent. The resulting residue was purified by a silica gel column chromatography (eluted with chloroform-methanol=100:1~50:1), thus to afford the titled compound (243.7 mg) as white powder.

[α]$_D$=−108° (c=0.11,MeOH); $^1$H-NMR(CD$_3$OD,KSCN was added): δ=0.66(3H,d,J=6.5 Hz), 0.77(3H,d,J=6.5 Hz), 0.80–0.98(18H,m), 1.10–1.88(18H,m), 2.90,2.92,3.01,3.15 (3H×4, each s), 3.0–3.2(2H,m), 3.33(1H,dd,J=10.0,15.0 Hz), 3.48(1H,dd,J=4.9,15.0 Hz), 5.26–5.48(6H,m), 5.54 (1H,dd,J=5.5,9.0 Hz), 5.84(1H,dd,J=4.9,10.0 Hz), 7.20–7.38(7H,m), 7.55(2H,bs); MS(FAB): 989(M+1).

EXAMPLE 72

Cyclo[MeLeu-Lac-MeLeu-(ATH)PhLac]$_2$ (Compound Code No. PF1022-056 substance)

Cyclo[MeLeu-Lac-MeLeu-(CH$_3$CO)PhLac]$_2$ (Compound Code No. PF1022-048 substance) (321 mg), which was obtained in Example 49, was dissolved in chloroform (20 ml), and to the solution were added a 1.56M solution (0.4 ml) of bromine in chloroform and a 48% hydrobromic acid (1 drop). The resultant mixture was stirred at room temperature for 2 hours. The reaction solution so obtained was diluted with chloroform (30 ml) and then washed with an aqueous sodium hydrogen carbonate solution (30 ml). The aqueous layer (the aqueous washing) was further extracted with chloroform (30 ml). The organic layers (the solution in chloroform) were combined together, dried over anhydrous sodium sulfate and concentrated under a reduced pressure.

The resulting residue was dissolved in THF (15 ml), and to the solution were added thiourea (96 mg), sodium hydrogen carbonate (130 mg) and water (1 ml). The resultant mixture was stirred at room temperature for 1 hour. After ethyl acetate (50 ml) was added to the resulting reaction solution, the latter solution was washed with an aqueous saturated sodium hydrogen carbonate solution (30 ml), and was dried over anhydrous sodium sulfate and concentrated under a reduced pressure. The resulting residue was purified by a silica gel column chromatography (eluted with chloroform-methanol=50:1~50:2), thus to afford the titled compound (216 mg) as white powder.

$[\alpha]_D = -86.2°$ (c=0.11,MeOH); $^1$H-NMR(CDCl$_3$): δ=0.74–1.06(27H,m), 1.20–1.84(15H,m), 2.70–3.22(16H, m), 4.48(1H,m), 4.96(4H,bs), 5.08(1H,q,J=7.0 Hz), 5.16–5.72(6H,m), 5.71(2H,s), 7.20–7.30(4H,m), 7.64–7.76 (4H,m); MS(electrospray): 1145(M+1), 1167(M+Na).

Industrial Applicability

Novel cyclodepsipeptide derivatives of PF1022 substance, which are represented by the general formulae (I), (II) and (III) above, are now provided according to this invention and have anthelmintic activities against a variety of helminths or parasites living in human and in food animals and companion animals. They are therefore useful as anthelmintic agent both for the prevention and therapeutic treatment of parasitic infections.

What is claimed is:

1. A cyclodepsipeptide compound derived from PF1022 substance, which is represented by the following general formula(I)

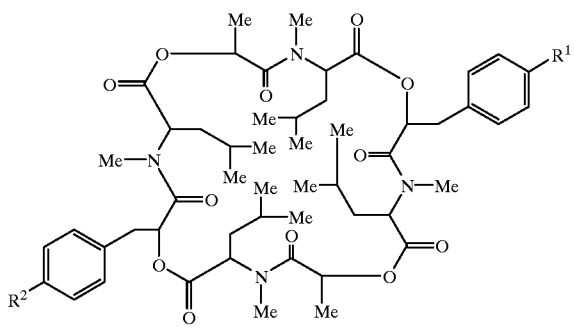

wherein (i) $R^1$ stands for a hydrogen atom and $R^2$ stand for a cyano-($C_1$–$C_6$)alkoxy group, a thiocarbamoyl-($C_1$–$C_6$) alkoxy group, an amino-($C_1$–$C_6$)alkoxy group, an amino-($C_1$–$C_6$)alkoxy group having t-butyloxycarbonyl group as an amino-protecting group, an N-mono-($C_1$–$C_6$)alkylamino-($C_1$–$C_6$)alkoxy group, an N,N-di-($C_1$–$C_6$) alkylamino-($C_1$–$C_6$)alkoxy group, an N,N-di-(($C_1$–$C_6$)alkoxy-($C_1$–$C_6$) alkyl)amino-($C_1$–$C_6$)alkoxy group, or a cyclic amino-($C_1$–$C_6$)alkoxy group of which the cyclic amino group is morpholino group, pyrrolidino group or piperidino group; or $R^2$ is a ($C_1$–$C_6$)alkoxy group having, as a substituent thereon, a saturated or unsaturated 5- or 6-membered heterocyclic ring which is chosen from pyrrolidine, imidazole, thiazole, furan, tetrahydrofuran, a 5-($C_1$–$C_6$)alkyl-1,2,4-oxadiazole, a 5-(halo-substituted or unsubstituted)phenyl-1, 2,4-oxadiazole, a 5-($C_3$–$C_6$)cycloalkyl-1,2,4-oxadiazole, a halo-substituted or unsubstituted pyridine, and an N-alkyl-substituted or unsubstituted tetrahydropyrimidine and which heterocyclic ring may further optionally have as a substituent a phenyl group or a phenyl group substituted by a halo group selected from the group consisting of chlorine, bromine and fluorine; or $R^2$ is a ($C_2$–$C_6$)alkanoyl group optionally having a substituent which is selected from the group consisting of a halogen atom and a hydroxyl group, or $R^2$ is a carbamoyl group, an N-mono-($C_1$–$C_6$)alkylcarbamoyl group, or an N,N-di-($C_1$–$C_6$)alkylcarbamoyl group, or a cyclic amino-carbonyl group of which the cyclic amino group is morpholino group, pyrrolidino group or piperidino group; or $R^2$ is an N-mono-($C_1$–$C_6$)alkylamino-alkoxycarbonyl group, or an N,N-di-($C_1$–$C_6$)alkylamino-($C_1$–$C_6$)alkoxycarbonyl group, or a cyclic amino-($C_1$–$C_6$) alkoxycarbonyl group of which the cyclic amino group is morpholino group, pyrrolidino group or piperidino group; or $R^2$ is a formyloxy-($C_1$–$C_6$)alkylcarbonyl group; or $R^2$ is a carboxyl group or 2-aminothiazolyl group; or alternatively (ii) $R^1$ and $R^2$ are identical to each other and each stand for a cyano-($C_1$–$C_6$)alkoxy group, a thiocarbamoyl-($C_1$–$C_6$) alkoxy group, an amino-($C_1$–$C_6$)alkoxy group, an amino-($C_1$–$C_6$)alkoxy group having t-butyloxycarbonyl group as an amino-protecting group, an N-mono-($C_1$–$C_6$)alkylamino-($C_1$–$C_6$)alkoxy group, an N,N-di-($C_1$–$C_6$)alkylamino-($C_1$–$C_6$)alkoxy group, an N,N-di-(($C_1$–$C_6$)alkoxy-($C_1$–$C_6$) alkyl)amino-($C_1$–$C_6$)alkoxy group, or a cyclic amino-($C_1$–$C_6$)alkoxy group of which the cyclic amino group is morpholino group, pyrrolidino group or piperidino group; or $R^1$ and $R^2$ each stand for a ($C_1$–$C_6$)alkoxy group having, as a substituent thereon, a saturated or unsaturated 5- or 6-membered heterocyclic ring which is chosen from pyrrolidine, imidazole, thiazole, furan, tetrahydrofuran, a 5-($C_1$–$C_6$)alkyl-1,2,4-oxadiazole, a 5-(halo-substituted or unsubstituted) phenyl-1,2,4-oxadiazole, a 5-($C_3$–$C_6$) cycloalkyl-1,2,4-oxadiazole, a halo-substituted or unsubstituted pyridine, and an N-alkyl-substituted or unsubstituted tetrahydropyrimidine, and which heterocyclic ring may further optionally have as a substituent a phenyl group or a phenyl group substituted by a halo group selected from the group consisting of chlorine, bromine or fluorines or $R^1$ and $R^2$ each stand for a ($C_2$–$C_6$)alkanoyl group optionally having a substituent which is selected from the group consisting of a halogen atom and hydroxyl group; or $R^1$ and $R^2$ each stand for a carbamoyl group, an N-mono-($C_1$–$C_6$) alkylcarbamoyl group, or an N,N-di-($C_1$–$C_6$) alkylcarbamoyl group, or a cyclic amino-carbonyl group of which the cyclic amino group is morpholino group, pyrrolidino group or piperidino group; or $R^1$ and $R^2$ each stand for an N-mono-($C_1$–$C_6$)alkylamino-($C_1$–$C_6$)alkoxycarbonyl group, or an N,N-di-($C_1$–$C_6$)alkylamino-($C_1$–$C_6$) alkoxycarbonyl group, or a cyclic amino-($C_1$–$C_6$) alkoxycarbonyl group of which the cyclic amino group is morpholino group, pyrrolidino group or piperidino group; or $R^1$ and $R^2$ each stand for a formyloxy-($C_1$–$C_6$)alkylcarbonyl group, or a carboxyl group or 2-aminothiazolyl group, and Me stands for methyl group.

2. A compound as claimed in claim 1, wherein (i) $R^1$ is a hydrogen atom and $R^2$ is a cyanomethoxy group, thiocarbamoylmethoxy group, 2-aminoethoxy group, 2-(N-t- butyloxycarbonylamino)ethoxy group, a 2-(N-mono-($C_1$–$C_6$)alkylamino)ethoxy or 3-(N-mono-($C_1$–$C_6$) alkylamino)propoxy group, a 2-(N,N-di-($C_1$–$C_6$) alkylamino)ethoxy or 3-(N,N-di-($C_1$–$C_6$) alkylamino) propoxy group, a 2-(N,N-di-(($C_1$–$C_6$)alkoxy-($C_1$–$C_6$)alkyl) amino)ethoxy group, 2-morpholinoethoxy group, 2-pyrrolidinoethoxy group or 2-piperidinoethoxy group; or $R^2$ is a methoxy group substituted by a heterocyclic ring which is pyrrolidine, imidazole, thiazole, furan, tetrahydrofuran, a 5-(linear or branched $C_1$–$C_6$)alkyl-1,2,4-oxadiazole, a 5-(optionally halo-substituted)phenyl-1,2,4-oxadiazole, a 5-($C_3$–$C_6$)cycloalkyl-1,2,4-oxadiazole, a pyridine optionally substituted by a halogen atom, or an N—($C_1$–$C_6$)alkyl-tetrahydropyrimidine; or $R^2$ is an acetyl group optionally substituted by a substituent selected from the group consisting of a halogen group and hydroxyl group; or $R^2$ is a carbamoyl group, N-methylcarbamoyl group, N,N-dimethylcarbamoyl group, morpholinocarbonyl group, an N-mono-($C_1$–$C_6$)alkylaminoethoxycarbonyl group, an N,N-di-($C_1$–$C_6$)alkylaminoethoxycarbonyl group, morpholinoethoxycarbonyl group, formyloxymethylcarbonyl group, carboxyl group or 2-aminothiazolyl group; or alternatively (ii) $R^1$ and $R^2$ are identical to each other and each are a cyanomethoxy group, thiocarbamoylmethoxy group, 2-aminoethoxy group, 2-(N-t-butyloxy-carbonylamino) ethoxy group, a 2-(N-mono-($C_1$–$C_6$)alkylamino)ethoxy or 3-(N-mono-($C_1$–$C_6$)alkylamino)propoxy group, a 2-(N,N-di-($C_1$–$C_6$)alkylamino)ethoxy or 3-(N,N-di-($C_1$–$C_6$) alkylamino)propoxy group, a 2-(N,N-di-(($C_1$–$C_6$)alkoxy-($C_1$–$C_6$)alkyl)amino)ethoxy group, 2-morpholinoethoxy group, 2-pyrrolidinoethoxy group, 2-piperidinoethoxy group; or $R^1$ and $R^2$ each are a methoxy group substituted by a heterocyclic ring which is pyrrolidine, imidazole, thiazole, furan, tetrahydrofuran, a 5-(linear or branched $C_1$–$C_6$)alkyl-1,2,4-oxadiazole, a 5-(optionally halo-substituted)phenyl-1, 2,4-oxadiazole, a 5-($C_3$–$C_6$)cycloalkyl-1,2,4oxadiazole, a pyridine optionally substituted by a halogen atom, or an N—($C_1$–$C_6$)alkyl-tetrahydropyrimidine, or $R^1$ and $R^2$ are each an acetyl group optionally substituted by a substituent selected from the group consisting of a halogen group and hydroxyl group; or $R^1$ and $R^2$ are each a carbamoyl group, N-methylcarbamoyl group, N,N-dimethylcarbamoyl group, morpholinocarbonyl group, an N-mono-($C_1$–$C_6$) alkylamino-ethoxycarbonyl group, an N,N-di-($C_1$–$C_6$) alkylamino-ethoxycarbonyl group, morpholinoethoxycarbonyl group, formyloxymethylcarbonyl group, carboxyl group or 2-amino-thiazolyl group.

3. A compound as claimed in claim 1, wherein (i) $R^1$ is a hydrogen atom, and $R^2$ is a cyano-($C_1$–$C_6$)alkoxy group, a thiocarbamoyl-($C_1$–$C_6$)alkoxy group, an amino-($C_1$–$C_6$) alkoxy group, an amino-($C_1$–$C_6$)alkoxy group having t-butyloxycarbonyl group as an amino-protecting group, an N-mono-($C_1$–$C_6$)alkylamino-($C_1$–$C_6$)alkoxy group, an N,N-di-($C_1$–$C_6$)alkylamino-($C_1$–$C_6$)alkoxy group, an N,N-di-(($C_1$–$C_6$)alkoxy-($C_1$–$C_6$)alkyl)amino-($C_1$–$C_6$)alkoxy group, or a cyclic amino-($C_1$–$C_6$)alkoxy group of which the cyclic amino group is morpholino group, pyrrolidino group or piperidino group; or alternatively (ii) $R^1$ and $R^2$ are identical to each other and each are a cyano-($C_1$–$C_6$)alkoxy group, a thiocarbamoyl-($C_1$–$C_6$)-alkoxy group, an amino-($C_1$–$C_6$) alkoxy group, an amino-($C_1$–$C_6$)alkoxy group having t-butyloxycarbonyl as an amino-protecting group, an N-mono-($C_1$–$C_6$)alkylamino-($C_1$–$C_6$)alkoxy group, an N,N-di-($C_1$–$C_6$)alkylamino-($C_1$–$C_6$)alkoxy group or an N,N-di-(($C_1$–$C_6$)alkoxy-($C_1$–$C_6$)alkyl)amino-($C_1$–$C_6$)alkoxy group or $R^1$ and $R^2$ each are a cyclic amino-($C_1$–$C_6$)alkoxy group of which the cyclic amino group is morpholino group, pyrrolidino group or piperidino group.

4. A compound as claimed in claim 3, wherein (i) $R^1$ is a hydrogen atom, and $R^2$ is a cyanomethoxy group, thiocarbamoylmethoxy group, 2-aminoethoxy group, 2-(N-t-butyloxycarbonylamino)ethoxy group, a 2-(N-mono-($C_1$–$C_6$)alkylamino)ethoxy or 3-(N-mono-($C_1$–$C_6$) alkylamino)propoxy group, a 2-(N,N-di-($C_1$–$C_6$) alkylamino)ethoxy or 3-(N,N-di-($C_1$–$C_6$)alkylamino) propoxy group, a 2-(N,N-di-(($C_1$–$C_6$)alkoxy-($C_1$–$C_6$)alkyl) amino)ethoxy group, 2-morpholinoethoxy group, 2-pyrrolidinothethoxy group or 2-piperidinoethoxy group; or alternatively (ii) $R^1$ and $R^2$ are identical to each other and each are a cyanomethoxy group, 2-aminoethoxy group, 2-(N-t-butyloxycarbonyl-amino)ethoxy group, a 2-(N-mono-($C_1$–$C_6$)-alkylamino)ethoxy or 3-(N-mono-($C_1$–$C_6$) alkylamino)propoxy group, a 2-(N,N-di-($C_1$–$C_6$) alkylamino)ethoxy or 3-(N,N-di-($C_1$–$C_6$)alkylamino) propoxy group, a 2-(N,N-di-(($C_1$–$C_6$)alkoxy-($C_1$–$C_6$)alkyl) amino)ethoxy group, 2-morpholinoethoxy group, 2-pyrrolidinoethoxy group or 2-piperidinoethoxy group.

5. A cyclodepsipeptide compound according to claim 1 wherein (i) $R^1$ is a hydrogen atom, and $R^2$ is a ($C_1$–$C_6$) alkoxy group having, as a substituent, a saturated or unsaturated 5- or 6-membered heterocyclic ring which is chosen from pyrrolidine, imidazole, thiazole, furan, tetrahydroguran, a 5-($C_1$–$C_6$)alkyl-1,2,4-oxadiazole, a 5-(halo-substituted or unsubstituted)phenyl-1,2,4-oxadiazole a 5-($C_3$–$C_6$)cycloalkyl-1,2,4-oxadiazole, a halo-substituted or unsubstituted pyridine, and an N-alkyl-substituted or unsubstituted tetrahydropyrimidine and which heterocyclic ring may optionally have, as a substituent thereon, a phenyl group optionally substituted by a halo group selected from the group consisting of chlorine, bromine and flourine; or alternatively (ii) $R^1$ and $R^2$ are each independently a ($C_1$–$C_6$)alkoxy group having as a substituent a saturated or unsaturated or unsaturated 5- or 6-membered heterocyclic ring which is chosen from pyrrolidine, imidazole, thiazole, furan, tetrahydrofuran, a 5-($C_1$–$C_6$)alkyl-1,2,4-oxadiazole, a 5-(halo-substituted or unsubstituted) phenyl-1,2,4-oxadiazole, a 5-($C_3$–$C_6$)alkyl-1, 2,4-oxadiazole, a halo-substituted or unsubstituted pyridine, and an N-alkyl-substituted or unsubstituted tetrahydropyrimidine and which heterocyclic ring may optionally have, as a substituent thereon, a phenyl group optionally substituted by a halo group selected from the group consisting of chlorine, bromine and flourine.

6. A compound as claimed in claim 1, wherein (i) $R^1$ is a hydrogen atom, and $R^2$ is a ($C_2$–$C_6$)alkanoyl group optionally substituted by a halogen atom or hydroxy group; or $R^2$ is a carbamoyl group, an N-mono-($C_1$–$C_6$)alkylcarbamoyl group, an N,N-di-($C_1$–$C_6$)alkylcarbamoyl group or a cyclic amino-carbonyl group of which the cyclic amino group is morpholino group, pyrrolidino group or piperidino group; or $R^2$ is an N-mono-($C_1$–$C_6$)alkylamino-alkoxycarbonyl group, an N,N-di-($C_1$–$C_6$)alkylamino-alkoxycarbonyl group, a cyclic amino-($C_1$–$C_6$)alkoxycarbonyl group of which the cyclic amino group is morpholino group, pyrrolidino group or piperidino group; or $R^2$ is a formyloxy-($C_1$–$C_6$)alkylcarbonyl group, carboxyl group or 2-aminothiazolyl group; or alternatively (ii) $R^1$ and $R^2$ are identical to each other and each are a ($C_2$–$C_6$)alkanoyl group optionally substituted by a halogen atom or hydroxyl group; or $R^1$ and $R^2$ each are a carbamoyl group, an N-mono-($C_1$–$C_6$)alkylcarbamoyl group, an N,N-di-($C_1$–$C_6$)alkyl carbamoyl group, a cyclic amino-carbonyl group of which the cyclic amino group is morpholino group, pyrrolidino group or piperidino group; or $R^1$ and $R^2$ each are an N-mono-($C_1$–$C_6$)alkylamino-alkoxycarbonyl group, an N,N-di- ($C_1$–$C_6$)alkylamino-alkoxycarbonyl group or a cyclic amino-($C_1$–$C_6$)-alkoxycarbonyl group of which the cyclic amino group is morpholino group, pyrrolidino group or piperidino group; or $R^1$ and $R^2$ each are a formyloxy-($C_1$–$C_6$)alkylcarbonyl group, carboxyl group or 2-aminothiazolyl group.

7. A compound as claimed in claim 6, wherein (i) $R^1$ is a hydrogen atom, and $R^2$ is a carboxyl group or an acetyl group optionally substituted by a halogen atom or hydroxyl group; or $R^2$ is a carbamoyl group, N-methylcarbamoyl group, an N,N-dimethylcarbamoyl group, morpholinocarbonyl group, an N-mono-($C_1$–$C_6$)alkylamino-ethoxycarbonyl group, an N,N-di-($C_1$–$C_6$)alkylamino-ethoxycarbonyl group, morpholinoethoxycarbonyl group, or formyloxymethlycarbonyl group; or alternatively (ii) $R^1$ and $R^2$ are identical to each other and each are a carboxyl group or an acetyl group optionally substituted by a halogen atom or hydroxyl group or $R^1$ and $R^2$ each are a carbamoyl group, an N-methylcarbamoyl group, an N,N-dimethylcarbamoyl group, a morpholinocarbonyl group, an N-mono-($C_1$–$C_6$) alkylamino-ethoxycarbonyl group, an N,N-di-($C_1$–$C_6$) alkylamino-ethoxycarbonyl group, a morpholinoethoxycarbonyl group or formyloxymethlycarbonyl group.

8. A compound selected from the group consisting of cyclo[MeLeu-Lac-MeLeu-(($C_2H_5$)$_2$NCH$_2$CH$_2$O)PhLac-MeLeu-Lac-MeLeu-PhLac]

cyclo[MeLeu-Lac-MeLeu-(($C_2H_5$)$_2$NHCH$_2$CH$_2$O)PhLac]$_2$ and cyclo[MeLeu-((CH$_3$OCH$_2$CH$_2$)$_2$NCH$_2$CH$_2$O)PhLac-MeLeu-Lac-MeLeu-PhLac-MeLeu-Lac].

9. Cyclo[MeLeu-(MorCH$_2$CH$_2$O)PhLac-MeLeu-Lac-MeLeu-PhLac-MeLeu-Lac].

10. A compound selected from the group consisting of cyclo[MeLeu-Lac-MeLeu-(furfuryloxy)PhLac-MeLeu-Lac-MeLeu-PhLac] and cyclo[MeLeu-Lac-MeLeu-(2-picolyloxy)PhLac]$_2$.

11. Cyclo[MeLeu-Lac-MeLeu-PhLac-MeLeu-Lac-MeLeu-(NH$_2$CO)PhLac].

12. An anthelmintic composition, characterized in that the composition comprises, as an active ingredient, at least one of the cyclodepsipeptides represented by the general formula (I) as defined in claim 1, or an acid addition salt thereof.

* * * * *

UNITED STATES PATENT AND TRADEMARK OFFICE
CERTIFICATE OF CORRECTION

PATENT NO.    : 6,329,338 B1
DATED         : December 11, 2001
INVENTOR(S)   : Sakanaka et al.

It is certified that error appears in the above-identified patent and that said Letters Patent is hereby corrected as shown below:

<u>Title page,</u>
-- [30] Foreign Application Priority Data
Sep. 22, 1995 (JP).................................7-244051 --

Signed and Sealed this

Nineteenth Day of March, 2002

Attest:

*Attesting Officer*

JAMES E. ROGAN
*Director of the United States Patent and Trademark Office*